(12) United States Patent
Scheidt et al.

(10) Patent No.: US 11,174,238 B2
(45) Date of Patent: Nov. 16, 2021

(54) ENANTIOSELECTIVE CROSS DEHYDROGENATIVE COUPLING REACTIONS AND COMPOUNDS SYNTHESIZED BY THE REACTIONS

(71) Applicant: Northwestern University, Evanston, IL (US)

(72) Inventors: Karl A. Scheidt, Evanston, IL (US); Ansoo Lee, Evanston, IL (US); Richard C. Betori, Gurnee, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/710,512

(22) Filed: Dec. 11, 2019

(65) Prior Publication Data

US 2020/0181106 A1    Jun. 11, 2020

Related U.S. Application Data

(60) Provisional application No. 62/778,016, filed on Dec. 11, 2018.

(51) Int. Cl.
*C07D 309/30* (2006.01)
*C07D 409/06* (2006.01)
*C07D 405/06* (2006.01)

(52) U.S. Cl.
CPC ......... *C07D 309/30* (2013.01); *C07D 405/06* (2013.01); *C07D 409/06* (2013.01)

(58) Field of Classification Search
CPC .................................................. C07D 405/06
See application file for complete search history.

(56) References Cited

U.S. PATENT DOCUMENTS

| | | |
|---|---|---|
| 7,851,640 B2 | 12/2010 | Scheidt |
| 8,481,760 B2 | 7/2013 | Bergan |
| 8,742,141 B2 | 6/2014 | Bergan |
| 8,912,341 B2 | 12/2014 | Scheidt |
| 9,260,564 B2 | 2/2016 | Lombardo |
| 9,334,297 B2 | 5/2016 | Scheidt |
| 9,527,812 B2 | 12/2016 | Scheidt |
| 9,643,947 B2 | 5/2017 | Scheidt |
| 9,839,625 B2 | 12/2017 | Bergan |
| 9,981,968 B2 | 5/2018 | Schiltz |
| 10,231,949 B2 | 3/2019 | Bergan |
| 10,323,039 B2 | 6/2019 | Scheidt |
| 2015/0065703 A1 | 3/2015 | Scheidt |
| 2016/0002252 A1 | 1/2016 | Schiltz |

OTHER PUBLICATIONS

Clarke et al., Org. Biomol. Chem., 2015, 13, 4743-4750.*
Patani et al. (Chem. Rev. 1996, 3147-3176).*
Vetica, F., et al. "Asymmetric organocatalytic methods for the synthesis of tetrahydropyrans and their application in total synthesis." Chemical Society Reviews 46.6 (2017): 1661-1674.
Wan et al., "Organocatalytic Redox Deracemization of Cyclic Benzylic Ethers Enabled by An Acetal Pool Strategy," Angew. Chem. Int. Ed. Engl. 2017, 56(18):5116-5120.
Wang, J. et al. "Highly stereoselective Brønsted acid catalyzed synthesis of spirooxindole pyrans." Organic letters 13.12(2011): 3086-3089.
Xie, Z. et al. "Copper-catalyzed aerobic enantioselective cross-dehydrogenative coupling of N-aryl glycine esters with terminal alkynes." Organic letters 18.12 (2016): 2982-2985.
Xie, Z., et al. "Organocatalytic enantioselective cross-dehydrogenative coupling of N-carbamoyl cyclic amines with aldehydes." Organic letters 18.16 (2016): 3944-3947.
Yang, Q., et al. "Visible-light-promoted asymmetric cross-dehydrogenative coupling of tertiary amines to ketones by synergistic multiple catalysis." Angewandte Chemie International Edition 56.13 (2017): 3694-3698.
Yeung, C. S., et al. "Catalytic dehydrogenative cross-coupling: forming carbon-carbon bonds by oxidizing two carbon-hydrogen bonds." Chemical reviews 111.3 (2011): 1215-1292.
Yi, H., et al. "Recent advances in radical C-H activation/radical cross-coupling." Chemical reviews 117.13 (2017) 9016-9085.
Ying, B.-P., et al. "Oxidative C-C Bond-Forming Reaction of Electron-Rich Alkylbenzyl Ether with Trimethylvinyloxysilane." Organic letters 6.10 (2004): 1523-1526.
Zhang, G. et al. "Catalytic Asymmetric Activation of a C? H Bond Adjacent to a Nitrogen Atom: A Versatile Approach to Optically Active a-Alkyl a-Amino Acids and C1-Alkylated Tetrahydroisoquinoline Derivatives." Angewandte Chemie International Edition 50.44 (2011): 10429-10432.
Zhang, J., et al. "Enantioselective Oxidative Cross-Dehydrogenative Coupling of Tertiary Amines to Aldehydes." Angewandte Chemie International Edition 51.15 (2012): 3649-3652.
Zhang, Y. et al. "Highly Efficient Cross-Dehydrogenative-Coupling between Ethers and Active Methylene Compounds." Angewandte Chemie International Edition 45.12 (2006): 1949-1952.
Betori, R. C., et al. (2017). A Biocatalytic Route to Highly Enantioenriched β-Hydroxydioxinones. Advanced synthesis & catalysis, 359(7), 1131-1137.
Brazeau, J-F, et al. "Stereocontrolled Synthesis of C1-C17 Fragment of Narasin via a Free Radical-Based Approach." Organic letters 12.1 (2010): 36-39.
Brizgys, G. J., et al. "Stereoselective piperidine synthesis through oxidative carbon-hydrogen bond functionalizations of enamides." Chemical Science 3.2 (2012): 438-442.
Carpenter, J., et al. "Total synthesis and structural revision of callipeltoside C." Angewandte Chemie International Edition 47.19 (2008): 3568-3572.

(Continued)

*Primary Examiner* — Kamal A Saeed
(74) *Attorney, Agent, or Firm* — Quarles & Brady LLP

(57) ABSTRACT

Disclosed are enantioselective cross dehydrogenative coupling reactions for synthesizing tetrahydropyran compounds. Novel tetrahydropyran compounds may be synthesized by the disclosed methods as well as tetrahydropyran precursor compounds for synthesizing various naturally occurring compounds. The enantioselective cross dehydrogenative coupling reactions utilize in situ Lewis Acid activation in combination with oxidative formation of an oxocarbenium ion to provide a highly efficient and selective coupling reaction for synthesizing tetrahydropyran compounds.

12 Claims, 5 Drawing Sheets

(56) References Cited

OTHER PUBLICATIONS

Chua, S. S., et al. "Indium (III) chloride-catalyzed Mukaiyama-Michael addition: synthesis of 2, 6-anti-tetrahydropyrans." Tetrahedron 67.27-28 (2011): 5079-5082.

Clarke, P. A., et al. "A Maitland-Japp inspired synthesis of dihydropyran-4-ones and their stereoselective conversion to functionalised tetrahydropyran-4-ones." Organic & biomolecular chemistry 13.16 (2015): 4743-4750.

Clarke, P. A., et al. "Strategies for the formation of tetrahydropyran rings in the synthesis of natural products." European journal of organic chemistry 2006.9 (2006): 2045-2053.

Colby, D. A., et al. "Rhodium catalyzed chelation-assisted C-H bond functionalization reactions." Accounts of chemical research 45.6 (2012): 814-825.

Crane, E. A., et al. "Enantioselective Synthesis of (-)-Exiguolide by Iterative Stereoselective Dioxinone-Directed Prins Cyclizations." Angewandte Chemie International Edition 50.39 (2011): 9112-9115.

Cui, Y et al. "Synthesis of sulfur-containing heterocycles through oxidative carbon-hydrogen bond functionalization." Organic letters 14.7 (2012): 1720-1723.

Cui, Y., et al. "Bimolecular coupling reactions through oxidatively generated aromatic cations: scope and stereocontrol." Tetrahedron 69.36 (2013): 7618-7626.

Custar, D. W., et al. "Total synthesis and structural revision of the marine macrolide neopeltolide." Journal of the American Chemical Society 130.3 (2008): 804-805.

Custar, D. W., et al. "Total synthesis and structure-activity investigation of the marine natural product neopeltolide." Journal of the American Chemical Society 131.34 (2009): 12406-12414.

Davies, HML, et al. "Recent advances in C-H functionalization." Journal of Organic Chemistry (2016): 343-350.

Diao, T et al. "Synthesis of cyclic enones via direct palladium-catalyzed aerobic dehydrogenation of ketones." Journal of the American Chemical Society 133.37 (2011): 14566-14569.

Evans, D. A., et al. "Enantioselective and Diastereoselective Mukaiyama-Michael Reactions Catalyzed by Bis (oxazoline) Copper (II) Complexes." Journal of the American Chemical Society 123.19 (2001): 4480-4491.

Evans, D. A., et al. "Enantioselective Synthesis of Dihydropyrans. Catalysis of Hetero Diels-Alder Reactions by Bis (oxazoline) Copper (II) Complexes." Journal of the American Chemical Society 122.8 (2000): 1635-1649.

Ferrie, L., et al. "Formal chemoselective synthesis of leucascandrolide A." Organic letters 9.13 (2007): 2461-2464.

Gensch, T., et al. "Mild metal-catalyzed C-H activation: examples and concepts." Chemical Society Reviews 45.10 (2016): 2900-2936.

Girard, S. A., et al. "The Cross-Dehydrogenative Coupling of C? H Bonds: A Versatile Strategy for C? C Bond Formations." Angewandte Chemie International Edition 53.1 (2014): 74-100.

Guo, C., et al. "Enantioselective Oxidative Cross-Coupling Reaction of 3-Indolylmethyl C? H Bonds with 1, 3-Dicarbonyls Using a Chiral Lewis Acid-Bonded Nucleophile to Control Stereochemistry." Angewandte Chemie International Edition 49.32 (2010): 5558-5562.

Gutekunst, W. R., et al. "C-H functionalization logic in total synthesis." Chemical Society Reviews 40.4 (2011) 1976-1991.

Han, X., et al. "Prins-Type Cyclization Reactions in Natural Product Synthesis." European Journal of Organic Chemistry 2013.7 (2013): 1193-1208.

Heravi, M. M., et al. "Recent applications of the hetero Diels-Alder reaction in the total synthesis of natural products." RSC Advances 5.123 (2015): 101999-102075.

Jasti, R., et al. "Axial-selective prins cyclizations by solvolysis of a-bromo ethers." Journal of the American Chemical Society 126.32 (2004): 9904-9905.

Larrosa, I. et al. "Synthesis of six-membered oxygenated heterocycles through carbon-oxygen bond-forming reactions." Tetrahedron 64.12 (2008): 2683-2723.

Lee et al., "An Enantioselective Cross-Dehydrogenative Coupling Catalysis Approach to Substituted Tetrahydropyrans," J. Am. Chem. Soc. 2018, 140, 6212-6216.

Lee, K. et al. "A Stereoselective Formal Synthesis of Leucascandrolide A." Organic letters 13.10 (2011): 2722-2725.

Lee, K. et al. "N-Heterocyclic Carbene Catalyzed Oxidative Macrolactonization: Total Synthesis of (+)-Dactylolide." Angewandte Chemie International Edition 51.23 (2012): 5735-5738.

Li, C.-J.. "Cross-dehydrogenative coupling (CDC): exploring C-C bond formations beyond functional group transformations." Accounts of chemical research 42.2 (2009): 335-344.

Liu, L. et al. "Cyclization reactions through DDQ-mediated vinyl oxazolidinone oxidation." Organic letters 11.14 (2009) 3152-3155.

Liu, L. et al. "Stereoselective synthesis of tertiary ethers through geometric control of highly substituted oxocarbenium ions." Angewandte Chemie International Edition 49.34 (2010): 5894-5897.

Lu, R., et al. "Redox deracemization of 1, 3,4, 9-tetrahydropyrano [3,4-b] indoles." Chemical Communications 54.35 (2018): 4445-4448.

Lyons, T. W. et al. "Palladium-catalyzed ligand-directed C-H functionalization reactions." Chemical reviews 110.2 (2010): 1147-1169.

Marmsäter, F. P., et al. "New efficient iterative approaches to polycyclic ethers." Chemistry—A European Journal 319 (2002): 4346-4353.

Meng, Z., et al. "Catalytic Enantioselective Oxidative Cross-Coupling of Benzylic Ethers with Aldehydes." Angewandte Chemie International Edition 53.2 (2014): 543-547.

Morris, W. J., et al. "Stereoselective synthesis of tetrahydropyran-4-ones from dioxinones catalyzed by scandium (III) triflate." Organic letters 7.6 (2005): 1113-1116.

Nasir, N. M., et al. "Strategies for the construction of tetrahydropyran rings in the synthesis of natural products." Organic & biomolecular chemistry 12.21 (2014): 3323-3335.

Nising, C. F., et al. "Recent developments in the field of oxa-Michael reactions." Chemical Society Reviews 41.3 (2012): 988-999.

Nising, C. F., et al. "The oxa-Michael reaction: from recent developments to applications in natural product synthesis." Chemical Society Reviews 37.6 (2008): 1218-1228.

Olier, C. et al. "Synthesis of tetrahydropyrans and related heterocycles via prins cyclization; extension to aza-prins cyclization." Tetrahedron 2010, 66, 413-445.

Ramnauth, J., et al. "Stereoselective C-glycoside formation by a rhodium (I)-catalyzed 1,4 addition of arylboronic acids to acetylated enones derived from glycals." Organic letters 3.16 (2001): 2571-2573.

Reddy, BVS, et al. "A novel self-terminated Prins strategy for the synthesis of tetrahydropyran-4-one derivatives and their behaviour in Fisher indole synthesis." RSC advances 6.79 (2016): 75133-75137.

Skubi, K. et al. "Dual catalysis strategies in photochemical synthesis." Chemical reviews 116.17 (2016): 10035-10074.

Smith III, A. B., et al. "Gram-scale synthesis of (+)-spongistatin 1: development of an improved, scalable synthesis of the F-ring subunit, fragment union, and final elaboration." Organic letters 10.19 (2008): 4359-4362.

Sun, S., et al. "Highly enantioselective catalytic cross-dehydrogenative coupling of N-carbamoyl tetrahydroisoquinolines and terminal alkynes." Organic letters 17.7 (2015): 1684-1687.

Tan, Y, et al. "Aerobic Asymmetric Dehydrogenative Cross-Coupling between Two C? H Groups Catalyzed by a Chiral-at-Metal Rhodium Complex." Angewandte Chemie International Edition 54.44 (2015): 13045-13048.

Tenenbaum, J. M., et al. "Synthesis of (−)-Okilactomycin by a Prins-Type Fragment-Assembly Strategy." Angewandte Chemie International Edition 50.26 (2011): 5892-5895.

Fu, W., et al. "Diastereoselective Tetrahydropyrone Synthesis through Transition-Metal-Free Oxidative Carbon-Hydrogen Bond Activation." Angewandte Chemie International Edition 47.22 (2008): 4184-4187.

(56) References Cited

OTHER PUBLICATIONS

Tucker, J. W., et al. "Oxidative photoredox catalysis: mild and selective deprotection of PMB ethers mediated by visible light." Chemical Communications 47.17 (2011): 5040-5042.

* cited by examiner

O1-Cu-N1-C1: dihedral∠ +30.2°

O2-Cu-N2-C2: dihedral∠ +35.9°

C1'-C2' length fixed to 2.2 Å

Caculated structure (PM3) of L3·Cu(II) with 1a/DDQ intermediate

O1-Cu-N1-C1: dihedral∠ +30.2°

O2-Cu-N2-C2: dihedral∠ +35.9°

Caculated structure (PM3) of L3•Cu(II)(H₂O)₂

ENANTIOSELECTIVE CROSS DEHYDROGENATIVE COUPLING REACTIONS AND COMPOUNDS SYNTHESIZED BY THE REACTIONS

CROSS-REFERENCE TO RELATED PATENT APPLICATIONS

The present application claims the benefit of priority under 35 U.S.C. § 119(e) to U.S. Provisional Patent Application No. 62/778,016, filed on Dec. 11, 2018, which content is incorporated herein by reference in its entirety.

BACKGROUND

The field of the invention relates to tetrahydropyran compounds and methods for synthesizing tetrahydropyran compounds. In particular, the field of the invention relates to enantioselective cross dehydrogenative coupling reactions for synthesizing tetrahydropyran compounds Tetrahydropyrans (THPs) are key structural elements in numerous bioactive natural products and medicinally relevant compounds.[1] Due to the prevalence of THPs, multiple stereoselective processes have been developed for their construction, including Prins cyclizations,[2] hetero-Diels-Alder reactions,[3] and intramolecular nucleophilic conjugate additions.[4] Established methods to construct THPs in an enantioselective fashion typically focus on conjugate additions[5] or activation by enamine/iminium intermediates,[6] two approaches that are deployed extensively in total synthesis. Inspired by natural product targets of interest in our laboratory, as well as small molecules possessing intriguing biological activity, we envisioned a complementary and direct method for the enantioselective synthesis of substituted tetrahydropyran-4-ones. The inventors have disclosed the use of β-hydroxy dioxinones as nucleophiles with aldehydes and isatins to undergo mild and stereoselective cyclizations in the presence of catalytic Lewis or Brønsted acids to access enantioenriched THPs.[7] The inventors' efforts in this area have enabled total syntheses of various natural products including exiguolide,[8] neopeltolide,[9] okilactomycin,[10] and other naturally occurring compounds containing THPs.[11] Conceptually, moving beyond preformed nucleophiles such as dioxinones to simple β-ketoester systems presents opportunities for enantiocontrol, most likely through two-point/chelate binding, but also requires different activation modes to operate simultaneously in a single reaction flask.

Here, the inventors disclose an enantioselective cross-dehydrogenative coupling (CDC) reaction which may be utilized to prepare tetrahydropyrans and derivatives thereof. The disclosed CDC reaction combines in situ Lewis acid activation of a nucleophile together with the oxidative formation of a transient oxocarbenium electrophile, which leads to a productive and highly enantioselective CDC reaction. The disclosed CDC reaction represents one of the first successful applications of CDC for the enantioselective couplings of unfunctionalized ethers. The disclosed CDC reactions may be utilized to access valuable tetrahydropyran motifs found in many natural products and bioactive small molecules.

SUMMARY

Disclosed are enantioselective cross dehydrogenative coupling reactions for synthesizing tetrahydropyran compounds. Novel tetrahydropyran compounds may be synthesized by the disclosed methods as well as tetrahydropyran precursor compounds for synthesizing various naturally occurring compounds. The enantioselective cross dehydrogenative coupling reactions utilize in situ Lewis Acid activation in combination with oxidative formation of an oxocarbenium ion to provide a highly efficient and selective coupling reaction for synthesizing tetrahydropyran compounds.

DETAILED DESCRIPTION

Figure 1:
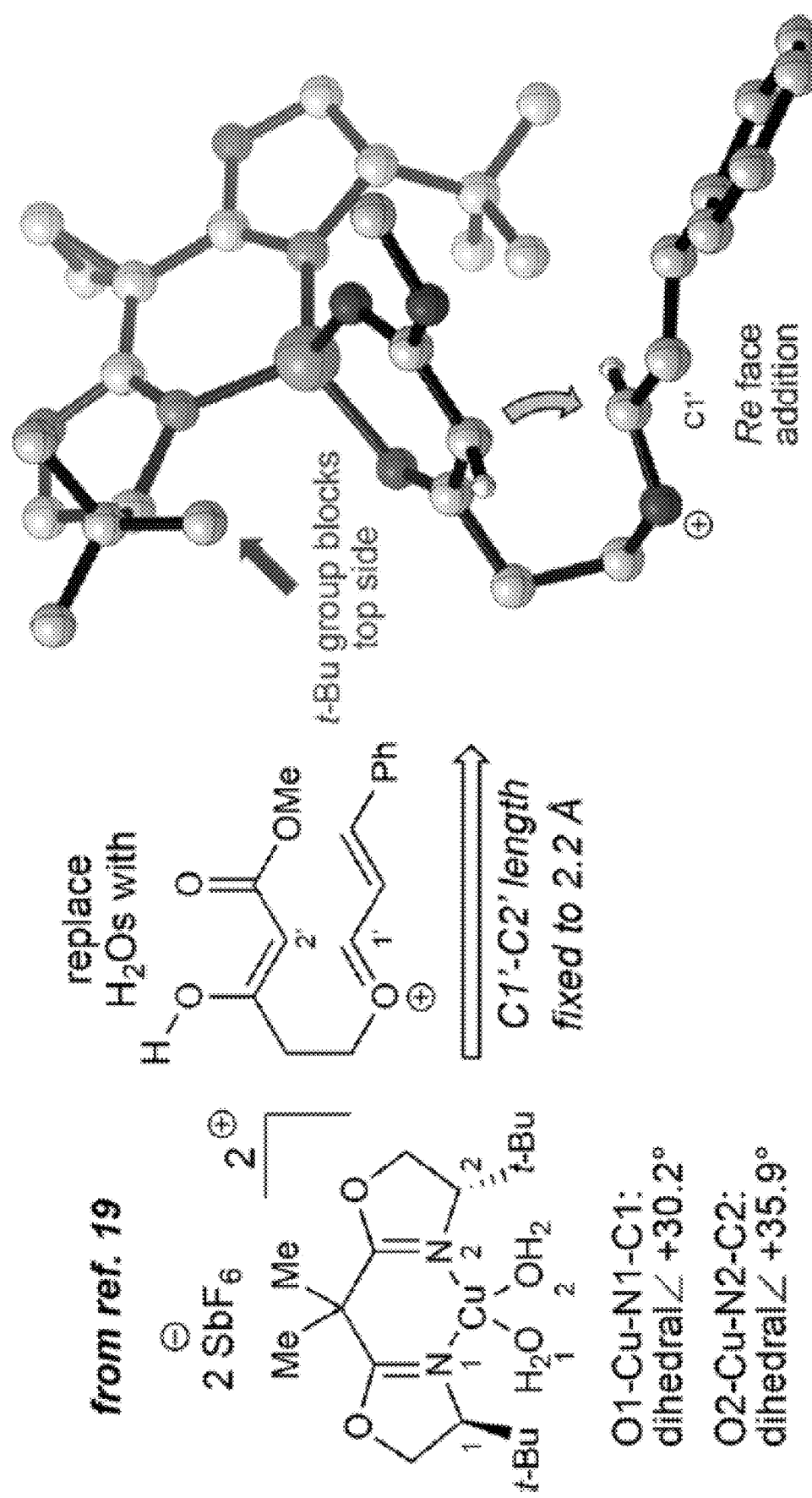
FIG. 1. Stereochemical induction model with 1a/(2,3-dichloro-5,6-dicyano-p-benzoquinone (DDQ) intermediate.
Figure 2:
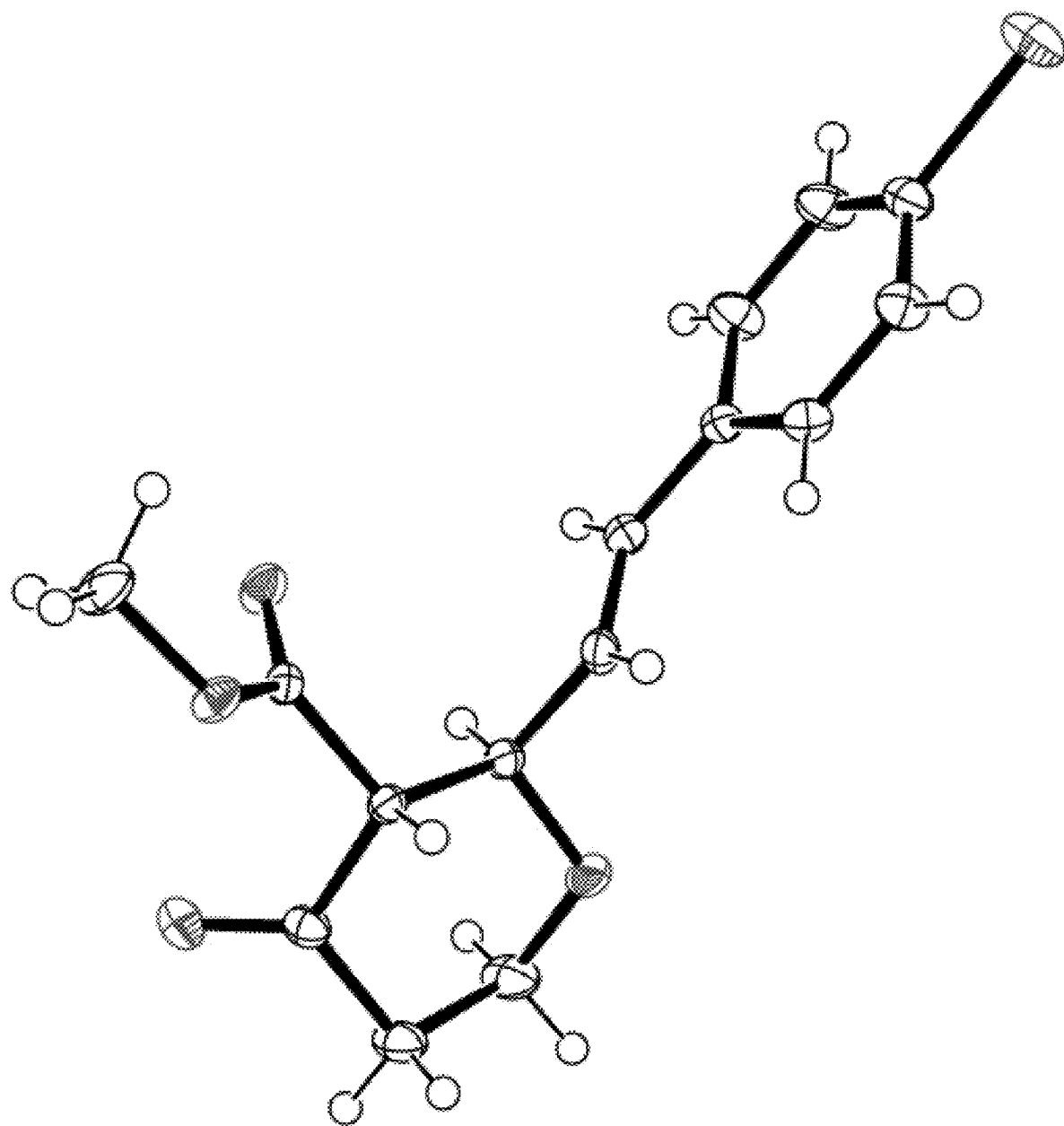
FIG. 2. ORTEP representation (50% probability) of the crystal structure of 2b.

The disclosed subject matter further may be described utilizing terms as defined below.

Unless otherwise specified or indicated by context, the terms "a", "an", and "the" mean "one or more." For example, "a compound" should be interpreted to mean "one or more compounds."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

New Chemical Entities and Methods of Synthesis

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., $-(CH_2)_n-$ where n is an integer such as an integer between 1 and 20). An exemplary alkylene group is $-CH_2CH_2-$.

The term "haloalkyl" refers to an alkyl group that is substituted with at least one halogen. For example, —CH$_2$F, —CHF$_2$, —CF, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyi, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CFB, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Enantioselective Cross Dehydrogenative Coupling Reactions and Compounds Synthesized the Reactions The subject matter of the application relates to enantioselective cross dehydrogenative coupling reactions for synthesizing tetrahydropyran compounds. Novel tetrahydropyran compounds may be synthesized by the disclosed methods as well as tetrahydropyran precursor compounds for synthesizing various natural occurring compounds.

In some embodiments, the disclosed compounds may have Formula I or a tautomer thereof:

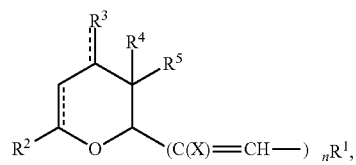

I where:
X is hydrogen or alkyl (e.g. methyl);
n is 0-6;
$R^1$ is hydrogen, alkyl, cycloalkyl, heterocycloalkyl, or aryl, optionally wherein $R^1$ is a single 5-membered or 6-membered ring or two or more fused 5-membered or 6-membered rings, wherein the single ring or two or more fused rings are carbocyclic or heterocyclic rings containing one or more heteroatoms selected from N, O, and S, and wherein the ring or two or more fused rings are saturated or unsaturated at one or more bonds, optionally wherein the single ring or more fused rings are substituted at one or more positions with a substituent selected from alkyl, alkoxy, halo, amino, and cyano;
$R^2$ is hydrogen, alkyl, aryl,

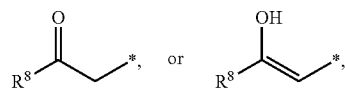

wherein $R^8$ is hydrogen, alkyl, or aryl;
$R^3$ is hydrogen, hydroxyl, or oxo;
$R^4$ is hydrogen or alkyl; and
$R^5$ is hydrogen or

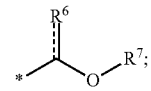

$R^6$ is hydrogen, hydroxyl, or oxo; and
$R^7$ is hydrogen or alkyl.

In some embodiments of the disclosed compounds, n is 0-2 and $R^1$ is selected from phenyl (optionally substituted at one or more positions with alkyl, alkoxy (e.g., 4-methoxy, 3,4-dimethoxy, or 3,4,5-trimethoxy), halo, or haloalkyl (e.g., trifluoromethyl)), naphthyl (e.g., naphth-1-yl or naphtha-2-yl), indolyl (e.g., indol-3-yl), thiazolyl (e.g., thiazol-2-yl).

In some embodiments, disclosed compounds may have a formula selected from:

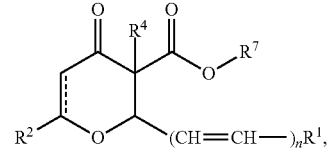

I(a)

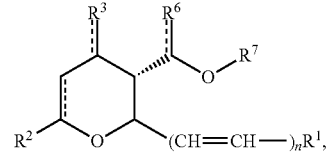

I(b)

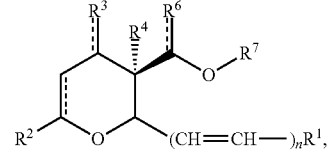

I(c)

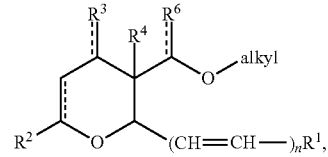

I(d)

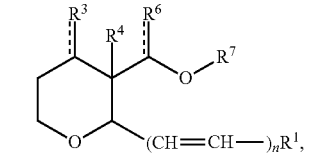

I(e)

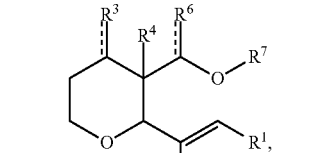

I(f)

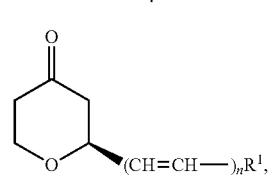

I(g)

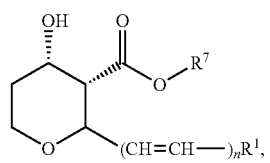 I(h)
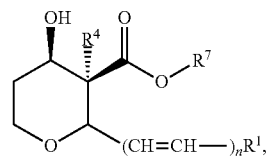 I(i)
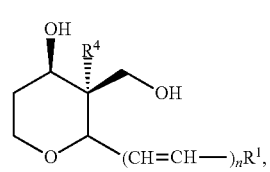 I(j)
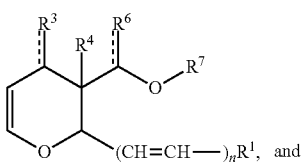 I(k)
and
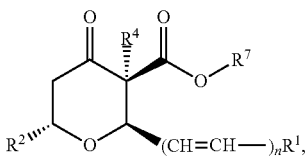 I(l)
In some embodiments, the disclosed compounds may have a formula selected from:
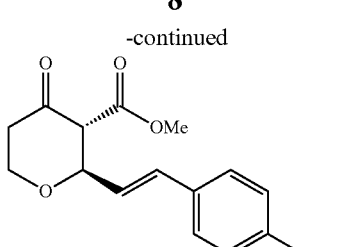,
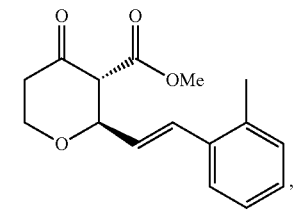,
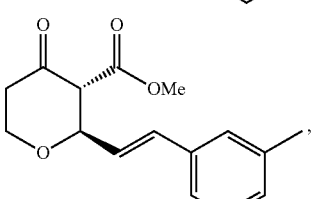,
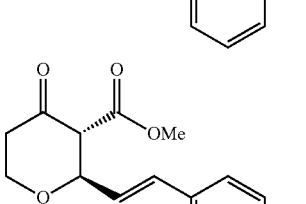,
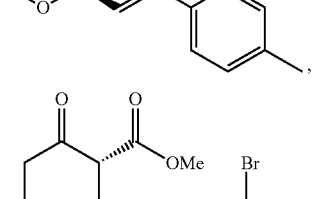,
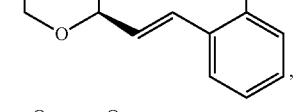,
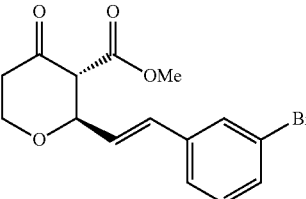,
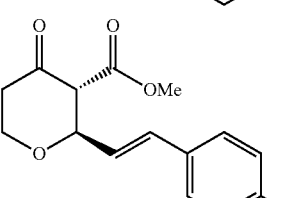,
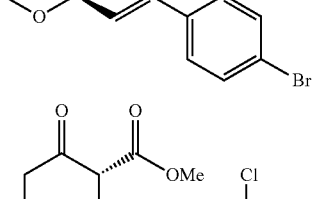,
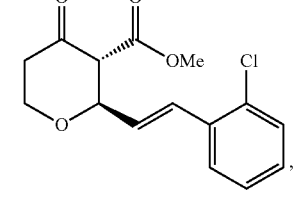,

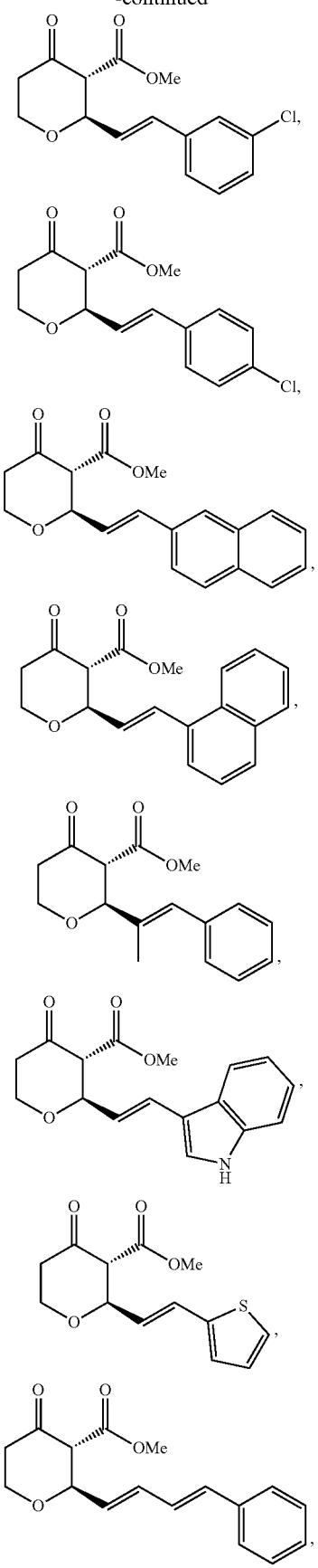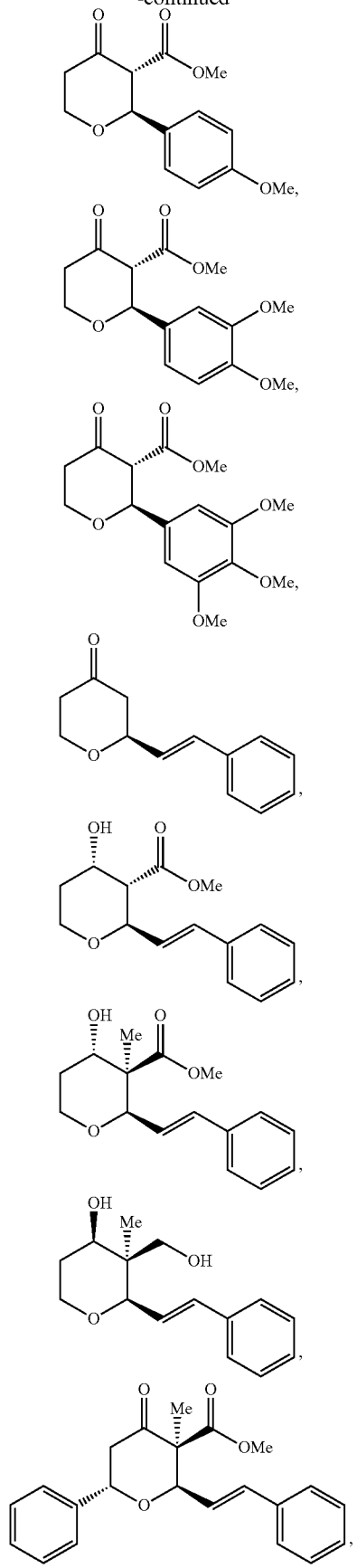

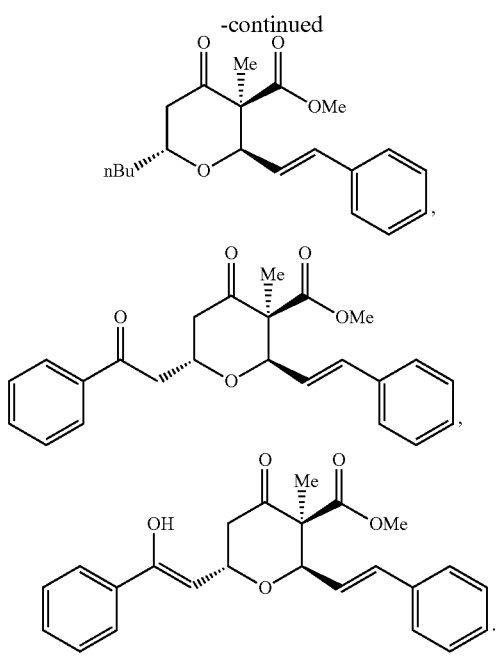

In some embodiments, the disclosed compounds may be utilized, for example as precursors, to prepare naturally occurring or man-made products. Naturally occurring products that may be prepared using the disclosed compounds include, but are not limited to exiguolide, neopeltolide, and okilactomycin and other compounds that contain tetrahydropyrans. (See, e.g., Crane, E. A.; Zabawa, T. P.; Farmer, R. L.; Scheidt, K. A. Angew. Chem. Int. Ed. 2011, 50, 9112-9115; Custar, D. W.; Zabawa, T. P.; Hines, J.; Crews, C. M.; Scheidt, K. A. J. Am. Chem. Soc. 2009, 131, 12406-12414; Custar, D. W.; Zabawa, T. P.; Scheidt, K. A. J. Am. Chem. Soc. 2008, 130, 804-805; Tenenbaum, J. M.; Morris, W. J.; Custar, D. W.; Scheidt, K. A. Angew. Chem. Int. Ed. 2011, 50, 5892-5895; Lee, K.; Kim, H.; Hong, J. Org. Lett. 2011, 13, 2722-2725; Lee, K.; Kim, H.; Hong, J. Angew. Chem. Int. Ed. 2012, 51, 5735-5738; Han, X.; Peh, G.; Floreancig, P. E. Eur. J. Org. Chem. 2013, 2013, 1193-1208; and Nasir, N. M.; Ermanis, K.; Clarke, P. A. Org. Biomol. Chem. 2014, 12, 3323-3335; the contents of which are incorporated herein by reference in their entireties.

In some embodiments, the disclosed compounds or pharmaceutical salts or hydrates thereof may be formulated as pharmaceutical composition. For example, the disclosed compounds or pharmaceutical salts or hydrates thereof may be formulated together with a pharmaceutical carrier to prepare a pharmaceutical composition.

Also disclosed herein are novel complexes. In some embodiments, the disclosed complexes have a formula represented as L·M$^{2+}$(OTf)$_2$, wherein M is a divalent metal such as Cu(II), Tf is triflyl, and L has a formula:

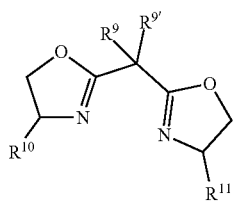

where R$^9$ and R$^{9'}$ together form a 3-membered, 4-membered, 5-membered, or 6-membered carbocyclic ring; and R$^{10}$ and R$^{11}$ are alkyl (e.g., n-butyl).

In some embodiments of the disclosed complexes, L may have a formula selected from:

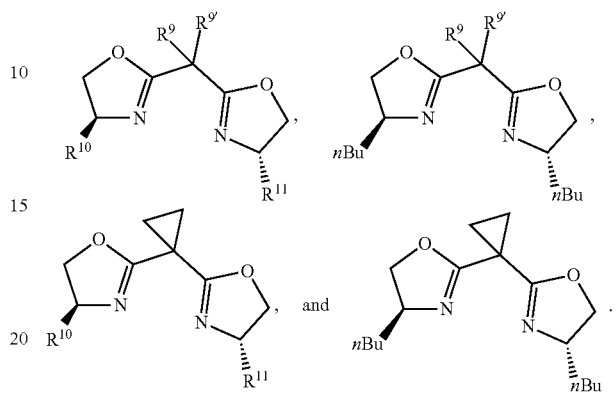

The compounds disclosed herein may be prepared by methods that include, but are not limited to a method comprising reacting a mixture comprising:
(a) a compound having a formula

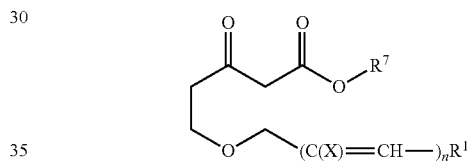

wherein:
X is hydrogen or alkyl (e.g. methyl);
n is 0-6;
R$^1$ is hydrogen, alkyl, cycloalkyl, heterocycloalkyl, or aryl, optionally wherein R$^1$ is a single 5-membered or 6-membered ring or two or more fused 5-membered or 6-membered rings, wherein the single ring or two or more fused rings are carbocyclic or heterocyclic rings containing one or more heteroatoms selected from N, O, and S, and wherein the ring or two or more fused rings are saturated or unsaturated at one or more bonds, optionally wherein the single ring or more fused rings are substituted at one or more positions with a substituent selected from alkyl, alkoxy, halo, amino, and cyano; and
R$^7$ is hydrogen or alkyl;
(b) a complex having a formula L·M$^{2+}$(OTf)$_2$, wherein M is a divalent metal (e.g., such as Cu(II)), Tf is triflyl, and L has a formula:

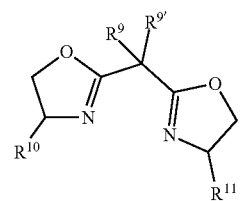

wherein $R^9$ and $R^{9'}$ are independently selected from alkyl, phenyl, or $R^9$ and $R^{9'}$ together form a 3-membered, 4-membered, 5-membered, or 6-membered carbocylic ring; and $R^{10}$ and $R^{11}$ are alkyl (e.g., n-butyl);

optionally wherein L has a formula selected from:

(c) an oxidant (optionally wherein the oxidant is (2,3-dichloro-5,6-dicyano-p-benzoquinone (DDQ)); and optionally (d) a salt (optionally wherein the salt is a sodium salt such as a sodium phosphate salt such as disodium phosphate).

In some embodiments of the disclosed reactions, the reaction mixture may be prepared using a solvent. Suitable solvents may include but are not limited to halogenated alkanes such as dichloromethane.

In some embodiments of the disclosed reactions, the reaction may be performed at a relatively low temperature. Suitable temperatures for performing the disclosed reactions may include temperatures of less than about 0, −10, −20, −30, −40, −50, −60, −70, −80, −90, or −100° C. or a temperature range bounded by any of these values (e.g., −50-−90° C.).

In some embodiments of the disclosed reactions, the reaction may be performed utilizing a molecular sieve (MS). In some embodiments, the MS has an average effective pore diameter of less than about 20, 10, 8, 6, 4, or 2 angstroms (Å) or a diameter range bounded by any of these values (e.g., 2-6 Å).

As noted, the compounds disclosed herein may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, 99% or 100% pure stereoisomer, epimer, or enantiomer.) As used herein, formulae which do not specify the orientation at one or more chiral centers are meant to encompass all orientations and mixtures thereof.

ILLUSTRATIVE EMBODIMENTS

The following embodiments are illustrative and should not be interpreted to limit the scope of the claimed subject matter.

Embodiment 1. A compound having Formula I or a tautomer thereof:

I wherein:

X is hydrogen or alkyl (e.g. methyl);

n is 0-6;

$R^1$ is hydrogen, alkyl, cycloalkyl, heterocycloalkyl, aryl, or heteroaryl, optionally wherein $R^1$ is a single 5-membered or 6-membered ring or two or more fused 5-membered or 6-membered rings, wherein the single ring or two or more fused rings are carbocyclic or heterocyclic rings containing one or more heteroatoms selected from N, O, and S, and wherein the ring or two or more fused rings are saturated or unsaturated at one or more bonds, optionally wherein the single ring or more fused rings are substituted at one or more positions with a substituent selected from alkyl, alkoxy, halo, amino, and cyano;

$R^2$ is hydrogen, alkyl, aryl, wherein $R^8$ is hydrogen, alkyl, or aryl;

$R^3$ is hydrogen, hydroxyl, or oxo;

$R^4$ is hydrogen or alkyl;

$R^5$ is hydrogen or $R^6$ is hydrogen, hydroxyl, or oxo; and $R^7$ is hydrogen or alkyl.

Embodiment 2. The compound of embodiment 1 having a Formula I(a) or a tautomer thereof:

I(a)

Embodiment 3. The compound of embodiment 1 having a Formula I(b) or a tautomer thereof:

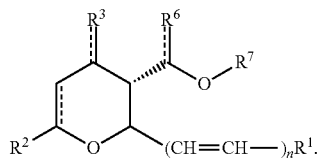
I(b)

Embodiment 4. The compound of embodiment 1 having a Formula Ic or a tautomer thereof:

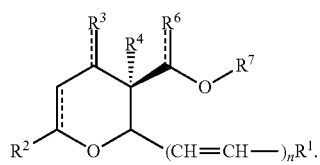
I(c)

Embodiment 5. The compound of embodiment 1 having a Formula Id or a tautomer thereof:

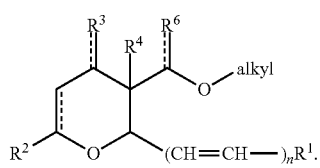
I(d)

Embodiment 6. The compound of embodiment 1 having a Formula I(e) or a tautomer thereof:

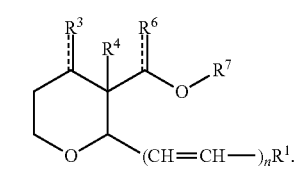
I(e)

Embodiment 7. The compound of embodiment 1, wherein n is 0-2 and $R^1$ is selected from phenyl (optionally substituted at one or more positions with alkyl, alkoxy (e.g., 4-methoxy, 3,4-dimethoxy, or 3,4,5-trimethoxy), halo, or haloalkyl (e.g., trifluoromethyl)), naphthyl (e.g., naphth-1-yl or naphtha-2-yl), indolyl (e.g., indol-3-yl), and thiazolyl (e.g., thiazol-$^2$-yl).

Embodiment 8. The compound of embodiment 1 having a Formula I(f) or a tautomer thereof:

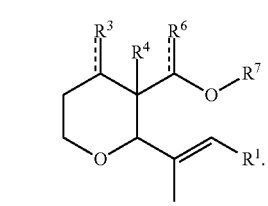
I(f)

Embodiment 9. The compound of embodiment 1 having a Formula I(g) or a tautomer thereof:

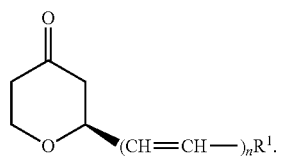
I(g)

Embodiment 10. The compound of embodiment 1 having a Formula I(h) or a tautomer thereof:

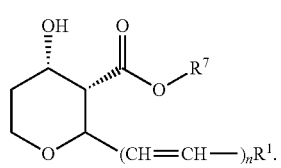
I(h)

Embodiment 11. The compound of embodiment 1 having a Formula I(i) or a tautomer thereof:

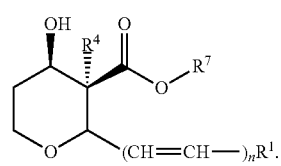
I(i)

Embodiment 12. The compound of embodiment 1 having a Formula I(j) or a tautomer thereof:

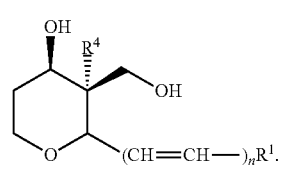
I(j)

Embodiment 13. The compound of embodiment 1 having a Formula I(k) or a tautomer thereof:

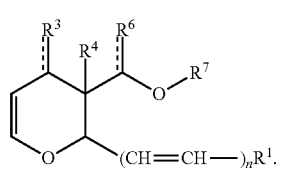
I(k)

Embodiment 14. The compound of embodiment 1 having a Formula I(l) or a tautomer thereof:

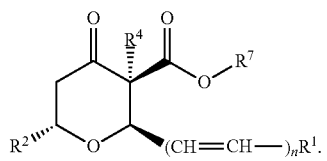
I(1)
Embodiment 15. The compound of any of the foregoing embodiments having a formula selected from:
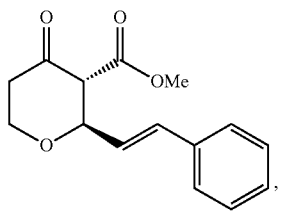
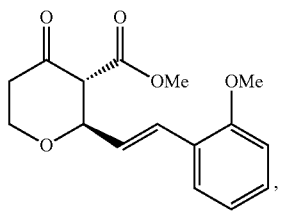
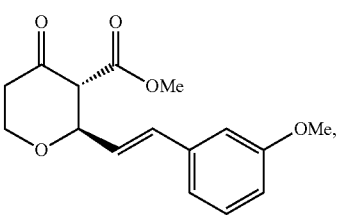
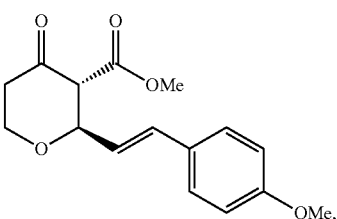
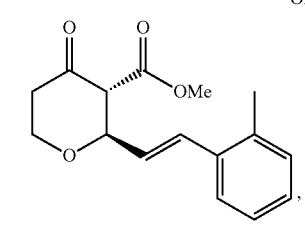
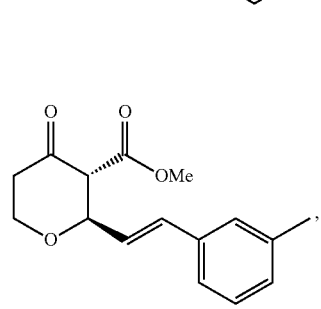
-continued
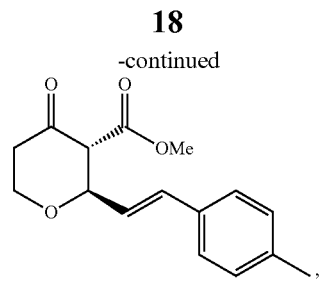
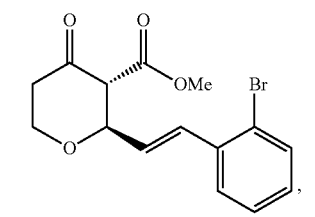
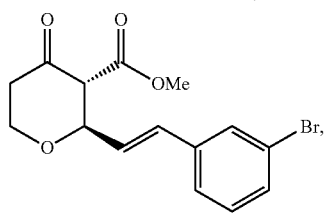
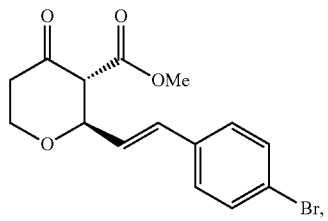
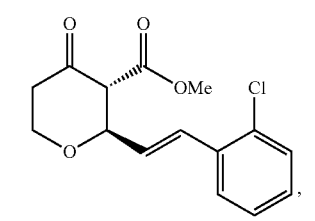
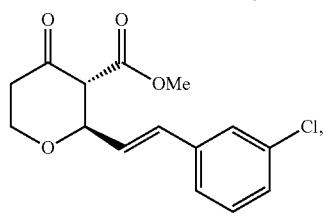
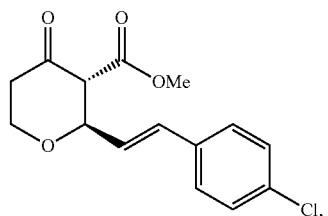
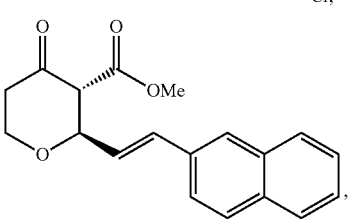

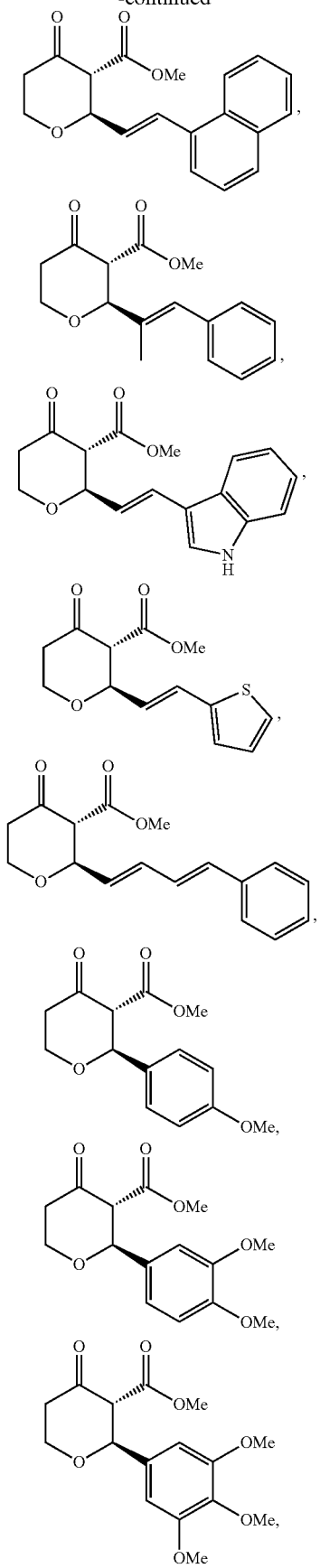
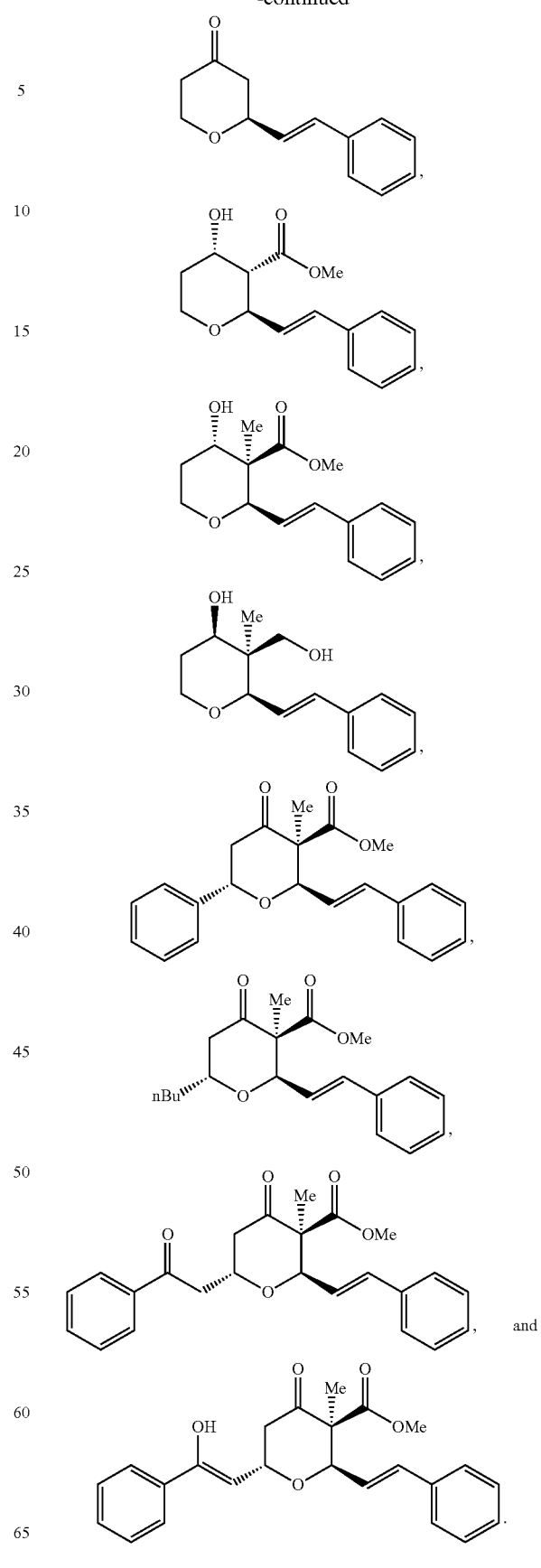

Embodiment 16. A pharmaceutical composition comprising any of the compounds of the foregoing embodiments or a pharmaceutical salt or hydrate thereof together with a pharmaceutical carrier.

Embodiment 17. A complex having a formula represented as $L \cdot M^{2+}(OTf)_2$, wherein M is a divalent metal (e.g., Cu(II)), Tf is triflyl, and L has a formula:

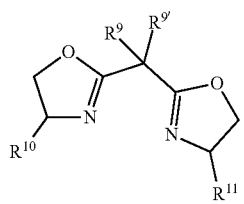

Wherein:
$R^9$ and $R^{9'}$ together form a 3-membered, 4-membered, 5-membered, or 6-membered carbocyclic ring; and
$R^{10}$ and $R^{11}$ are alkyl (e.g., n-butyl).

Embodiment 18. The complex of embodiment 17, wherein L has a formula:

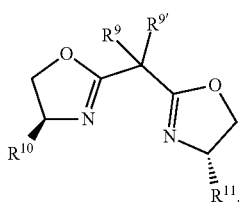

Embodiment 19. The complex of embodiment 17, wherein L has a formula:

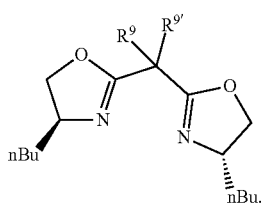

Embodiment 20. The complex of embodiment 17, wherein L has a formula:

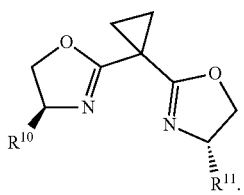

Embodiment 21. The complex of embodiment 17, wherein L has a formula:

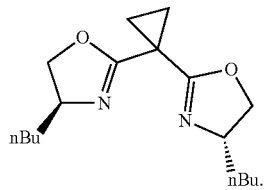

Embodiment 22. A method for preparing any of the compounds of embodiments 1-15, the method comprising reacting a mixture comprising:
(a) a compound having a formula

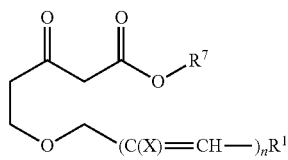

wherein:
X is hydrogen or alkyl (e.g. methyl)
n is 0-6;
$R^1$ is hydrogen, alkyl, cycloalkyl, heterocycloalkyl, aryl, or heteroaryl, optionally wherein $R^1$ is a single 5-membered or 6-membered ring or two or more fused 5-membered or 6-membered rings, wherein the single ring or two or more fused rings are carbocyclic or heterocyclic rings containing one or more heteroatoms selected from N, O, and S, and wherein the ring or two or more fused rings are saturated or unsaturated at one or more bonds, optionally wherein the single ring or more fused rings are substituted at one or more positions with a substituent selected from alkyl, alkoxy, halo, amino, and cyano; and
$R^7$ is hydrogen or alkyl;
(b) a complex having a formula $L \cdot M^{2+}(OTf)_2$, wherein M is a divalent metal, Tf is triflyl, and L has a formula:

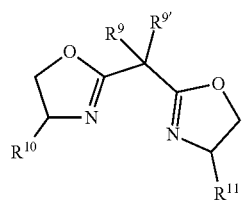

wherein:
$R^9$ and $R^{9'}$ are independently selected from alkyl, phenyl, or $R^9$ and $R^{9'}$ together form a 3-membered, 4-membered, 5-membered, or 6-membered carbocylic ring; and
$R^{10}$ and $R^{11}$ are alkyl (e.g., n-butyl);
optionally wherein the complex is the complex of any of embodiments 16-20;
(c) an oxidant (optionally wherein the oxidant is (2,3-dichloro-5,6-dicyano-p-benzoquinone (DDQ)); and optionally
(d) a salt (optionally wherein the salt is a sodium salt such as a sodium phosphate salt such as disodium phosphate).

EXAMPLES

The followings Examples are illustrative only and should not be interpreted to limit the scope of the claimed subject matter.

Example 1

Title—Enantioselective Cross Dehydrogenative Coupling Reactions

Technical Field

The technical field of the disclosed subject matter relates to enantioselective cross dehydrogenative coupling (CDC) reactions and the use of the enantioselective CDC reactions for preparing compounds such as tetrahydropyrans and derivatives thereof.

Abstract

The inventors have developed an enantioselective cross-dehydrogenative coupling (CDC) reaction which may be utilized to prepare tetrahydropyrans and derivatives thereof. The disclosed CDC reaction combines in situ Lewis acid activation of a nucleophile together with the oxidative formation of a transient oxocarbenium electrophile, which leads to a productive and highly enantioselective CDC reaction. The disclosed CDC reaction represents one of the first successful applications of CDC for the enantioselective couplings of unfunctionalized ethers. The disclosed CDC reactions may be utilized to access valuable tetrahydropyran motifs found in many natural products and bioactive small molecules.

Applications

The applications of the disclosed technology include, but are not limited to: (i) access to tetrahydropyran motifs found in many natural product and bioactive small molecules; and (ii) expansion of synthetic technology into different catalytic manifolds, for example, by using similar chemical set-ups as disclosed herein of different chemical structural classes to provided different product scaffolds.

Advantages

The advantages of the disclosed technology include, but are not limited to: (i) the disclosed technology allows for the use of unfunctionalized starting materials to access the core structural motif focused on in this work (i.e. pyrans); (ii) the disclosed technology is easy to implement into a standard chemical workflow (i.e., no specialized equipment is necessary for others to practice the disclosed technology); and (iii) the disclosed technology can be used to prepare diverse chemical products in ways that have not been previously reported or extensively explored.

Brief Summary of the Technology

The technology relates to enantioselective cross-dehydrogenative coupling (CDC) reactions that utilize in situ Lewis Acid activation in combination with oxidative formation of an oxocarbenium ion to provide a highly efficient and selective coupling reaction. The technology further is disclosed in Example 2 below and in Lee et al., "An Enantioselective Cross-Dehydrogenative Coupling Catalysis Approach to Substituted Tetrahydropyrans," J. Am. Chem. Soc. 2018, 140, 6212-6216; the content of which is incorporated herein by reference in its entirety.

Technical Description

Using catalytic amounts of a chiral Cu(II)-Box complex in combination with an organic oxidant (2,3-dichloro-5,6-dicyano-p-benzoquinone (DDQ)), which was added dropwise via a syringe pump, we have demonstrated the enantioselective construction of pyranones from unfunctionalized ethers. The disclosed reaction is straightforward and simple to setup, where all of the necessary equipment should be found in a standard organic chemistry laboratory.

Others have tried using other catalyst manifolds to afford construction of similar chemical compounds. However, previous attempts have suffered from a lack of efficiency and only a small collection of chemical compounds that are compatible with the catalyst manifold.

Prior to the disclosure of this work, there were no concise and efficient methods to access pyrans from unfunctionalized starting materials. Pyrans are a common structural motif found in medicinally relevant natural products. With the disclosure of this work, the inventors have provided state-of-the-art technology to access these compounds.

Example 2

Reference is made to Lee et aL, "An Enantioselective Cross-Dehydrogenative Coupling Catalysis Approach to Substituted Tetrahydropyrans," J. Am. Chem. Soc. 2018, 140, 6212-6216, the content of which is incorporated herein by reference in its entirety.

TITLE—An Enantioselective Cross-Dehydrogenative Coupling Catalysis Approach to Substituted Tetrahydropyrans Abstract An enantioselective cross-dehydrogenative coupling (CDC) reaction to access tetrahydropyrans has been developed. This process combines in situ Lewis acid activation of a nucleophile in concert with the oxidative formation of a transient oxocarbenium electrophile, leading to a productive and highly enantioselective CDC. These advances represent one of the first successful applications of CDC for the enantioselective couplings of unfunctionalized ethers. This system provides efficient access to valuable THP motifs found in many natural products and bioactive small molecules.

Introduction

Tetrahydropyrans (THPs) are key structural elements in numerous bioactive natural products and medicinally relevant compounds,[1] Due to the prevalence of THPs, multiple stereoselective processes have been developed for their construction, including Prins cyclizations,[2] hetero-Diels-Alder reactions,[3] and intramolecular nucleophilic conjugate additions.[4] Established methods to construct THPs in an enantioselective fashion typically focus on conjugate additions[5] or activation by enamine/iminium intermediates,[6] two approaches that are deployed extensively in total synthesis. Inspired by natural product targets of interest in our laboratory, as well as small molecules possessing intriguing biological activity, we envisioned a complementary and direct method for the enantioselective synthesis of substituted tetrahydropyran-4-ones. We have disclosed the use of β-hydroxy dioxinones as nucleophiles with aldehydes and isatins to undergo mild and stereoselective cyclizations in the presence of catalytic Lewis or Brønsted acids to access enantioenriched THPs.[7] Our efforts in this area have enabled total syntheses of various natural products including exiguolide,[8] neopeltolide,[9] okilactomycin,[10] and other naturally occurring compounds containing THPs.[11] Conceptually, moving beyond preformed nucleophiles such as dioxinones to simple β-ketoester systems presents opportunities for enantiocontrol, most likely through two-point/chelate binding, but also requires different activation modes to operate simultaneously in a single reaction flask.

Cross-dehydrogenative coupling (CDC) reactions have emerged as powerful approaches to forge C—C bonds from inert C—H bonds.[12] As a subset of C—H functionalization processes,[13] CDC reactions are attractive because they do not require prefunctionalized starting materials, relying instead on oxidative activation followed by net loss of $H_2$ to facilitate C—C bond formation. Specifically, 2,3-dichloro-5,6-dicyano-1,4-benzoquinone (DDQ) a strong oxidizing agent, promotes the formation of stabilized carbocations by benzylic and allylic C—H bond activation, and subsequent C—C bond formation.[14] Mechanistically, DDQ mediated CDC reactions proceed via single electron transfer to form stabilized radical cations, followed by hydrogen atom abstraction to form the electrophilic coupling partner (e.g., oxocarbenium ion, iminium ion). Floreancig has effectively demonstrated that DDQ activation can facilitate racemic access to carbocycles and heterocycles via the oxidation of allylic ethers.[15] Although enantioselective CDC reactions have been reported during the last decade,[16] there is a dearth of highly enantioselective CDC reactions using oxocarbenium ion electrophiles in contrast to a plethora of enantioselective CDC reactions using iminium electrophiles (Scheme 1b).[17] A major challenge to this approach is successfully integrating strongly oxidative conditions for oxocarbenium ion formation (e.g., DDQ) with stereodefining catalysts necessary for nucleophile activation (e.g., chiral Lewis acids) to a) promote a productive reaction, and b) induce stereocontrol around a transient, highly reactive oxocarbenium ion. Here, we report an enantioselective CDC of β-ketoesters with oxocarbenium ions to access substituted tetrahydropyrans with high yields and enantioselectivity through a merged chiral Lewis acid/oxidation strategy (Scheme 1c).

Figure 5:
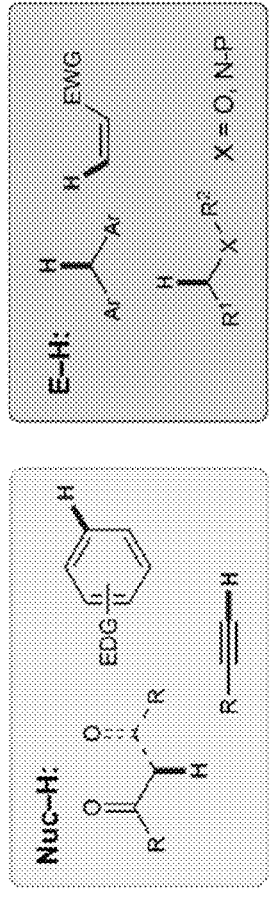
FIG. 5. CDC Processes and Reaction Design.
Figure 5:
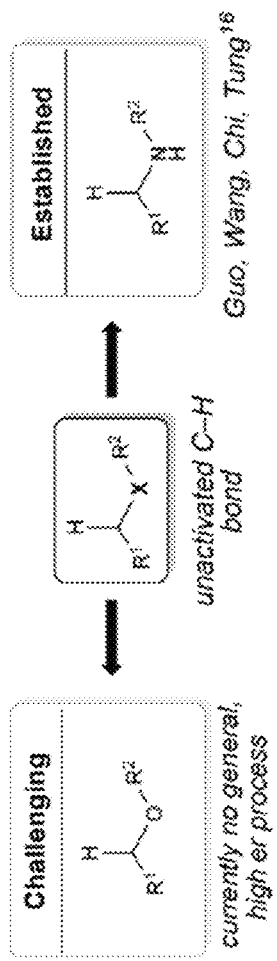
Figure 5:
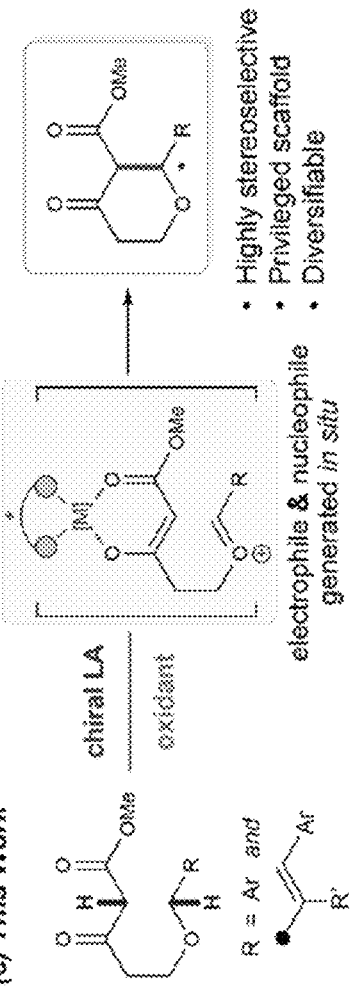

Scheme 1. CDC Processes and Reaction Design
(See FIG. 5)

Results and Discussion

We initiated our investigations of this chiral Lewis acid/ oxidant process using β-ketoester substrate 1a and found that Cu(II)-bisoxazoline (BOX) complex L1.Cu(OTt)$_2$ gave the desired product 2a as the sole diastereomer in 72% yield and 92:8 er at −70° C. (Scheme 2). Additional screening with chiral BOX ligands L2-L5 identified ligand L3 as optimal, furnishing 2a in 83% yield and 95:5 er upon further reaction dilution to 0.02 M.

Scheme 2. Ligand Screening for CDC Reactions

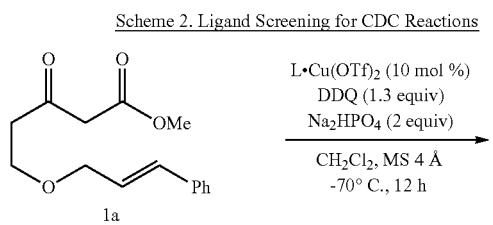

L·Cu(OTf)$_2$ (10 mol %)
DDQ (1.3 equiv)
Na$_2$HPO$_4$ (2 equiv)

CH$_2$Cl$_2$, MS 4 Å
−70° C., 12 h

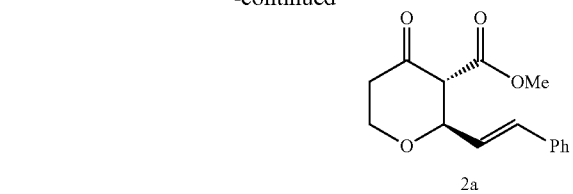

2a

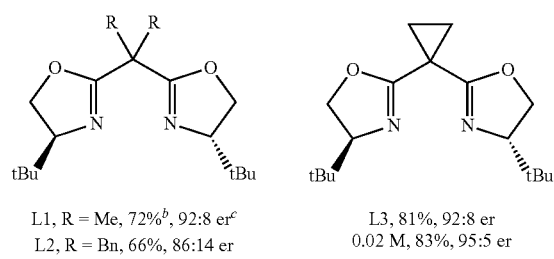

L1, R = Me, 72%[b], 92:8 er[c]
L2, R = Bn, 66%, 86:14 er

L3, 81%, 92:8 er
0.02 M, 83%, 95:5 er

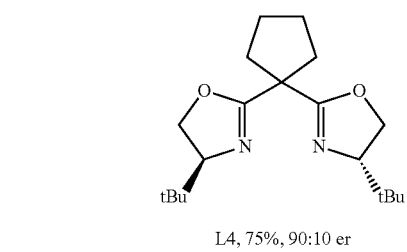

L4, 75%, 90:10 er

[a]The reactions were performed with 1a (0.2 mmol), L·Cu (OTf)$_2$ (10 mol %), DDQ (0.26 mmol), Na$_2$HPO$_4$ (0.4 mmol), and MS 4 Å (250 mg) in CH$_2$Cl$_2$ (0.04M). Absolute configuration of 2a was determined based on X-ray crystal analysis of 2 h.[18] [b]Yield of isolated product. [c]Determined by chiral-phase SFC analysis.

After optimization the basic asymmetric CDC reaction with β-ketoester in, the general scope was explored (Table 1). When the aromatic ring on the cinnamyl ether was substituted with electron-donating groups at its para, meta, or ortho position, the reactions provided desirable tetrahydropyran-4-ones 2c-2g in high yields and stereoselectivity with exception of 2b. We observed that substrate 1b possessing a p-methoxycinnamyl group produced side products due to over-oxidation. Furthermore, reaction of 1b without a Cu(II) catalyst produced rac-2b in 70% yield in only 1 hour, suggesting the competitive background reaction of this highly reactive substrate also contributed to the observed reduction in stereoselectivity.

TABLE 1

Substrate Scope of β-Keto Esters 1[a]

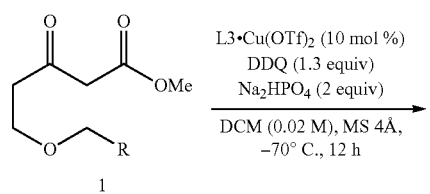

L3·Cu(OTf)$_2$ (10 mol %)
DDQ (1.3 equiv)
Na$_2$HPO$_4$ (2 equiv)

DCM (0.02 M), MS 4Å,
−70° C., 12 h

1

TABLE 1-continued
Substrate Scope of β-Keto Esters 1[a]
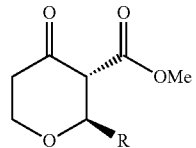
2
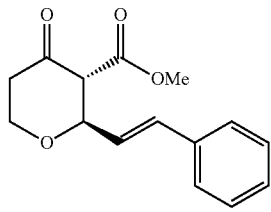
2a, 83%
95:5 er
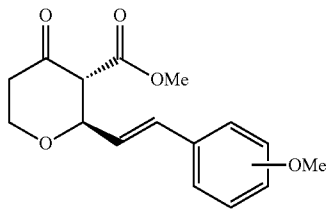
2b, p-MeO, 60%, 78:22 er
2c, m-MeO, 78%, 96:4 er
2d, o-MeO, 70%, 92:8 er
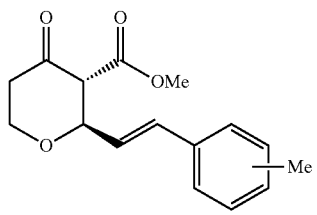
2e, p-Me, 84%, 95:5 er
2f, m-Me, 71%, 95:5 er
2g, o-Me, 81%, 96:4 er
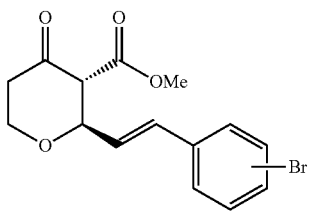
2h, p-Br, 59%, 94:6 er
2i, m-Br, 55%, 95:5 er
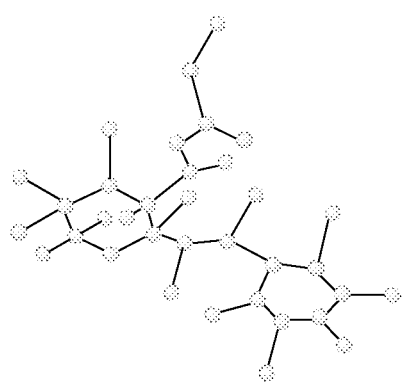
X-ray of 2h
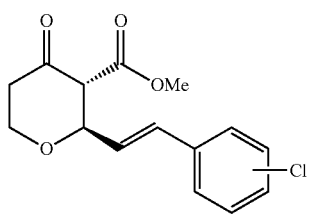
2j, m-Cl, 68%, 96:4 er
2k, o-Cl, 58%, 97:3 er
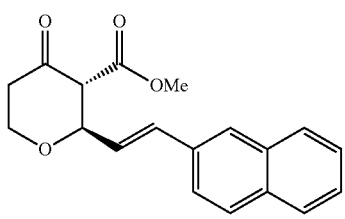
2l, 77%
94:6 er
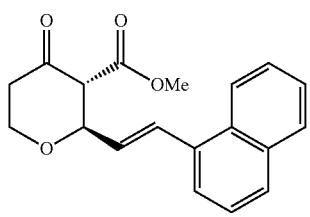
2m, 80%
95:5 er TABLE 1-continued Substrate Scope of β-Keto Esters 1[a]

2n, 87%
97:3 er 2o, 55%
87:13 er 2p, 69%
88:12 er 2q, 50%
91:9 er

2r[b], 20 h
50% 91:9 er

2s[b], 4 h
50% 89:11 er

2t[b], 45 h
56% 91:9 er

[a]See Materials and Methods below for reaction details. Er determined by chiral-phase SFC analysis. Products 2 were obtained with >20:1 dr (trans/cis).
[b]Performed at −30° C.

We then evaluated substrates substituted with electron-withdrawing groups at para, meta, and ortho positions. The reactions of 1h-1k provided desired products 2h-2k in moderate yields and high stereoselectivity. The results showed that high yields and stereoselectivity were observed for 1l and 1m containing naphthyl groups. The reaction of 1n containing a trisubstituted cinnamyl alkene afforded 2n in 87% yield and 97:3 er, while heteroaryl and conjugated ethers 1o-1q gave tetrahydropyran-4-ones 2o-2q in somewhat decreased yields and stereoselectivities. A survey of benzyl ethers revealed that only 4-methoxy-substituted substrates 1r-1t were capable of producing desired products 2r-2t with high stereoselectivity and moderate yield. Under the current conditions, we have not observed productive reactions using propargylic, unsubstituted allylic or ether substrates leading to tetrahydrofurans (i.e., 5 atom tether length). Instead, over-oxidation or no oxidation is observed (see Supp. Info.). However, with this successful proof of concept, investigations with various oxidation methods and Lewis acids to engage an even larger range of substrate classes are ongoing.

Attempts to access enantioenriched tetrahydropyran-4-ones without the β-ketoester were unsuccessful, as enol acetate 3 provided racemic 4 in 68% yield (Scheme 3a). This observation supports the hypothesis that the β-ketoester is crucial for stereoselectivity by coordination with the Cu(II)/BOX catalyst. In an attempt to probe whether an enantioselective intermolecular CDC reaction was possible, cinnamyl methyl ether was exposed to methyl acetoacetate in the presence of L3.Cu(OTf)$_2$ to afford 5 (Scheme 3b). Although the intermediate oxocarbenium ion could potentially undergo both 1,2- and 1,4-addition, the 1,2-addition adduct 5 was observed (as detected by NMR spectroscopy). Unfortunately, attempts to isolate 5 have been unsuccessful, due to facile elimination of the □-methoxy group to form enone 6 (2.7:1 E/Z mixture).

Scheme 3. CDC Reaction Extension (a) CDC Reaction of Enol Acetate 3

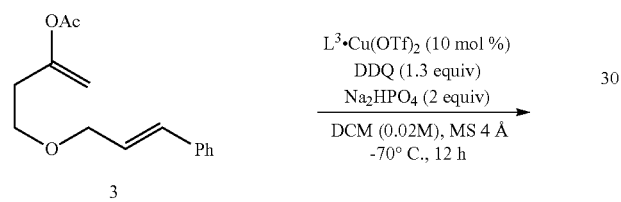

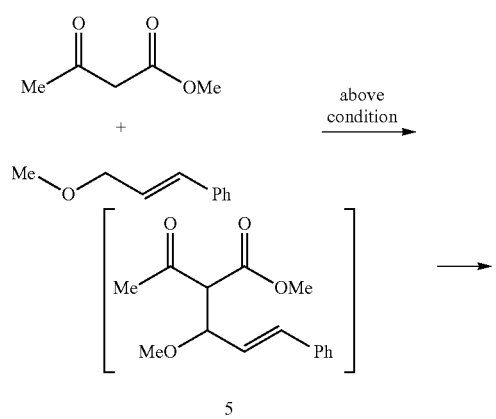

(c) CDC Reaction of α-Methyl-β-Keto Ester 1z

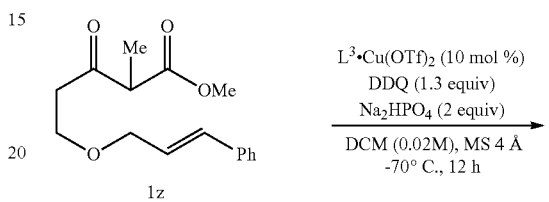

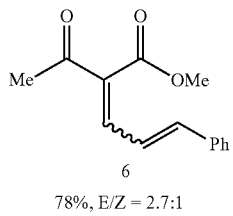

The stereochemical model of the reaction with 1a, Cu(II)/BOX and DDQ is based on a reported X-ray crystal structure of [L1.Cu(H$_2$O)$_2$](SbF$_6$)$_2$ by replacement of H$_2$O ligands with the oxocarbenium ion of 1a (FIG. 1).[19] With the oxidized substrate bound to the Cu(II) center via bidentate chelation, the bulky tert-butyl group of the L3.Cu(II) complex shields the top face of the bound substrate (Si face) which in turn places the transient oxocarbenium ion below. During the reaction, the metal-bound enol(ate) adds to the Re face of the oxocarbenium ion via a pseudo chair-like conformation to provide product 2a with S configuration at the C1' position, consistent with observed stereochemistry. This model also supports the observed relative C1'-C2' trans relationship of the products.

A practical advantage of this strategy is the ease of synthetically elaborating these β-keto esters (Scheme 4). Conventional heating in DMF/H$_2$O provided the decarboxylated product 4 in 77% yield, where methylation of 2a gave 3,3-disubstituted tetrahydropyran-4-one 7 in excellent yield with 13:1 dr. Exposure of β-ketoesters 2a or 7 to L-selectride provided the corresponding tetrahydropyran-4-ol 8 or 9, while LiAlH$_4$ reduction of 7 furnished diol 10.[20] Functionalization of the 6-position of the 7 has also been demonstrated. First, cyclic enone 11 was prepared via dehydrogenation using 1 atm of O2 in the presence of Pd(TFA)$_2$ in DMSO.[21] Rh(I)-catalyzed 1,4-addition of phenylboronic acid produced 12,[22] and conjugate addition of an alkyl cuprate provided 13 as the trans diastereomers in both reactions.[20,23] Lastly, Mukaiyama-Michael addition proceeded to afford 14 with 10:1 diastereomeric ratio.[23,24] Notably, while many synthetic methods exist for cis-2,6-tetrahydropyran structures,[25] there are far fewer preparations for trans-2,6-tetrahydropyrans.[26]

Scheme 4. Transformations of 2a

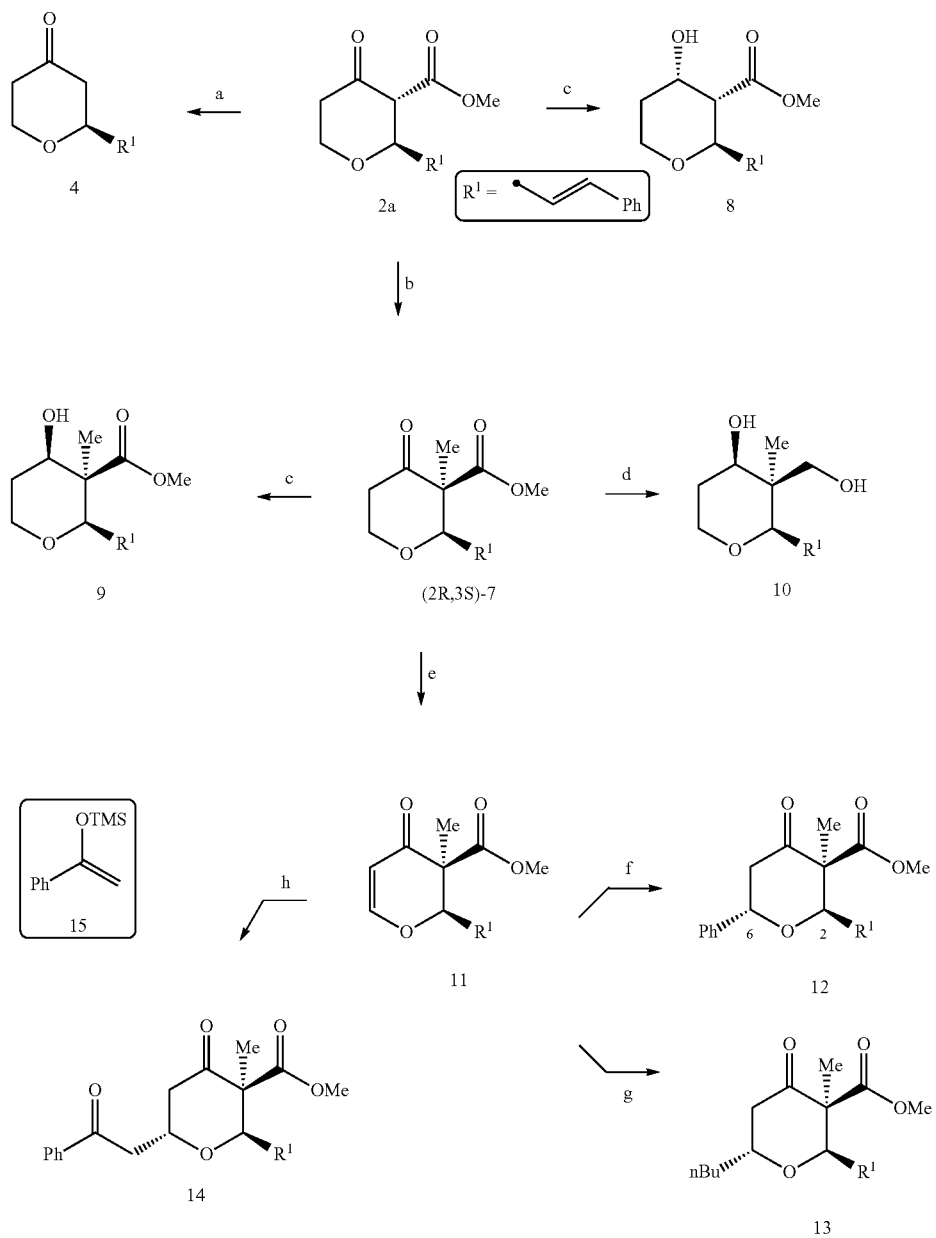

<sup>a</sup>Conditions: (a) DMF/H₂O, 130° C., 77% (b) MeI, NaH, 97%, 13:1 dr (c) L-selectride, 64% for 8, 71% for 9 (d) LiAlH4, 62% (e) Pd(TFA)₂, O₂, 67% (f) Rh(cod)₂BF₄, PhB(OH)₂, 75%, 20:1 dr (g) nBu₂CuLi, TMSCl, 76%, 20:1 dr (h) 15, InCl₃, 93%, 10:1 dr.

To substitute DDQ as a reagent, we investigated complementary oxidation processes to form the oxocarbenium ion. A recent report of photoredox catalysis being used to generate oxocarbenium ions[27] inspired us to leverage this approach and trap the oxocarbenium ion with our tethered carbon nucleophile. Gratifyingly, the use of Sc(OTf)₃, Ir[dF(CF₃)ppy]₂(dtbbpy)PF₆, blue LEDs, and bromochloroform provided access to rac-2a in 90% yield (Scheme 5). To date, these photoredox conditions are not yet compatible with various chiral ligands to induce enantioselectivity.28

Scheme 5. Photoredox-Catalyzed CDC Reaction

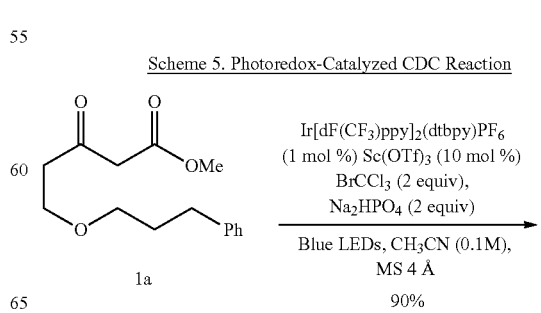

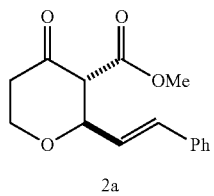

In summary, a chiral Lewis acid-catalyzed intramolecular cross-dehydrogenative coupling of β-ketoesters has been developed. This oxidative process utilizes unfunctionalized starting materials to provide chiral 2-substituted tetrahydropyrans with excellent yields and stereoselectivity. The in situ generation of both nucleophilic and electrophilic partners specifically provides new opportunities for enantioselective oxocarbenium ion-driven reactions and CDC processes in general. Investigations in our laboratory towards leveraging this chiral Lewis acid/oxidation system with new substrate classes as well as the use of visible light mediated oxidation in asymmetric transformations are currently underway.

Materials and Methods

1. General Information

All reactions were carried out under a nitrogen atmosphere in oven-dried glassware with magnetic stirring. All organic solvents were purified by passage through a bed of activated alumina. (See Pangborn, A. B.; Giardelo, M. A.; Grubbs, R. H.; Rosen, R. K.; Timmers, F. J. *Organomellics* 1996, 15, 1518). Purification of reaction products was carried out by flash chromatography using EM Reagent or Silicycle silica gel 60 (230-400 mesh). Analytical thin layer chromatography was performed on EM Reagent 0.25 mm silica gel 60-F plates. Visualization was accomplished with UV light and ceric ammonium nitrate stain, potassium permanganate stain or ninhydrin stain followed by heating. 1H NMR spectroscopy spectra were recorded on a Bruker Avance III 400 or 500 MHz w/direct cryoprobe (400 or 500 MHz) spectrometer and are reported in ppm using solvent as an internal standard ($CDCl_3$ at 7.26 ppm). Data are reported as (s=singlet, d=doublet, t=triplet, q=quartet, m=multiplet, br=broad; coupling constant(s) in Hz, integration). Proton-decoupled 13C NMR spectroscopy spectra were recorded on a Bruker Avance 500 MHz w/direct cryoprobe (125 MHz) spectrometer and are reported in ppm using solvent as an internal standard ($CDCl_3$ at 77.16 ppm). SFC analysis was performed on an Agilent 1290 Infinity, using Chiralpak IA-3, IB-3, IC-3, ID-3, and IG-3 columns. Mass spectra data were obtained on a Varian 1200 Quadrupole Mass Spectrometer and Micromass Quadro II Spectrometer or a WATERS Acquity-H UPLC-MS with a signel quad detector (ESI). $L.Cu(OTf)_2$ complexes were prepared according to literature procedures. (See Evans, D. A.; Peterson, G. S.; Johnson, J. S.; Barnes, D. M.; Campos, K. R.; Woerpel, K. A. *J. Org. Chem.* 1998, 63, 4541). Stereochemical models were optimized using the Spartan 08 program implement of semi-empirical PM3 calculation. (See Stewart, J. J. P. *J. Comput. Chem.* 1989, 10, 209).

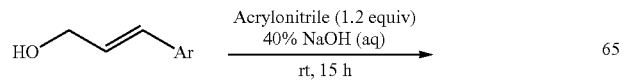

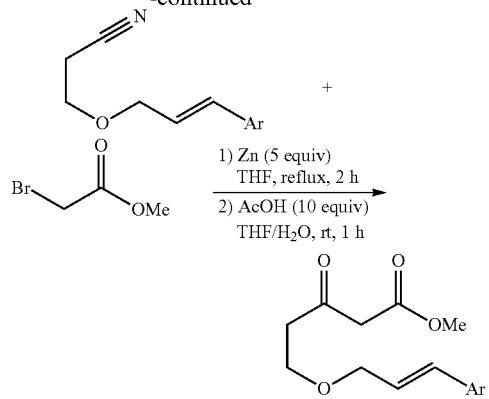

Acrylonitrile (0.39 mL, 6.0 mmol) was added to a mixture of the corresponding cinnamyl alcohol (5.0 mmol) and 50 μL of aqueous NaOH (40%) at room temperature (If the corresponding cinnamyl alcohol was solid, 2 mL of benzene or THF was added). The reaction mixture was stirred for 15 h at same temperature, then neutralized with aqueous HCl (1 N), and diluted with ethyl acetate. The organic layer was washed with 5% aqueous NaOH followed by brine, evaporated in vacuo, and dried thoroughly to afford the desired compound. The crude compound was used for the next steps without purification. (See Krishna, T. R.; Jayaraman, N, *J. Org. Chem.* 2003, 68, 9694).

To an oven dried 100 mL 3 neck round bottom flask equipped with a reflux condenser under $N_2$ was added a magnetic stir bar, Zinc (1.63 g, 25 mmol), and 15 mL of THF. The solution was heated to reflux, and then 0.25 mL of methyl bromoacetate was added slowly to activate the zinc (gray color to hunter green). Once the zinc was activated, the corresponding nitrile was added, followed by slow addition of 1.87 mL of methyl bromoacetate (20 mmol) over 1 h. The reaction stirred for 2 h, and was then removed from heat. The saturated $NaHCO_3$ solution was added to quench the reaction, followed by addition of diethyl ether. The heterogeneous solution was filtered over a pad of Celite with diethyl ether. The aqueous layer was extracted with diethyl ether, dried and concentrated in vacuo. The 2.86 mL of AcOH (50 mmol), 10 mL of THF, and 10 mL of $H_2O$ were added to the crude compound. The reaction stirred for 1 h at ambient temperature, and then saturated $NaHCO_3$ solution was added to quench the reaction. The aqueous layer was extracted with ethyl acetate, dried and concentrated in vacuo. The resulting residue was purified by column chromatography on silica gel (hexanes:EtOAc=4:1) to give the corresponding β-keto esters 1. (The β-keto esters 1 were isolated with the corresponding enol tautomer in 11:1 ratio.)

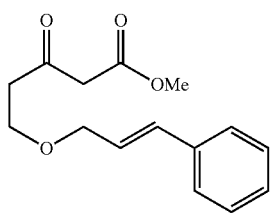

Yellow oil. (931.2 mg, 71% overall yield over 3 steps)

$^1$H NMR (500 MHz, CDCl$_3$): δ ppm (keto+enol) 12.07 (s, 0.1H, enol), 7.41-7.35 (m, 2H, keto+enol), 7.34-7.28 (m, 2H, keto+enol), 7.26-7.21 (m, 1H, keto+enol), 6.59 (d, J=15.9 Hz, 1H, keto+enol), 6.25 (dt, J=15.9, 6.1 Hz, 1H, keto+enol), 5.10 (s, 0.1H, enol), 4.13 (dd, J=6.1, 1.5 Hz, 2H, keto+enol), 3.75 (t, J=6.2 Hz, 2H, keto+enol), 3.73 (s, 3H, keto+enol), 3.52 (s, 1.8H, keto), 2.83 (t, J=6.2 Hz, 1.8H, keto), 2.52 (t, J=6.5 Hz, 0.2H, enol).

$^{13}$C NMR (125 MHz, CDCl$_3$): δ ppm (keto+enol) 201.3, 175.7, 173.0, 167.6, 136.7, 136.7, 132.7, 132.6, 128.6, 127.2, 126.6, 126.5, 125.9, 125.7, 90.2, 71.8, 71.7, 66.4, 64.9, 52.4, 51.2, 49.6, 43.2, 35.8.

HRMS (ESI) calculated for C$_{15}$H$_{18}$O$_4$[M+Na]$^+$: 285.110, Found: 285.109.

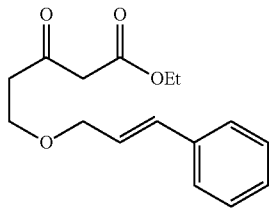

1aa

Yellow oil. (1.08 g, 78% overall yield over 3 steps)

$^1$H NMR (500 MHz, CDCl$_3$): δ ppm (keto+enol) 12.15 (s, 0.1H, enol), 7.38 (d, J=7.5 Hz, 2H, keto+enol), 7.31 (t, J=7.6 Hz, 2H, keto+enol), 7.24 (t, J=7.3 Hz, 1H, keto+enol), 6.59 (d, J=15.9 Hz, 1H, keto+enol), 6.26 (dt, J=15.9, 6.1 Hz, 1H, keto+enol), 5.08 (s, 0.1H, enol), 4.19 (q, J=7.2 Hz, 2H, keto+enol), 4.14 (dd, J=6.1, 1.4 Hz, 2H, keto+enol), 3.76 (t, J=6.2 Hz, 1.8H, keto), 3.72 (t, 1=6.4 Hz, 0.2H, enol), 3.50 (s, 1.8H, keto), 2.84 (t, J=6.2 Hz, 1.8H, keto), 2.52 (t, J=6.5 Hz, 0.2H, enol), 1.27 (t, J=7.1 Hz, 31H, keto+enol).

$^{13}$C NMR (125 MHz, CDCl$_3$): δ ppm (keto+enol) 201.5, 175.6, 172.7, 167.2, 136.7, 132.8, 132.7, 128.7, 127.9, 127.8, 126.6, 125.9, 125.8, 90.5, 71.9, 71.7, 66.5, 65.0, 61.5, 60.2, 49.9, 43.2, 35.8, 14.4, 14.2.

HRMS (ESI) calculated for C$_{16}$H$_{20}$O$_4$[M+Na]$^+$: 299.1259, Found: 299.1260.

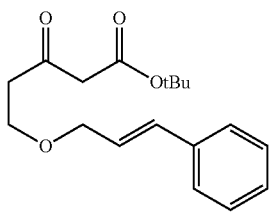

1ab

Colorless oil. (1.02 g, 67% overall yield over 3 steps)

$^1$H NMR (500 MHz, CDCl$_3$): δ ppm (keto+enol) 12.29 (s, 0.1H, enol), 7.38 (d, J=7.5 Hz, 2H, keto+enol), 7.31 (t, J=7.6 Hz, 2H, keto+enol), 7.24 (t, 0.1=7.3 Hz, 1H, keto+enol), 6.59 (d, J=15.9 Hz, 1H, keto+enol), 6.26 (dt, J:=15.9, 6.1 Hz, 11.1, keto+enol), 4.98 (s, 0.1H, enol), 4.14 (dd, J=6.1, 1.5 Hz, 2H, keto+enol), 3.76 (t, J=6.3 Hz, 1.8H, keto), 3.71 (t, J=6.6 Hz, 0.2H, enol), 3.41 (s, 1.8H, keto), 2.83 (t, J=6.3 Hz, 1.8H, keto), 2.49 (t, J=6.6 Hz, 0.2H, enol), 1.49 (s, 0.9H, enol), 1.47 (s, 8.1H, keto).

$^{13}$C NMR (125 MHz, CDCl$_3$): δ ppm (keto+enol) 201.9, 174.9, 172.7, 166.4, 136.7, 132.7, 132.6, 128.7, 127.8, 126.6, 126.0, 125.9, 91.9, 82.1, 81.0, 71.9, 71.7, 66.5, 65.0, 51.2, 43.1, 35.8, 28.4, 28.1.

HRMS (ESI) calculated for C$_{18}$H$_{24}$O$_4$[M+Na]$^+$: 327.1572, Found: 327.1577.

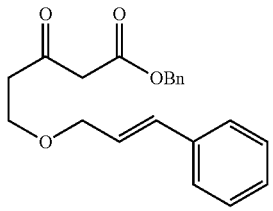

1ac

Colorless oil. (879.8 mg, 52% overall yield over 3 steps)

$^1$H NMR (500 MHz, CDCl$_3$): δ ppm (keto+enol) 12.06 (s, 0.1H, enol), 7.40-7.29 (m, 8H, keto+enol), 7.27-7.22 (m, 1H, keto+enol), 6.59 (d, J=15.9 Hz, 1H, keto+enol), 6.24 (dt, J=15.9, 6.1 Hz, 1H, keto+enol), 5.18 (s, 2H, keto+enol), 5.12 (s, 0.1H, enol), 4.16 (dd, J=6.0, 1.5 Hz, 0.2H, enol), 4.12 (dd, J=6.1, 1.5 Hz, 1.8H, keto), 3.75 (t, J=6.2 Hz, 1.8H, keto), 3.73-3.70 (m, 0.2H, enol), 3.57 (s, 1.8H, keto), 2.82 (t, J=6.2 Hz, 1.8H, keto), 2.53 (t, J=6.5 Hz, 0.21H, enol).

$^{13}$C NMR (125 MHz, CDCl$_3$): δ ppm (keto+enol) 201.3, 176.2, 172.5, 167.0, 136.7, 135.4, 132.8, 132.7, 128.8, 128.7, 128.6, 128.5, 128.4, 128.3, 127.9, 126.7, 125.8, 90.4, 71.9, 71.8, 67.3, 66.4, 65.9, 65.0, 49.9, 43.3, 35.9.

HRMS (ESI) calculated for C$_{21}$H$_{22}$O$_4$[M+Na]$^+$: 361.1416, Found: 361.1418.

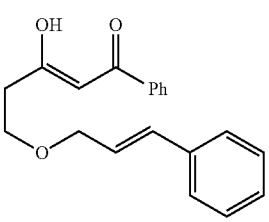

1ad

Orange oil. (185.0 mg, 12% overall yield over 3 steps)

$^1$H NMR (500 MHz, CDCl$_3$): δ ppm 16.13 (s, 1H), 7.88 (d, J=6.9 Hz, 2H), 7.52 (t, J=7.4 Hz, 1H), 7.43 (t, J=7.7H-z, 2H), 7.37 (d, J=7.5 Hz, 2H), 7.30 (t, J=7.6 Hz, 2H), 7.24 (t, J=7.3 Hz, 1H), 6.62 (d, J=15.9 Hz, 1H), 6.33-6.24 (m, 2H), 4.19 (dd, J=6.0, 1.4 Hz, 2H), 3.84 (t, J=6.3 Hz, 2H), 2.75 (t, J=6.4 Hz, 2H).

$^{13}$C NMR (125 MHz, CDCl$_3$): δ ppm 194.6, 183.3, 136.8, 134.9, 132.8, 132.5, 128.8, 128.7, 127.9, 127.2, 126.7, 125.9, 97.0, 71.9, 66.2, 40.0.

HRMS (ESI) calculated for C$_{20}$H$_{20}$O$_3$[M+Na]$^+$: 331.1310, Found: 331.1311.

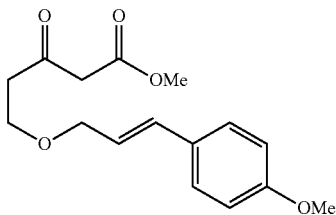

1b

Colorless oil. (1.04 g, 71% overall yield over 3 steps)

¹H NMR (500 MHz, CDCl₃): δ ppm (keto+enol) 12.05 (s, 0.1H, enol), 7.31 (d, J=8.7 Hz, 2H, keto+enol), 6.85 (d, J=8.7 Hz, 2H, keto+enol), 6.53 (d, J=15.9 Hz, 1H, keto+enol), 6.11 (dt, J=15.9, 6.3 Hz, 1H, keto+enol), 5.09 (s, 0.1H, enol), 4.11 (dd, J=6.2, 1.4 Hz, 2H, keto+enol), 3.80 (s, 3H, keto+enol), 3.77-3.67 (m, 5H, keto+enol), 3.52 (s, 1.8H, keto), 2.82 (t, J=6.2 Hz, 1.8H, keto), 2.51 (t, J=6.5 Hz, 0.2H, enol).

¹³C NMR (125 MHz, CDCl₃): δ ppm (keto+enol) 201.4, 175.8, 173.1, 167.6, 159.5, 132.6, 132.5, 129.4, 127.8, 123.6, 123.4, 114.1, 90.2, 72.1, 71.9, 66.3, 64.8, 55.4, 52.5, 51.3, 49.6, 43.3, 35.8.

HRMS (ESI) calculated for $C_{16}H_{20}O_5$ [M+Na]⁺: 315.121, Found: 315.122.

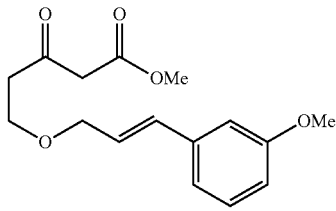

1c

Yellow oil. (1.13 g, 77% overall yield over 3 steps)

¹H NMR (500 MHz, CDCl₃): δ ppm (keto+enol) 12.06 (s, 0.1H, enol), 7.23 (t, J=7.9 Hz, 1H, keto+enol), 6.98 (d, J=7.6 Hz, 1H, keto+enol), 6.92 (s, 1H, keto+enol), 6.80 (dd, J=8.2, 1.9 Hz, 1H, keto+enol), 6.56 (d, J=15.9 Hz, 1H, keto+enol), 6.25 (dt, J=15.9, 6.1 Hz, 1H, keto+enol), 5.09 (s, 0.1H, enol), 4.14 (dd, J=6.0, 1.5 Hz, 2H, keto+enol), 3.81 (s, 3H, keto+enol), 3.79-3.72 (m, 5-1, keto+enol), 3.53 (s, 1.8H, keto), 2.83 (t, J=6.1 Hz, 1.8H, keto), 2.52 (t, J=6.5 Hz, 0.2H, enol).

¹³C NMR (125 MHz, CDCl₃): δ ppm (keto+enol) 201.37, 167.63, 159.94, 139.67, 138.19, 132.67, 129.78, 129.68, 129.59, 126.29, 126.14, 120.03, 119.34, 118.03, 113.59, 113.54, 113.10, 111.90, 111.26, 90.26, 71.86, 70.39, 66.49, 65.01, 55.36, 52.51, 52.07, 49.69, 43.28, 35.85.

HRMS (ESI) calculated for $C_{16}H_{20}O_5$ [M+Na]⁺: 315.121, Found: 315.122.

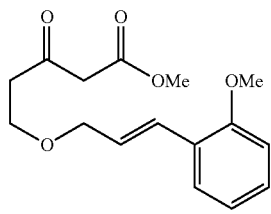

1d

Colorless oil. (1.02 g, 70% overall yield over 3 steps)

¹H NMR (500 MHz, CDCl₃): δ ppm (keto+enol) 12.05 (s, 0.1H, enol), 7.43 (dd, J=7.6, 1.8 Hz, 1H, keto+enol), 7.25-7.20 (m, 1H, keto+enol), 6.97-6.82 (m, 3H, keto+enol), 6.27 (dt, J=16.1, 6.2 Hz, 1H, keto+enol), 5.09 (s, 0.1H, enol), 4.14 (dd, J=6.2, 1.5 Hz, 1.8H, keto+enol), 3.84 (s, 3H, keto+enol), 3.79-3.69 (m, 5H, keto+enol), 3.53 (s, 1.8H, keto), 2.82 (t, J=6.2 Hz, 1.8H, keto), 2.52 (t, J=6.5 Hz, 0.2H, enol).

¹³C NMR (125 MHz, CDCl₃): δ ppm (keto+enol) 201.5, 175.9, 173.1, 167.7, 156.9, 129.4, 128.9, 128.9, 127.9, 127.8, 127.1, 127.1, 126.5, 126.4, 126.3, 125.8, 125.7, 120.8, 120.7, 110.9, 90.2, 72.4, 72.3, 66.3, 64.9, 64.4, 55.5, 52.5, 51.3, 49.6, 43.3, 35.8.

HRMS (ESI) calculated for $C_{16}H_{20}O_5$[M+Na]⁺: 315.1208, Found: 315.1213.

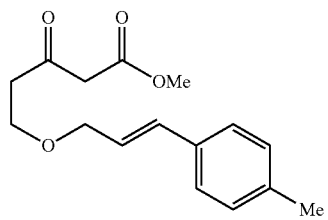

1e

Pale yellow oil. (994.8 mg, 72% overall yield over 3 steps)

¹H NMR (500 MHz, CDCl₃): δ ppm (keto+enol) 12.06 (s, 0.1H, enol), 7.28 (d, J=8.0 Hz, 2H, keto+enol), 7.12 (d, J=7.9 Hz, 2H, keto+enol), 6.56 (d, J=15.9 Hz, 1H, keto+enol), 6.20 (dt, J=15.9, 6.2 Hz, 1H, keto+enol), 5.09 (s, 0.1H, enol), 4.12 (dd, J=6.2, 1.5 Hz, 2H, keto+enol), 3.82-3.68 (m, 5H, keto+enol), 3.52 (s, 1.8H, keto), 2.83 (t, J=6.2 Hz, 2H, keto), 2.51 (t, J=6.5 Hz, 0.2H, enol), 2.33 (s, 3H, keto+enol).

¹³C NMR (125 MHz, CDCl₃): δ ppm (keto+enol) 201.4, 175.8, 173.1, 167.6, 137.7, 137.7, 133.9, 132.8, 132.7, 129.4, 126.5, 124.8, 124.7, 90.2, 72.0, 71.9, 66.4, 64.9, 52.5, 51.3, 49.7, 43.3, 35.8, 21.3.

HRMS (ESI) calculated for $C_{16}H_{20}O_4$ [M+Na]⁺: 299.1259, Found: 299.1269.

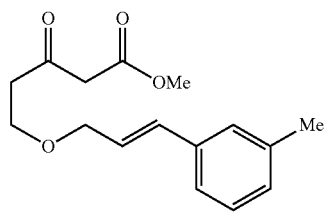

1f

Pale yellow oil. (953.3 mg, 69% overall yield over 3 steps)

¹H NMR (500 MHz, CDCl₃): δ ppm (keto+enol) 12.06 (s, 0.1H, enol), 7.24-7.16 (m, 3H, keto+enol), 7.10-7.04 (m, 1H, keto+enol), 6.56 (d, J=15.9 Hz, 1H, keto+enol), 6.24 (dt, J=15.9, 6.1 Hz, 1H, keto+enol), 5.10 (s, 0.1H, enol), 4.13 (dd, J=6.1, 1.5 Hz, 2H, keto+enol), 3.82-3.66 (m, 5H, keto+enol), 3.53 (s, 1.81H, keto), 2.83 (t, J=6.2 Hz, 1.8H, keto), 2.52 (t, J=6.5 Hz, 0.2H, enol), 2.34 (s, 3H, keto+enol).

¹C NMR (125 MHz, CDCl₃): δ ppm (keto+enol) 201.4, 175.8, 173.1, 167.6, 138.2, 136.6, 132.9, 132.8, 131.3, 128.7, 128.6, 128.6, 128.5, 127.4, 127.3, 125.7, 125.6, 123.8, 123.7, 90.2, 71.9, 64.9, 52.5, 49.7, 43.3, 21.5.

HRMS (ESI) calculated for C₁₆H₂₀O₄ [M+Na]⁺: 299.1259, Found: 299.1263.

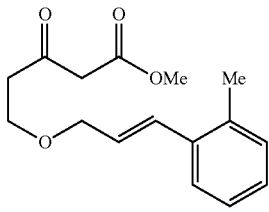

1g

Yellow oil. (994.6 mg, 72% overall yield over 3 steps)

¹H NMR (500 MHz, CDCl₃): δ ppm (keto+enol) 12.07 (s, 0.1H, enol), 7.47-7.41 (m, 1H, keto+enol), 7.19-7.11 (m, 3H, keto+enol), 6.81 (d, J=15.8 Hz, 1H, keto+enol), 6.14 (dt, J=15.8, 6.1 Hz, 1H, keto+enol), 5.10 (s, 0.1H, enol), 4.16 (dd, J=6.1, 1.5 Hz, 2H, keto+enol), 3.77 (t, J=6.2 Hz, 21H, keto+enol), 3.73 (s, 3H, keto+enol), 3.53 (s, 1.8H, keto), 2.84 (t, J=6.2 Hz, 1.8H, keto), 2.53 (t, J=6.5 Hz, 0.2H, enol), 2.35 (s, 3H, keto+enol).

¹³C NMR (125 MHz, CDCl₃): a ppm (keto+enol) 201.4, 175.8, 173.1, 167.6, 135.8, 135.6, 130.6, 130.5, 130.4, 127.8, 127.7, 127.2, 127.1, 126.2, 125.9, 90.2, 72.1, 71.9, 66.4, 64.9, 52.5, 51.3, 49.7, 43.3, 35.9, 19.9.

HRMS (ESI) calculated for C₁₆H₂₀O₄N [M+Na]⁺: 299.1259, Found: 299.1265.

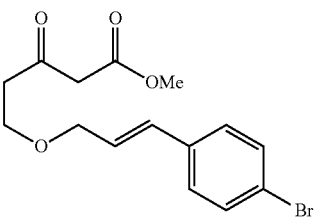

1h

Colorless oil. (1.25 g, 73% overall yield over 3 steps)

¹H NMR (500 MHz, CDCl₃): δ ppm (keto+enol) 12.06 (s, 0.1H, enol), 7.43 (d, J=8.5 Hz, 2H, keto+enol), 7.24 (d, 0.1=8.4 Hz, 2H, keto+enol), 6.52 (d, J=16.0 Hz, 1H, keto+enol), 6.24 (dt, J=16.0, 5.9 Hz, 1H, keto+enol), 5.09 (s, 0.1H, enol), 4.11 (dd, J=6.0, 1.5 Hz, 2H, keto+enol), 3.79-3.67 (m, 5H, keto+enol), 3.52 (s, 1.8H, keto), 2.83 (t, J=6.1 Hz, 1.8H, keto), 2.51 (t, J=6.4 Hz, 0.2H, enol).

¹³C NMR (125 MHz, CDCl₃): δ ppm (keto+enol) 201.3, 175.7, 173.0, 167.6, 135.7, 131.8, 131.4, 131.3, 128.1, 126.8, 126.7, 121.6, 90.3, 71.7, 71.5, 66.6, 65.1, 52.5, 51.3, 49.7, 43.2, 35.8.

HRMS (ESI) calculated for C₁₅H₁₇BrO₄[M+Na]⁺: 363.0208, Found: 363.0213.

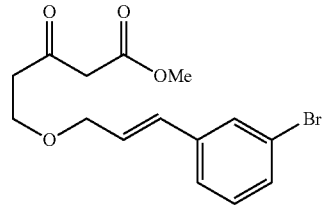

1i

Yellow oil. (1.28 g, 75% overall yield over 3 steps)

¹H NMR (500 MHz, CDCl₃): δ ppm (keto+enol) 12.06 (s, 0.11H, enol), 7.52 (s, 1H, keto+enol), 7.36 (d, J=7.9 Hz, 1H, keto+enol), 7.28 (d, J=7.7 Hz, 1H, keto+enol), 7.17 (t, J=7.8 Hz, 1H, keto+f enol), 6.52 (d, 1=15.9 Hz, 1H, keto+enol), 6.25 (dt, J=15.9, 5.9 Hz, 1H, keto+enol), 5.09 (s, OH, enol), 4.13 (dd, J=5.8, 1.6 Hz, 2H, keto+enol), 3.81-3.67 (m, 5H, keto+enol), 3.52 (s, 1.8H, keto), 2.83 (t, J=6.2 Hz, 1.8H, keto), 2.51 (t, J=6.5 Hz, 0.2H, enol).

¹³C NMR (125 MHz, CDCl₃): δ ppm (keto+enol) 201.3, 175.7, 173.0, 167.6, 138.9, 131.0, 1309, 130.7, 130.6, 130.3, 130.2, 129.5, 127.5, 125.2, 122.9, 90.3, 71.5, 71.4, 65.1, 64.9, 52.5, 52.0, 49.7, 43.2, 35.8.

HRMS (ESI) calculated for C₁₅H₁₇BrO₄[M+Na]⁺: 363.0208, Found: 363.0204.

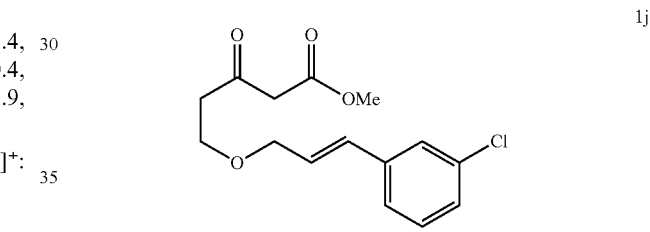

1j

Yellow oil. (1.13 g, 76% overall yield over 3 steps)

¹H NMR (500 MHz, CDCl₃): δ ppm (keto+enol) 12.06 (s, 0.1H, enol), 7.36 (s, 1H, keto+enol), 7.25-7.17 (m, 3H, keto+enol), 6.53 (d, J=15.9 Hz, H, keto+enol), 6.26 (dt, J=15.9, 5.9 Hz, 1H, keto+enol), 5.09 (s, 0.1H, enol), 4.13 (dd, J=5.8, 1.5 Hz, 2H, keto+enol), 3.80-3.68 (m, 5H, keto+enol), 3.52 (s, 1.81H, keto), 2.83 (t, J=6.2 Hz, 1.8H, keto), 2.51 (t, J=6.4 Hz, 0.2H, enol).

¹³C NMR (125 MHz, CDCl₃): δ ppm (keto+enol) 201.3, 175.7, 173.1, 167.6, 138.6, 134.6, 131.1, 131.0, 129.9, 129.8, 128.0, 127.8, 127.7, 127.6, 127.4, 126.6, 124.8, 90.3, 71.6, 71.4, 65.3, 65.1, 52.5, 51.3, 49.7, 43.2, 35.8.

HRMS (ESI) calculated for C₁₅H₁₇ClO₄[M+Na]⁺: 319.0713, Found: 319.0714.

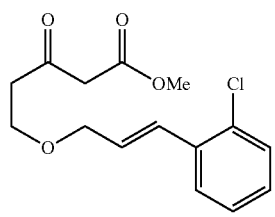

1k

Pale yellow oil. (1.04 g, 70% overall yield over 3 steps)

¹H NMR (500 MHz, CDCl₃): δ ppm (keto+enol) 12.06 (s, 0.1H, enol), 7.53 (dd, J=7.6, 1.8 Hz, 1H, keto+enol), 7.34

(dd, J=7.7, 1.6 Hz, 1H, keto+enol), 7.22 (td, J=7.5, 1.6 Hz, 1H, keto+enol), 7.18 (td, J=7.6, 1.8 Hz, 1H, keto+enol), 6.98 (d, J=15.9 Hz, 1H, keto+enol), 6.24 (dt, J=16.0, 5.9 Hz, 1H, keto+enol), 5.10 (s, 0.1H, enol), 4.17 (dd, J=6.0, 1.6 Hz, 2H, keto+enol), 3.78 (t, J=6.1 Hz, 2H, keto+enol), 3.73 (s, 3H, keto+enol), 3.53 (s, 1.8H, keto), 2.84 (t, J=6.1 Hz, 1.8H, keto), 2.53 (t, J=6.5 Hz, 0.2H, enol).

$^{13}$C NMR (125 MHz, CDCl$_3$): δ ppm (keto+enol) 201.4, 175.7, 173.1, 167.6, 134.9, 133.2, 131.6, 129.8, 128.9, 128.8, 128.7, 128.7, 127.2, 127.1, 127.1, 127.0, 90.3, 71.8, 71.6, 66.6, 65.1, 63.8, 52.5, 51.3, 49.7, 43.3, 35.8.

HRMS (ESI) calculated for C$_{15}$H$_{17}$ClO$_4$[M+Na]$^+$: 319.0713, Found: 319.0710.

1l

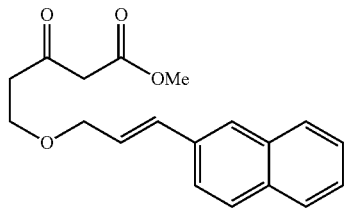

Colorless oil. (1.11 g, 71% overall yield over 3 steps)

$^1$H NMR (500 MHz, CDCl$_3$): δ ppm (keto+enol) 12.09 (s, 0.1H, enol), 7.86-7.76 (n, 3H, keto+enol), 7.74 (s, 1H, keto+enol), 7.60 (dd, J=8.5, 1.8 Hz, 1H, keto+enol), 7.52-7.40 (m, 2H, keto+enol), 6.76 (d, J=15.9 Hz, 1H, keto+enol), 6.39 (dt, J=16.0, 6.1 Hz, 1H, keto+enol), 5.12 (s, 0.11H, enol), 4.20 (dd, J=6.0, 1.5 Hz, 2H, keto+enol), 3.80 (t, J=6.2 Hz, 2H, keto+enol), 3.74 (s, 3H, keto+enol), 3.54 (s, 18H, keto), 2.85 (t, J=6.2 Hz, 1.8H, keto), 2.55 (t, J=6.5 Hz, 0.21H, enol).

$^{13}$C NMR (125 MHz, CDCl$_3$): δ ppm (keto+enol) 201.4, 175.8, 173.1, 167.6, 134.2, 133.7, 133.2, 132.8, 132.8, 128.3, 128.1, 128.0, 127.8, 127.8, 126.7, 126.4, 126.3, 126.2, 126.1, 126.0, 123.7, 90.3, 72.0, 71.8, 65.1, 65.0, 52.5, 51.3, 49.7, 43.3, 35.9.

HRMS (ESI) calculated for C$_{19}$H$_{20}$O$_4$[M+Na]$^+$: 335.1259, Found: 335.1258.

1m

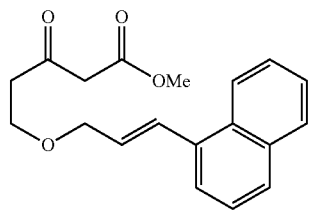

Yellow oil. (1.08 g, 69% overall yield over 3 steps)

$^1$H NMR (500 MHz, CDCl$_3$): δ ppm (keto+enol) 12.11 (s, 0.1H, enol), 8.18-8.03 (m, 1H, keto+enol), 7.89-7.82 (m, 1H, keto+enol), 7.79 (d, J=8.2 Hz, 1H, keto+enol), 7.61 (d, J=7.1 Hz, 1H, keto+enol), 7.55-7.47 (m, 2H, keto+enol), 7.47-7.43 (m, 1H, keto+enol), 7.36 (d, J=15.7 Hz, 1H, keto+enol), 6.30 (dt, J=15.7, 5.9 Hz, 1H, keto+enol), 5.14 (s, 0.1H, enol), 4.26 (dd, J=5.9, 1.6 Hz, 2H, keto+enol), 3.84 (t, J=6.2 Hz, 1.8H, keto), 3.80 (t, J=6.4 Hz, 0.2H, enol), 3.74 (s, 3H, keto+enol), 3.55 (s, 1.8H, keto), 2.87 (t, J=6.1 Hz, 1.8H, keto+enol), 2.57 (t, J=6.4 Hz, 0.2H, enol).

$^{13}$C NMR (125 MHz, CDCl$_3$): δ ppm 201.4, 175.8, 173.1, 167.6, 134.5, 133.7, 131.3, 129.8, 129.6, 129.2, 129.1, 128.6, 128.2, 128.2, 126.2, 125.9, 125.7, 124.1, 124.1, 123.9, 90.3, 72.0, 71.9, 66.5, 65.1, 52.5, 51.3, 49.7, 43.3, 35.9.

HRMS (ESI) calculated for C$_{19}$H$_{20}$O$_4$[M+Na]$^+$: 335.1259, Found: 335.1257.

1n

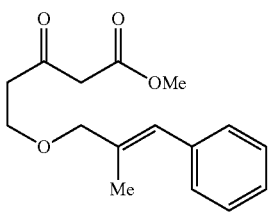

Yellow oil. (967.2 mg, 70% overall yield over 3 steps)

$^1$H NMR (500 MHz, CDCl$_3$): δ ppm (keto+enol) 12.04 (s, 0.1H, enol), 7.30 (t, J=7.5 Hz, 2H, keto+enol), 7.27-7.23 (m, 2H, keto+enol), 7.19 (t, J=7.2 Hz, 1H, keto+enol), 6.45 (s, 1H, keto+enol), 5.08 (s, 0.1H, enol), 4.01 (s, 0.2H, enol), 3.99 (s, 1.8H, keto), 3.75-3.63 (m, 5H, keto+enol), 3.51 (s, 1.8H, keto), 2.81 (t, J=6.1 Hz, 1.8H, keto), 2.50 (t, J=6.4 Hz, 0.2H, enol), 1.84 (s, 3H, keto+enol).

$^{13}$C NMR (125 MHz, CDCl$_3$): δ ppm (keto+enol) 201.4, 175.9, 173.0, 167.6, 137.5, 137.5, 135.1, 135.0, 129.0, 129.0, 128.2, 127.2, 127.1, 126.6, 126.6, 90.2, 77.4, 77.2, 66.1, 64.8, 52.4, 51.2, 49.7, 43.2, 35.8, 15.5.

HRMS (ESI) calculated for C$_{16}$H$_{20}$O$_4$[M+Na]$^+$: 299.1259, Found: 299.1254.

1o

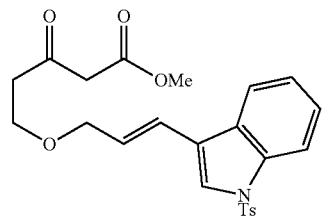

Yellow oil. (1.68 g, 74% overall yield over 3 steps)

$^1$H NMR (500 MHz, CDCl$_3$): 5 ppm (keto+enol) 12.08 (s, 0.1H, enol), 7.98 (d, J=8.3 Hz, 1H, keto+enol), 7.75 (d, J=8.4 Hz, 2H, keto+enol), 7.72 (d, J=7.9 Hz, 1H, keto+enol), 7.59 (s, 1H, keto+enol), 7.36-7.30 (m, 1H, keto+enol), 7.29-7.24 (m, 1H, keto+enol), 7.20 (d, J=8.2 Hz, 2H, keto+enol), 6.66 (d, J=16.2 Hz, 1H, keto+enol), 6.32 (dt, J=16.1, 6.0 Hz, 1H, keto+enol), 5.11 (s, 0.1H, enol), 4.15 (dd, J=6.1, 1.5 Hz, 1H, keto+enol), 3.77 (t, J=6.2 Hz, 1H, keto+enol), 3.73 (s, 3H, keto+enol), 3.53 (s, 1.8H, keto), 2.84 (t, J=6.1 Hz, 1.8H, keto), 2.53 (t, 1=6.5 Hz, 0.2H, enol), 2.32 (s, 3H, keto+enol).

$^{13}$C NMR (125 MHz, CDCl$_3$): δ ppm (keto+enol) 201.3, 175.7, 173.1, 167.6, 145.2, 135.6, 135.2, 130.0, 129.1, 127.2, 127.0, 127.0, 125.1, 124.3, 124.3, 123.6, 123.4, 123.2, 120.5, 120.1, 113.9, 90.3, 72.1, 71.9, 66.5, 65.0, 52.5, 51.3, 49.7, 43.2, 35.8, 21.7.

HRMS (ESI) calculated for C$_{24}$H$_{25}$NO$_6$S [M+Na]$^+$: 478.1300, Found: 478.1308.

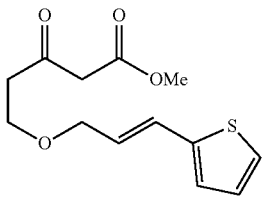

1p

Yellow oil. (1.01 g, 76% overall yield over 3 steps)

$^1$H NMR (500 MHz, CDCl$_3$): δ ppm (keto+enol) 12.05 (s, 0.1H, enol), 7.18-7.14 (m, 1H, keto+enol), 6.98-6.93 (m, 2H, keto+enol), 6.71 (d, J=15.7 Hz, 1H, keto+enol), 6.08 (dt, J=15.7, 6.1 Hz, 1H, keto+enol), 5.09 (s, 0.1H, enol), 4.09 (dd, J=6.1, 1.5 Hz, 2H, keto+enol), 3.79-3.71 (m, 51.1, keto+enol), 3.52 (s, 1.8H, keto), 2.82 (t, J=6.2 Hz, 1.81H, keto), 2.51 (t, J=6.5 Hz, 0.2H, enol).

$^{13}$C NMR (125 MHz, CDCl$_3$): δ ppm (keto+enol) 201.3, 175.7, 173.1, 167.6, 141.8, 127.5, 126.0, 126.0, 125.9, 125.8, 125.5, 125.4, 124.6, 124.6, 90.2, 71.5, 71.4, 66.5, 65.0, 52.5, 51.3, 49.7, 43.2, 35.8.

HRMS (ESI) calculated for C$_{13}$H$_{16}$O$_4$S [M+Na]$^+$: 291.0667, Found: 291.0662.

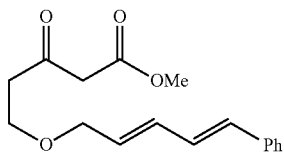

1q

Yellow oil. (1.10 g, 76% overall yield over 3 steps)

$^1$H NMR (500 MHz, CDCl$_3$): δ ppm (keto+enol) 12.06 (s, 0.1H, enol), 7.39 (d, J=7.4 Hz, 2H, keto+enol), 7.31 (t, J=7.6 Hz, 2H, keto+enol), 7.22 (t, J=7.3 Hz, 1H, keto+enol), 6.77 (dd, J=15.6, 10.5 Hz, J H, keto+enol), 6.55 (d, J=15.7 Hz, 1H, keto+enol), 6.40 (dd, J=15.0, 10.7 Hz, 1H, keto+enol), 5.85 (dt, J=15.2, 6.2 Hz, 1H, keto+enol), 5.09 (s, 0.1H, enol), 4.06 (dd, J=6.3, 1.4 Hz, 2H, keto+enol), 3.78-3.67 (m, 5H, keto+enol), 3.52 (s, 1.814, keto), 2.82 (t, j 6.2 Hz, 1.8H, keto), 2.51 (t, J=6.5 Hz, 0.2H, enol).

$^1$C NMR (125 MHz, CDCl$_3$): δ ppm (keto+enol) 201.4, 175.8, 173.1, 167.6, 137.2, 133.2, 133.2, 133.0, 133.0, 129.9, 129.7, 128.7, 128.3, 128.2, 127.8, 126.5, 90.2, 71.6, 71.4, 65.3, 65.0, 52.5, 51.3, 49.7, 43.3, 35.8, 15.2.

HRMS (ESI) calculated for C$_{17}$H$_{20}$O$_4$[M+Na]$^+$: 311.1259, Found: 311.1256.

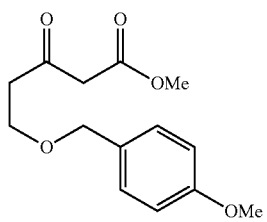

1r

Pale yellow oil. (998.6 mg, 75% overall yield over 3 steps)

$^1$H NMR (500 MHz, CDCl$_3$): δ ppm (keto+enol) 12.03 (s, 0.1H, enol), 7.23 (d, J=8.6 Hz, 2H, keto+enol), 6.87 (d, J=8.7 Hz, 2H, keto+enol), 5.06 (s, 0.1H, enol), 4.45 (s, 0.2H, enol), 4.43 (s, 1.8H, keto), 3.79 (s, 3H, keto+enol), 3.74-3.69 (m, 5H, keto+enol), 3.49 (s, 1.8H, keto), 2.80 (t, J=6.2 Hz, 1.8H, keto), 2.49 (t, J=6.5 Hz, 0.2H, enol).

$^{13}$C NMR (125 MHz, CDCl$_3$): δ ppm (keto+enol) 201.4, 175.9, 173.0, 167.6, 159.4, 130.1, 129.5, 129.4, 113.9, 90.1, 73.0, 72.8, 66.1, 64.8, 55.4, 52.4, 51.2, 49.6, 43.3, 35.8.

HRMS (ESI) calculated for C$_{14}$H$_{18}$O$_5$ [M+Na]$^+$: 289.1052, Found: 289.1046.

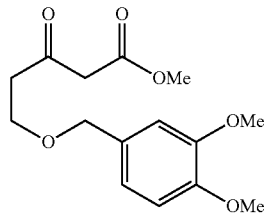

1s

Yellow oil. (1.13 g, 76% overall yield over 3 steps)

$^1$H NMR (500 MHz, CDCl$_3$): δ ppm (keto+enol) 12.04 (s, 0.1H, enol), 6.88-6.78 (m, 3H, keto+enol), 5.07 (s, 0.1H, enol), 4.45 (s, 0.2H, enol), 4.43 (s, 1.8H, keto), 3.88 (s, 3H, keto+enol), 3.86 (s, 3H, keto+enol), 3.74-3.64 (m, 5H, keto+enol), 3.49 (s, 1.8H, keto), 2.80 (t, J=6.1 Hz, 1.8H, keto), 2.49 (t, J=6.4 Hz, 0.2H, enol).

$^1$C NMR (125 MHz, CDCl$_3$): δ ppm (keto+enol) 201.3, 175.9, 173.0, 167.6, 149.1, 148.8, 130.6, 120.4, 120.3, 111.1, 111.0, 111.0, 110.9, 90.1, 73.3, 73.1, 66.1, 64.8, 56.0, 55.9, 55.8, 52.4, 51.2, 49.6, 43.2, 35.7.

HRMS ESI) calculated for C$_{15}$H$_{20}$O$_6$ [M+Na]$^+$: 319.1158, Found: 319.1154.

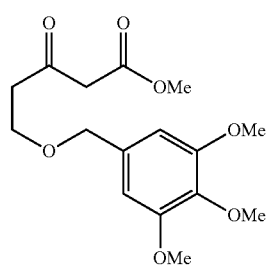

1t

Yellow oil. (1.19 g, 73% overall yield over 3 steps)

$^1$H NMR (500 MHz, CDCl$_3$): δ ppm (keto+enol) 12.05 (s, 0.1H, enol), 6.53 (s, 2H, keto+enol), 5.08 (s, 0.1H, enol), 4.44 (s, 0.2H, enol), 4.42 (s, 1.8H, keto), 3.84 (s, 6H, keto+enol), 3.81 (s, 3H, keto+enol), 3.74 (t, J=6.1 Hz, 2H, keto+enol), 3.70 (s, 3H, keto+enol), 3.49 (s, 1.8H, keto), 2.82 (t, J=6.1 Hz, 1.8H, keto), 2.51 (t, J=6.3 Hz, 0.2H, enol).

$^{13}$C NMR (125 MHz, CDCl$_3$): δ ppm (keto+enol) 201.2, 175.8, 173.0, 167.5, 153.4, 137.5, 137.4, 133.8, 133.7, 90.2, 73.5, 73.3, 66.4, 65.0, 60.9, 56.1, 56.1, 52.4, 51.2, 49.6, 43.1, 35.7.

HRMS (ESI) calculated for C$_{16}$H$_{22}$O$_7$ [M+Na]$^+$: 349.1263, Found: 349.1259.

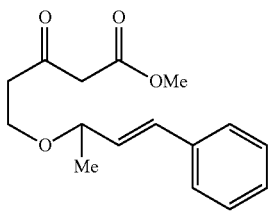

1u

Colorless oil. (967.0 mg, 70% overall yield over 3 steps)

$^1$H NMR (500 MHz, CDCl$_3$): δ ppm (keto+enol) 12.03 (s, 0.11H, enol), 7.39 (d, J=7.6 Hz, 2H, keto+enol), 7.32 (t, J=7.6 Hz, 2H, keto+enol), 7.24 (t, J=7.9 Hz, 1H, keto+enol), 6.52 (d, J=16.0 Hz, 1H, keto+enol), 6.08 (dd, J=16.0, 7.7 Hz, 1H, keto+enol), 5.08 (s, 0.1H, enol), 4.00 (p, J=6.6 Hz, 1H, keto+enol), 3.77 (dt, J=9.7, 6.2 Hz, 1H, keto+enol), 3.73 (s, 3H, keto+enol), 3.63 (dt, J=9.7, 6.3 Hz, 1H, keto+enol), 3.52 (s, 1.8H, keto), 2.84-2.73 (m, 1.8H, keto), 2.49 (t, J=6.6 Hz, 0.2H, enol), 1.31 (d, J=6.4 Hz, 3H, keto+enol).

$^{13}$C NMR (125 MHz, CDCl$_3$): δ ppm (keto+enol) 201.6, 176.0, 173.1, 167.7, 136.6, 131.6, 131.5, 131.4, 131.3, 128.7, 127.8, 126.6, 90.1, 77.2, 77.0, 64.6, 63.2, 52.4, 51.2, 49.7, 43.5, 36.0, 21.7.

HRMS (ESI) calculated for C$_{16}$H$_{20}$O$_4$ [M+Na]$^+$: 299.1259, Found: 299.1255.

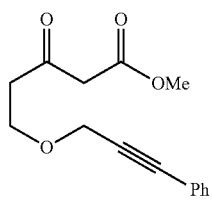

1v

Yellow oil. (885.0 mg, 68% overall yield over 3 steps)

$^1$H NMR (500 MHz, CDCl$_3$): δ ppm (keto+enol) 12.06 (s, 0.1H, enol), 7.47-7.42 (m, 2H, keto+enol), 7.34-7.28 (m, 3H, keto+enol), 5.11 (s, 0.1H, keto+enol), 4.38 (s, 0.2H, enol), 4.36 (s, 1.8H, keto), 3.86 (t, J=6.1 Hz, 1.81H, keto), 3.82 (t, J=6.4 Hz, 0.21H, enol), 3.72 (s, 3H, keto+enol), 3.53 (s, 1.8H, keto), 2.85 (t, J=6.2 Hz, 1.8H, keto), 2.54 (t, J=6.4 Hz, 0.2H, enol).

$^{13}$C NMR (125 MHz, CDCl$_3$): δ ppm (keto+enol) 201.1, 175.5, 173.0, 167.6, 131.9, 131.8, 128.6, 128.6, 128.5, 128.4, 122.6, 122.6, 90.2, 86.6, 86.6, 84.9, 84.8, 66.1, 64.7, 59.3, 59.1, 52.5, 51.3, 49.5, 43.1, 35.5.

HRMS (ESI) calculated for C$_{15}$H$_{16}$O$_4$[M+Na]V: 283.0946, Found: 283.0943.

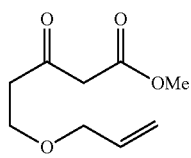

1w

Pale yellow oil. (689.0 mg, 74% overall yield over 3 steps)

$^1$H NMR (500 MHz, CDCl$_3$): δ ppm (keto+enol) 12.02 (s, 0.11H, enol), 5.91-5.80 (m, 1H, keto+enol), 5.24 (dd, J=17.2, 1.7 Hz, 1H, keto+enol), 5.16 (dd, J=10.4, 1.6 Hz, 1H, keto+enol), 5.05 (s, 0.1H, enol), 3.95 (dt, J=5.6, 1.5 Hz, 2H, keto+enol), 3.72 (s, 3H, keto+enol), 3.69 (t, J=6.2 Hz, 1.8H, keto), 3.64 (t, J=6.5 Hz, 0.2H, enol), 3.49 (s, 1.8H, keto), 2.79 (t, J=6.2 Hz, 1.8H, keto), 2.47 (t, J=6.5 Hz, 0.2H, enol).

$^{13}$C NMR (125 MHz, CDCl$_3$): δ ppm (keto+enol) 201.4, 175.8, 173.0, 167.6, 134.6, 134.5, 117.3, 117.3, 90.1, 72.2, 72.1, 66.4, 64.9, 52.4, 51.2, 49.6, 43.2, 35.8.

HRMS (ESI) calculated for C$_9$H$_{14}$O$_4$[M+Na]$^+$: 209.0790, Found: 209.0782.

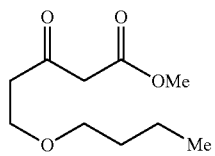

1y

Colorless oil. (567.4 mg, 56% overall yield over 3 steps)

$^1$H NMR (500 MHz, CDCl$_3$): δ ppm (keto+enol) 12.02 (s, 0.1H, enol), 5.06 (s, 0.1H, enol), 3.73 (d, J=5.5 Hz, 3H, keto+enol), 3.67 (t, J=6.2 Hz, 1.8H, keto), 3.63 (t, J=6.6 Hz, 0.2H, enol), 3.50 (s, 1.8H, keto), 3.40 (t, J=6.6 Hz, 2H, keto+enol), 2.77 (t, J=6.2 Hz, 1.8H, keto), 2.47 (t, J=6.5 Hz, 0.2H, enol), 1.58-1.45 (m, 2H, keto+enol), 1.38-1.29 (m, 2H, keto+enol), 0.90 (t, J=7.4 Hz, 3H, keto+enol).

$^{13}$C NMR (125 MHz, CDCl$_3$): δ ppm (keto+enol) 201.7, 176.1, 173.1, 167.7, 90.0, 71.2, 71.0, 67.0, 65.6, 52.5, 52.4, 51.3, 50.0, 49.7, 43.3, 35.8, 31.8, 30.3, 19.4, 14.0.

HRMS (ESI) calculated for C$_{10}$H$_{18}$O$_4$[M+Na]$^+$: 225.1103, Found: 225.1100.

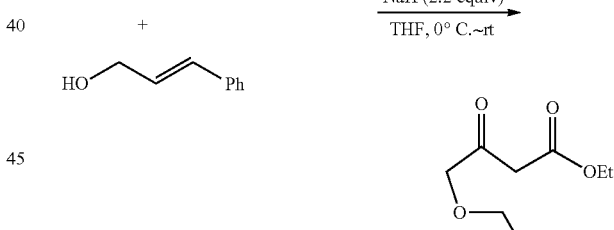

1x

To a suspension of 60% NaH (264 mg, 6.6 mmol) in THF (20 mL) at 0° C. was added cinnamyl alcohol (492.5 mg, 3.0 mmol), and the resulting mixture was stirred at ambient temperature for 2 h. To this mixture was then added ethyl 4-chloroacetateacetate (0.41 mL, 3.0 mmol) dropwise over 30 min, and the resulting clear yellow solution was stirred at ambient temperature overnight before it was cooled to 5° C., acidified to pH=4 using 5% HCl and extracted with the EtOAc (2×25 mL). The combined organics were washed with brine, dried over MgSO$_4$, and concentrated in vacuo. The resulting residue was purified by column chromatography on silica gel (hexanes:EtOAc=10:1 to 4:1) to give the corresponding β-keto esters 1x as colorless oil (605.9 mg, 77% yield).

¹H NMR (500 MHz, CDCl₃): δ ppm (keto+enol) 11.99 (s, 0.1H, enol), 7.39 (d, J=7.3 Hz, 2H, keto+enol), 7.33 (t, J=7.5 Hz, 2H, keto+enol), 7.29-7.22 (m, 1H, keto+enol), 6.62 (d, J=15.9 Hz, 1H, keto+enol), 6.26 (dt, J=: 15.9, 6.2 Hz, 1H, keto+enol), 5.33 (s, 0.1H, enol), 4.23 (dd, J=6.2, 1.4 Hz, 2H, keto+enol), 4.21-4.16 (m, 4H, keto+enol), 3.54 (s, 1.8H, keto), 1.26 (t, J=7.1 Hz, 3H, keto+enol).

LRMS (ESI) calculated for C₉H₁₄O₄[M+H]⁺: 263.1, Found: 263.1.

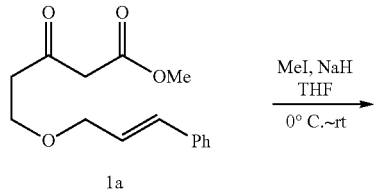

1a

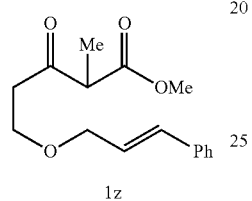

1z

To an oven dried 250 mL round bottom flask equipped with a magnetic stir bar was added the 1a (786.9 mg, 3.0 mmol), 144.0 mg of NaH (60% in oil, 3.6 mmol), and 40 mL of THF at 0° C. Methyl iodide (0.75 mL, 12.0 mmol) was added to the solution. The solution was stirred for 1 h at 0° C. and then stirred for 14 h at ambient temperature additionally. The saturated NH₄Cl solution was added to quench the reaction, followed by addition of ethyl acetate. The aqueous layer was extracted with ethyl acetate, dried and concentrated in vacuo. The crude was purified by silica gel column chromatography with ethyl acetate/hexane (1:3) to give the α-methyl-β-keto ester 1z as colorless oil (503.0 mg, 61% yield).

¹H NMR (500 MHz, CDCl₃): δ ppm 7.38 (d, J=7.9 Hz, 2H), 7.31 (t, J: 7.5 Hz, 2H), 7.26-7.21 (m, 1H), 6.59 (d, J=15.9 Hz, 1H), 6.25 (dtd, J=15.9, 6.0, 1.0 Hz, 1H), 4.13 (d, J=6.1 Hz, 2H), 3.78-3.74 (m, 2H), 3.73 (d, J=1.1 Hz, 3H), 3.60 (qd, J=7.2, 0.9 Hz, 1H), 2.89-2.79 (m, 2H), 1.36 (dd, J=7.2, 1.3 Hz, 3H).

¹³C NMR (125 MHz, CDCl₃): δ ppm 204.3, 171.0, 136.8, 132.7, 128.7, 127.9, 126.6, 125.9, 71.9, 65.1, 53.3, 52.6, 41.7, 12.7.

HRMS (ESI) calculated for C₁₆H₂₀O₄[M+Na]⁺: 299.1259, Found: 299.1257.

3. Optimization of Enantioselective CDC Reaction

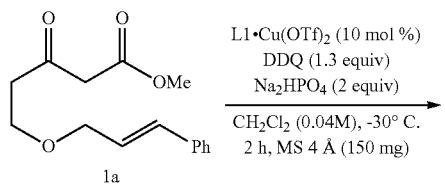

1a

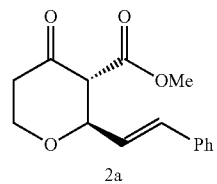

2a

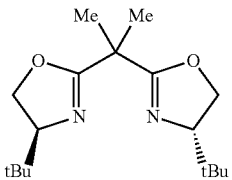

L1

| entry | deviation from standard condition | yield (%) | e.r. |
|---|---|---|---|
| 1 | none | 65 | 92:8 |
| 2 | w/o pre-complexation between L1 and Cu(OTt)₂ | 35-67 | 56:44~90:10 |
| 3 | w/o MS 4 Å | 10 | 87:13 |
| 4 | MS 3 Å instead of MS 4 Å | 68 | 90:10 |
| 5 | ClCH₂CH₂Cl instead of CH₂Cl₂ | 68 | 90:10 |
| 6 | MeCN instead of CH₂Cl₂ | 45 | 74:26 |
| 7 | CH₂Cl₂/MeCN instead of CH₂Cl₂ | 55 | 75:25 |
| 8 | CH₂Cl₂/Toluene instead of CH₂Cl₂ | 28 | 86:14 |
| 9 | CH₂Cl₂/THF instead of CH₂Cl₂ | 10 | 85:15 |
| 10 | Cl instead of OTf | 45 | 52:48 |
| 11 | OAc instead of OTf | 49 | 56:44 |
| 12 | ClO₄ instead of OTf | 65 | 69:31 |
| 13 | SbF₆ instead of OTf | 68 | 74:26 |
| 14 | PF₆ instead of OTf | 70 | 81:19 |
| 15 | BF₄ instead of OTf | 69 | 85:15 |

To an oven dried 20 mL reaction vial equipped with a magnetic stir bar under N₂ was added Na₂HPO₄ (56.8 mg, 0.4 mmol), 150 mg of 4 Å molecular sieve (powder), 1.0 mL of L1·Cu(OTf)₂ (0.02 M in CH₂Cl₂). The solution then was stirred for 1 h. The β-keto ester 1a was dissolved in 0.5 mL of CH₂Cl₂ and was added, and the solution stirred at ambient temperature for 30 minutes. The reaction was then cooled to −30° C., and DDQ (59.0 mg, 0.26 mmol) dissolved in 4.0 mL of DCM was added over 1 h by syringe pump. The reaction was stirred for 2 h at −30° C., and then 1.0 mL of Et₃N was added to quench the reaction. The solution was filtered over a pad of silica (4 cm) with ethyl acetate and concentrated under reduced pressure. The crude was purified by silica gel column chromatography with ethyl acetate/hexane (1:5) to give the tetrahydropyran-4-one 2a.

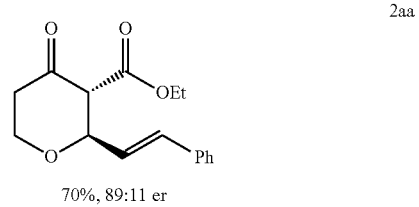

2aa

70%, 89:11 er

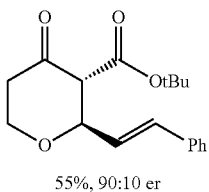

55%, 90:10 er

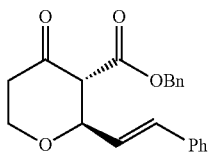

56%, 84:16 er

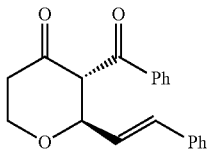

69%, 50:50 er

4. General Procedure for Enantioselective CDC Reaction

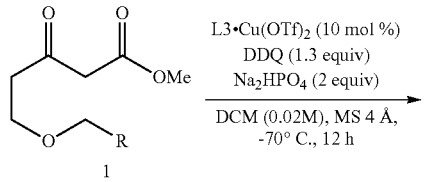

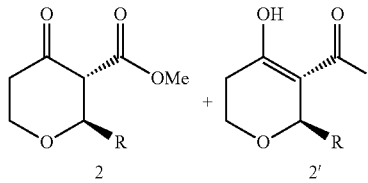

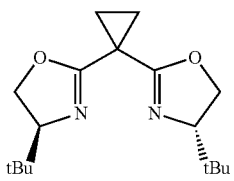

L3

To an oven dried 20 mL reaction vial equipped with a magnetic stir bar under $N_2$ was added $Na_2HPO_4$ (56.8 mg, 0.4 mmol), 250 mg of 4 Å molecular sieve (powder), 1.0 mL of L3·Cu(OTf)$_2$ (0.02 M in CH$_2$Cl$_2$), and 4.0 mL of CH$_2$C12. The solution then was stirred for 1 h. The corresponding β-keto ester was dissolved in 1.0 mL of CH$_2$Cl$_2$ and was added, and the solution stirred at ambient temperature for 30 mins. The reaction was then cooled to −70° C., and DDQ (59.0 mg, 0.26 mmol) dissolved in 4.0 mL of DCM was added over 1 h by syringe pump. The reaction was stirred for 12 h at −70° C., and then 1.0 mL of Et$_3$N was added to quench the reaction. The solution was filtered over a pad of silica (4 cm) with ethyl acetate and concentrated under reduced pressure. The crude was purified by silica gel column chromatography with ethyl acetate/hexane (1:4-1:6) to give the corresponding tetrahydropyran-4-ones 2. (The tetrahydropyran-4-ones 2 were isolated with the corresponding enol tautomers 2'.)

2a

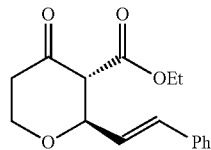

White solid. (43.3 mg, 83% yield, 95:5 e.r.)

$^1$H NMR (500 MHz, CDCl$_3$): δ ppm 7.39-7.36 (m, 2H), 7.35-7.30 (m, 2H), 7.29-7.25 (m, 1H), 6.72 (d, J=15.9 Hz, 1H), 6.17 (dd, J=15.9, 6.6 Hz, 1H), 4.58 (dd, J=10.1, 6.7 Hz, 1H), 4.38 (ddd, J=11.6, 7.3, 1.6 Hz, 1H), 3.87 (td, J=11.9, 2.8 Hz, 1H), 3.74 (s, 3H), 3.48 (d, J=10.1 Hz, 1H), 2.70 (ddd, J=14.4, 12.4, 7.3 Hz, 1H), 2.51 (dt, J=14.6, 2.0 Hz, 1H).

$^{13}$C NMR (125 MHz, CDCl$_3$): δ ppm 201.3, 168.0, 136.1, 133.7, 128.8, 128.5, 126.9, 125.8, 80.2, 66.5, 63.6, 52.4, 41.6.

HRMS (ESI) calculated for $C_{15}H_{16}O_4[M+Na]^+$: 283.0946, Found: 283.0946.

Chiral SFC (Chiralpak IG-3, 10% MeOH in CO$_2$, flow rate=2.5 mL/min, λ=250 nm): 3.3 min (major), 2.9 min (minor).

2aa

Yellow solid. (38.5 mg, 70% yield, 89:11 e.r.)

$^1$H NMR (500 MHz, CDCl$_3$): δ ppm 7.40-7.35 (m, 2H), 7.32 (t, J=7.5 Hz, 2H), 7.29-7.22 (m, 1H), 6.72 (d, J=15.9 Hz, 1H), 6.18 (dd, 1=15.9, 6.6 Hz, 1H), 4.63-4.51 (m, 1H), 4.37 (ddd, J=11.5, 7.3, 1.5 Hz, 1H), 4.29-4.13 (m, 2H), 3.87 (td, J=11.9, 2.9 Hz, 1H), 3.45 (dd, J=10.2, 1.0 Hz, 1H), 2.70 (ddd, J=14.5, 12.6, 7.6 Hz, 1H), 2.50 (ddd, J=14.6, 2.9, 1.6 Hz, 1H), 1.24 (td, J=7.1, 5.1 Hz, 3H) for keto form; 12.29 (s, 1H), 7.42-7.35 (m, 2H), 7.32 (t, J=7.5 Hz, 2H), 7.29-7.22 (m, 1H), 6.51 (d, J=16.0 Hz, 1H), 6.29 (dd, J=16.0, 5.6 Hz, 1H), 5.11 (d, J=5.6 Hz, 1H), 4.29-4.12 (m, 2H), 4.02-3.92 (m, 1H), 3.84-3.78 (m, 1H), 2.64-2.53 (m, 1H), 2.28 (dt, J=17.9, 3.9 Hz, 1H), 1.24 (td, J=7.1, 5.1 Hz, 3H) for enol form.

$^{13}$C NMR (125 MHz, CDCl$_3$): δ ppm (keto+enol) 201.3, 170.7, 170.7, 167.5, 136.8, 136.1, 133.7, 133.1, 128.7, 128.7, 128.6, 128.4, 127.9, 126.9, 126.7, 125.9, 99.3, 80.2, 71.2, 66.5, 63.6, 61.4, 60.6, 59.0, 41.6, 29.1, 14.3, 14.3.

HRMS (ESI) calculated for $C_{16}H_{18}O_4[M+Na]^+$: 297.1103, Found: 297.1105.

Chiral SFC (Chiralpak 1G-3, 10% MeOH in CO$_2$, flow rate=2.5 mL/min, λ=250 nm): 2.9 min (minor), 3.2 min (major).

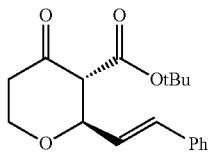

2ab

Colorless oil. (33.5 mg, 55% yield, 90:10 er.)

¹H NMR (500 MHz, CDCl₃): δ ppm 7.38 (t, J=6.4 Hz, 2H), 7.32 (t, J=7.5 Hz, 2H), 7.29-7.22 (m, 1H), 6.71 (d, J=15.9 Hz, 1H), 6.19 (dd, J=15.9, 6.6 Hz, 1H), 4.53 (ddd, J=10.1, 6.6, 0.9 Hz, 1H), 4.35 (ddd, J=11.5, 7.3, 1.6 Hz, 1H), 3.85 (td, J=11.9, 2.9 Hz, 1H), 3.34 (d, J=10.7 Hz, 4H), 2.73-2.63 (m, 1H), 2.47 (ddd, J=14.7, 2.9, 1.7 Hz, 1H), 1.45 (s, 9H) for keto form; 12.43 (s, 1H), 7.38 (t, 0.1=6.4 Hz, 2H), 7.32 (t, J=7.5 Hz, 2H), 7.29-7.23 (m, 1H), 6.52 (d, J=15.9 Hz, 1H), 6.27 (dd, J:=15.9, 5.9 Hz, 1H), 5.02 (d, J=5.8 Hz, 1H), 4.00-3.92 (m, 1H), 3.82-3.75 (m, 1H), 2.58-2.50 (m, 1H), 2.27 (dt, J=17.8, 3.9 Hz, 1H), 1.44 (s, 9H) for enol form.

HRMS (ESI) calculated for C₁₈H₂₂O₄[M+Na]⁺: 325.1416, Found: 325.1410.

Chiral SFC (Chiralpak IB-3, 2% MeOH in CO₂, flow rate=2.5 mL/min, λ=250 nm): 2.4 min (major), 2.8 min (minor).

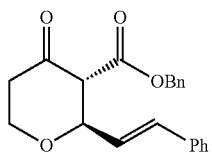

2ac

White solid. (35.8 mg, 56% yield, 84:16 e.r.)

¹H NMR (500 MHz, CDCl₃): δ ppm 7.33-7.27 (m, 7H), 7.27-7.22 (m, 3H), 6.65 (dd, J=15.9, 1.0 Hz, 1H), 6.13 (dd, J=15.9, 6.7 Hz, 1H), 5.19 (s, 2H), 4.58 (dd, J=10.2, 6.7 Hz, 1H), 4.37 (ddd, J=11.4, 7.3, 1.2 Hz, 1H), 3.87 (td, J=11.9, 2.8 Hz, 1H), 3.51 (d, J=10.3 Hz, 1H), 2.75-2.63 (m, 1H), 2.50 (ddd, J=14.8, 2.8, 1.6 Hz, 1H).

HRMS (ESI) calculated for C₂₁H₂₀O₄[M+Na]⁺: 359.1259, Found: 359.1260.

Chiral SFC (Chiralpak IB-3, 2% MeOH in CO₂, flow rate=2.5 mL/min, λ=210 nm): 6.5 min (major), 6.8 min (minor).

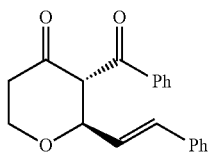

2ad

White solid. (42.3 mg, 69% yield)

¹H NMR (500 MHz, CDCl₃): δ ppm 7.84 (d, J=7.6 Hz, 2H), 7.55 (t, J=7.4 Hz, 1H), 7.44 (t, J=7.6 Hz, 2H), 7.35-7.09 (m, 5H), 6.71 (d, J=15.9 Hz, 1H), 6.13 (dd, J=16.0, 6.0 Hz, 1H), 4.89 (dd, J=9.7, 6.1 Hz, 1H), 4.53-4.32 (m, 2H), 3.96 (td, J=11.9, 3.0 Hz, 1H), 2.89-2.76 (m, 1H), 2.55 (d, J=14.7 Hz, 1H).

¹³C NMR (125 MHz, CDCl₃): δ ppm 203.7, 196.4, 137.6, 136.2, 133.7, 133.2, 128.9, 128.7, 128.5, 128.2, 126.8, 126.3, 80.3, 66.4, 64.1, 42.3.

HRMS (ESI) calculated for C₂₀H₁₅O₃ [M+Na]⁺: 329.1154, Found: 329.1150.

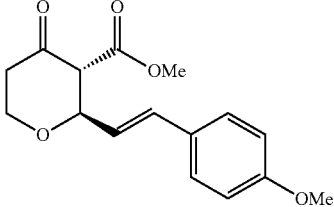

2b

Yellow solid. (34.8 mg, 60% yield, 78:22 e.r.)

¹H NMR (500 MHz, CDCl₃): δ ppm 7.31 (d, J=8.6 Hz, 2H), 6.85 (d, J=8.6 Hz, 2H), 6.65 (d, J=15.9 Hz, 1H), 6.03 (dd, J=15.9, 6.8 Hz, 1H), 4.55 (dd, J=9.8, 7.1 Hz, 1H), 4.37 (dd, J=10.9, 6.8 Hz, 1H), 3.85 (td, J=12.0, 2.6 Hz, 1H), 3.81 (s, 3H), 3.73 (s, 3H), 3.47 (d, J=10.1 Hz, 1H), 2.69 (td, J=13.4, 12.4, 7.4 Hz, 1H), 2.50 (d, J=14.4 Hz, 1H).

¹³C NMR (125 MHz, CDCl₃): δ ppm 201.4, 168.0, 159.9, 133.4, 128.8, 128.2, 123.5, 114.2, 80.5, 66.4, 63.7, 55.5, 52.4, 41.6.

HRMS (ESI) calculated for C₁₆H₁₈O₅ [M+Na]⁺: 313.1052, Found: 313.1055.

Chiral SFC (Chiralpak IG-3, 5% MeOH in C0₂, flow rate=2.5 mL/min, λ=250 nm): 9.1 min (major), 8.5 min (minor).

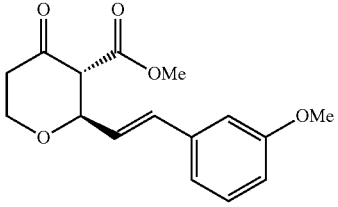

2c

Yellow oil. (45.1 mg, 78% yield, 96:4 e.r.)

¹H NMR (500 MHz, CDCl₃): δ ppm 7.24 (t, J=7.9 Hz, 1H), 6.98 (ddt, J=9.0, 7.7, 1.2 Hz, 1H), 6.92 (dt, J=11.9, 2.0 Hz, 1H), 6.82 (tdd, J=8.1, 2.6, 0.9 Hz, 1H), 6.68 (d, J=15.9 Hz, 1H), 6.16 (dd, J=15.9, 6.6 Hz, 1H), 4.58 (dd, J=10.6, 7.0 Hz, 1H), 4.38 (ddd, J=11.6, 7.3, 1.7 Hz, 1H), 3.90-3.84 (m, 1H), 3.81 (s, 3H), 3.74 (s, 3H), 3.47 (d, J=10.2 Hz, 1H), 2.76-2.65 (m, 1H), 2.54-2.45 (m, 1H) for keto form; 12.21 (s, 1H), 7.24 (t, J=7.9 Hz, 1H), 6.98 (ddt, J=9.0, 7.7, 1.2 Hz, 1H), 6.92 (dt, J=11.9, 2.0 Hz, 1H), 6.82 (tdd, J=8.1, 2.6, 0.9 Hz, 1H), 6.47 (d, J=16.0 Hz, 1H), 6.28 (dd, J=16.0, 5.4 Hz, 1H), 5.12 (d, J=5.2 Hz, 1H), 4.01-3.92 (m, 1H), 3.82 (s, 3H), 3.80-3.78 (m, 1H), 3.74 (s, 3H), 2.63-2.55 (m, 1H), 2.27 (dt, J=18.0, 3.5 Hz, 1H) for enol form.

¹³C NMR (125 MHz, CDCl₃): δ ppm 201.1, 167.8, 137.4, 133.4, 129.6, 126.0, 119.4, 113.9, 112.1, 80.0, 66.4, 63.4, 55.3, 52.3, 41.5 for keto form; 171.0, 170.7, 159.8, 138.1, 132.9, 129.6, 128.7, 119.3, 113.6, 111.9, 99.0, 70.7, 58.6, 51.6, 29.0 for enol form.

HRMS (ESI) calculated for C₁₆H₁₈O₅ [M+Na]⁺: 313.1052, Found: 313.1049.

Chiral SFC (Chiralpak ID-3, 10% MeOH in CO2, flow rate=2.5 mL/min, λ=250 nm): 3.1 min (major), 1.7 min (minor).

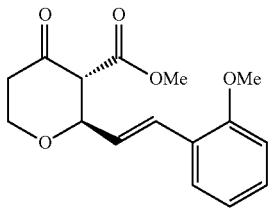

2d

Yellow oil. (40.9 mg, 70% yield, 92:8 e.r.)

$^1$H NMR (500 MHz, CDCl$_3$): δ ppm 7.48-7.37 (m, 1H), 7.25-7.20 (m, 1H), 7.02 (d, J=16.0 Hz, 1H), 6.92 (t, J=7.4 Hz, 1H), 6.87 (d, J=8.3 Hz, 1H), 6.20 (dd, J=16.1, 6.7 Hz, 1H), 4.58 (dd, J=10.5, 6.3 Hz, 1H), 4.38 (ddd, J=11.6, 7.3, 1.7 Hz, 1H), 3.89-3.85 (m, 1H), 3.84 (s, 3H), 3.74 (s, 3H), 3.49 (d, J=10.2 Hz, 1H), 2.76-2.65 (m, 1H), 2.50 (dt, J=14.7, 2.6 Hz, 1H) for keto form; 12.22 (s, 1H), 7.48-7.37 (m, 1H), 7.25-7.20 (m, 1H), 6.92 (t, J=7.4 Hz, 1H), 6.87 (d, J=8.3 Hz, 1H), 6.82 (d, J=16.1 Hz, 1H), 6.29 (dd, J=16.1, 5.5 Hz, 1H), 5.12 (d, J=5.5 Hz, 1H), 4.06-3.95 (m, 1H), 3.84 (s, 3H), 3.83-3.78 (m, 1H), 3.74 (s, 3H), 2.63-2.54 (m, 1H), 2.27 (dt, J=18.0, 3.5 Hz, 1H) for enol form.

$^{13}$C NMR (125 MHz, CDCl$_3$): δ ppm (keto+enol) 201.5, 171.2, 170.7, 168.0, 157.2, 157.0, 129.5, 129.0, 129.0, 128.9, 128.2, 127.5, 127.4, 127.2, 126.4, 125.9, 125.1, 120.8, 120.7, 111.0, 111.0, 99.5, 80.7, 71.3, 66.4, 63.8, 58.7, 55.6, 52.3, 51.6, 41.6, 29.1.

HRMS (ESI) calculated for C$_{16}$H$_{18}$O$_3$ [M+Na]$^+$: 313.1052, Found: 313.1053.

Chiral SFC (Chiralpak IB-3, 2% MeOH in CO$_2$, flow rate=2.5 mL/min, λ=250 nm): 4.4 min (major), 3.6 min (minor) and 4.9 min (major), 6.5 min (minor) (keto/enol forms were not assigned).

2e

White solid. (46.3 mg, 84% yield, 95:5 e.r.)

$^1$H NMR (500 MHz, CDCl$_3$): δ ppm 7.31-7.24 (m, 2H), 7.13 (d, J=7.7 Hz, 2H), 6.68 (d, J=15.9 Hz, 1H), 6.12 (dd, J=15.9, 6.7 Hz, 1H), 4.57 (dd, J=10.8, 6.8 Hz, 1H), 4.37 (ddd, J=11.6, 7.3, 1.7 Hz, 1H), 3.90-3.83 (m, 1H), 3.73 (s, 3H), 3.47 (d, J=10.1 Hz, 1H), 2.75-2.65 (m, 1H), 2.53-2.46 (m, 1H), 2.34 (s, 3H) for keto form; 12.21 (s, 1H), 7.31-7.24 (m, 2H), 7.13 (d, J=7.7 Hz, 2H), 6.46 (d, J=16.0 Hz, 1H), 6.24 (dd, J=16.0, 5.4 Hz, 1H), 5.11 (d, J=5.5 Hz, 1H), 3.99-3.91 (m, 1H), 3.82-3.77 (M, 1H), 3.73 (s, 3H), 2.63-2.54 (m, 1H), 2.34 (s, 3H), 2.26 (dt, J=18.0, 3.7 Hz, 1H) for enol form.

$^{13}$C NMR (125 MHz, CDCl$_3$): δ ppm (keto+enol) 201.4, 171.2, 170.8, 168.0, 138.4, 137.9, 133.9, 133.7, 133.3, 133.1, 129.5, 129.4, 127.5, 126.8, 126.7, 124.7, 99.3, 80.3, 70.9, 66.5, 63.7, 58.7, 52.4, 51.7, 41.6, 29.1, 21.4, 21.4.

HRMS (ESI) calculated for C$_{16}$H$_{18}$O$_4$[M+Na]$^+$: 297.1103, Found: 297.1103.

Chiral SFC (Chiralpak IB-3, 2% MeOH in CO$_2$, flow rate=2.5 mL/min, λ=250 nm): 2.3 min (major), 2.0 min (minor) and 2.6 min (major), 2.9 min (minor) (keto/enol forms were not assigned).

2f

White solid. (39.2 mg, 71% yield, 95:5 e.r.)

$^1$H NMR (500 MHz, CDCl$_3$): δ ppm 7.24-7.16 (m, 3H), 7.12-7.04 (m, 1H), 6.68 (d, J=15.9 Hz, 1H), 6.15 (dd, J=15.9, 6.7 Hz, 1H), 4.57 (ddd, J=10.2, 6.7, 1.1 Hz, 1H), 4.37 (ddd, J=11.6, 7.3, 1.7 Hz, 1H), 3.86 (td, J=12.0, 2.9 Hz, 1H), 3.74 (s, 3H), 3.47 (d, J=10.2 Hz, 1H), 2.74-2.66 (m, 1H), 2.54-2.48 (m, 1H), 2.35 (s, 3H) for keto form; 12.21 (s, 1H), 7.24-7.16 (m, 3H), 7.12-7.04 (m, 1H), 6.47 (d, J=16.0 Hz, 1H), 6.28 (dd, J=16.0, 5.4 Hz, 1H), 5.12 (d, J=5.3 Hz, 1H), 4.02-3.91 (m, 1H), 3.83-3.78 (m, 1H), 3.74 (s, 3H), 2.64-2.54 (m, 1H), 2.35 (s, 3H), 2.26 (dt, J=18.0, 3.5 Hz, 1H) for enol form.

$^{13}$C NMR (125 MHz, CDCl$_3$): δ ppm (keto+enol) 201.2, 171.0, 170.7, 167.9, 138.2, 138.2, 136.5, 135.9, 133.7, 133.1, 129.1, 128.6, 128.5, 128.5, 128.2, 127.5, 127.4, 125.5, 123.9, 123.8, 99.1, 80.1, 70.7, 66.3, 63.5, 58.5, 52.3, 51.6, 41.5, 29.0, 21.4, 21.4.

HRMS (ESI) calculated for C$_{16}$H$_{18}$O$_4$ [M+Na]$^+$: 297.1103, Found: 297.1103.

Chiral SFC (Chiralpak IG-3, 10% MeOH in CO$_2$, flow rate=2.5 mL/min, λ=250 nm): 3.9 min (major), 2.6 min (minor) and 6.5 min (major), 16.0 min (minor) (keto/enol forms were not assigned).

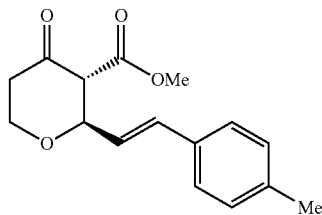

2g

Yellow oil. (44.4 mg, 81% yield, 96:4 e.r.)

$^1$H NMR (500 MHz, CDCl$_3$): δ ppm 7.42-7.38 (m, 1H), 7.20-7.10 (m, 3H), 6.93 (d, J=15.8 Hz, 1H), 6.04 (dd, J=15.8, 6.7 Hz, 1H), 4.60 (dd, J=10.2, 6.7 Hz, 1H), 4.39 (ddd, J=11.6, 7.3, 1.7 Hz, 1H), 3.90-3.84 (m, 1H), 3.75 (s, 3H), 3.49 (d, J=10.2 Hz, 1H), 2.76-2.66 (m, 1H), 2.54-2.48 (m, 1H), 2.33 (s, 3H) for keto form; 12.21 (s, 1H), 7.44-7.42 (m, 1H), 7.20-7.10 (m, 3H), 6.74 (d, J=15.8 Hz, 1H), 6.13 (dd, J=15.8, 5.6 Hz, 1H), 5.12 (d, J=5.5 Hz, 1H), 4.04-3.96 (m, 1H), 3.84-3.80 (m, 1H), 3.75 (s, 3H), 2.64-2.55 (m, 1H), 2.33 (s, 3H), 2.29 (dt, J=18.0, 3.7 Hz, 1H) for enol form.

$^{13}$C NMR (125 MHz, CDCl$_3$): δ ppm (keto+enol) 201.3, 171.1, 170.8, 168.0, 136.1, 136.0, 135.6, 135.4, 131.8, 131.1, 130.4, 130.4, 130.0, 128.3, 127.8, 127.4, 126.3, 126.3, 126.1, 126.0, 99.3, 80.4, 71.2, 66.5, 63.7, 58.8, 52.4, 51.7, 41.6, 29.1, 19.9, 19.9.

HRMS (ESI) calculated for C$_{16}$H$_{18}$O$_4$[M+Na]$^+$: 297.1103, Found: 297.1101.

Chiral SFC (Chiralpak IC-3, 1.5% MeOH in C02, flow rate=2.5 mL/min, λ=250 nm): 5.6 min (major), 3.7 min (minor) and 6.5 min (major), 7.3 min (minor) (keto/enol forms were not assigned).

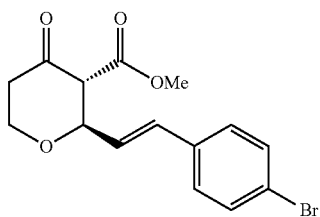

2h

White solid. (40.2 mg, 59% yield, 94:6 e.r.)

$^1$H NMR (500 MHz, CDCl$_3$): δ ppm 7.48-7.41 (m, 2H), 7.27-7.21 (m, 2H), 6.66 (d, J=15.9 Hz, 1H), 6.16 (dd, J=15.9, 6.5 Hz, 1H), 4.57 (dd, J=10.7, 6.1 Hz, 1H), 4.38 (ddd, J=11.7, 7.4, 1.7 Hz, 1H), 3.90-3.84 (m, 1H), 3.74 (s, 3H), 3.46 (d, J=10.3 Hz, 1H), 2.76-2.66 (m, 1H), 2.51 (ddd, J=14.6, 2.6, 1.6 Hz, 1H) for keto form; 12.20 (s, 1H), 7.48-7.41 (m, 2H), 7.27-7.21 (m, 2H), 6.45 (d, J=16.0 Hz, 1H), 6.28 (dd, J=16.0, 5.3 Hz, 1H), 5.10 (d, J=5.3 Hz, 1H), 3.99-3.91 (m, 1H), 3.84-3.78 (m, 1H), 3.74 (s, 3H), 2.64-2.54 (m, 1H), 2.28 (dt, J=18.0, 3.6 Hz, 1H) for enol form.

$^{13}$C NMR (125 MHz, CDCl$_3$): δ ppm (keto+enol) 201.1, 171.0, 170.9, 167.9, 135.7, 135.0, 132.4, 131.9, 131.8, 131.8, 129.4, 128.4, 128.3, 126.6, 122.4, 121.7, 99.0, 80.0, 70.8, 66.5, 63.5, 58.9, 52.4, 51.8, 41.6, 29.1.

HRMS (ESI) calculated for C$_{15}$H$_{15}$BrO$_4$[M+Na]$^+$: 361.0051, Found: 361.0047.

Chiral SFC (Chiralpak IG-3, 10% MeOH in C02, flow rate=2.5 mL/min, λ=250 nm): 5.7 min (major), 5.2 min (minor).

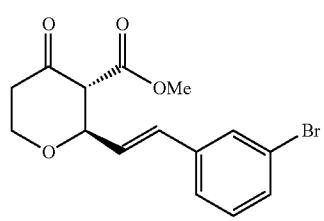

2i

White solid. (37.5 mg, 55% yield, 95:5 e.r.)

$^1$H NMR (500 MHz, CDCl$_3$): δ ppm 7.57-7.50 (m, 1H), 7.42-7.35 (m, 1H), 7.29 (t, J=8.3 Hz, 1H), 7.19 (td, J=7.8, 1.7 Hz, 1H), 6.65 (d, J=15.9 Hz, 1H), 6.17 (dd, J=15.9, 6.4 Hz, 1H), 4.58 (ddd, J=10.3, 6.4, 1.2 Hz, 1H), 4.38 (ddd, J=11.6, 7.3, 1.7 Hz, 1H), 3.89-3.83 (m, 1H), 3.76 (s, 3H), 3.45 (d, J=10.3 Hz, 1H), 2.76-2.65 (m, 1H), 2.54-2.48 (m, 1H) for keto form; 12.20 (s, 1H), 7.57-7.50 (m, 1H), 7.42-7.35 (m, 1H), 7.29 (t, J=8.3 Hz, 1H), 7.19 (td, J=7.8, 1.7 Hz, 1H), 6.44 (d, J=16.0 Hz, 1H), 6.29 (dd, J=16.0, 5.3 Hz, 1H), 5.11 (d, J=5.2 Hz, 1H), 3.97-3.91 (m, 1H), 3.83-3.79 (m, 1H), 3.75 (s, 3H), 2.63-2.54 (m, 1H), 2.27 (dt, J=18.0, 3.6 Hz, 1H) for enol form.

$^{13}$C NMR (125 MHz, CDCl$_3$): δ ppm (keto+enol) 201.0, 171.0, 171.0, 167.9, 138.9, 138.2, 132.0, 131.5, 131.3, 130.8, 130.3, 130.2, 130.2, 129.7, 129.6, 127.4, 125.6, 125.4, 123.0, 122.9, 99.0, 79.8, 70.7, 66.5, 63.4, 58.9, 52.5, 51.8, 41.6, 29.1.

HRMS (ESI) calculated for C$_{15}$H$_{15}$BrO$_4$[M+Na]$^+$: 361.0051, Found: 361.0044.

Chiral SFC (Chiralpak IG-3, 10% MeOH in CO$_2$, flow rate=2.5 mL/min, λ=250 nm): 4.9 min (major), 4.1 min (minor).

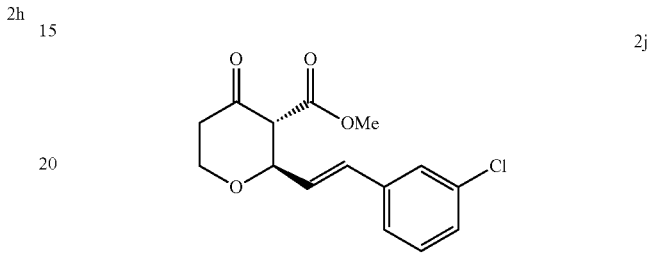

2j

White solid. (40.1 mg, 68% yield, 96:4 e.r.)

$^1$H NMR (500 MHz, CDCl$_3$): δ ppm 7.38 (s, 1H), 7.29-7.20 (m, 3H), 6.68 (d, J=15.9 Hz, 1H), 6.19 (dd, J=15.9, 6.4 Hz, 1H), 4.59 (ddd, J=10.3, 6.4, 1.2 Hz, 1H), 4.40 (ddd, J=11.6, 7.3, 1.7 Hz, 1H), 3.91-3.85 (m, 1H), 3.77 (s, 3H), 3.47 (d, J=10.3 Hz, 1H), 2.77-2.67 (m, 1H), 2.53 (ddd, J=14.7, 2.9, 1.6 Hz, 1H) for keto form; 12.22 (s, 1H), 7.40 (s, 1H), 7.29-7.20 (m, 3H), 6.47 (d, J=16.0 Hz, 1H), 6.32 (dd, J=16.0, 5.3 Hz, 1H), 5.13 (d, J=5.2 Hz, 1H), 4.00-3.93 (m, 1H), 3.85-3.81 (m, 1H), 3.77 (s, 3H), 2.65-2.56 (m, 1H), 2.29 (dt, J=18.0, 3.6 Hz, 2H) for enol form.

$^{13}$C NMR (125 MHz, CDCl$_3$): δ ppm (keto+enol) 201.0, 171.0, 171.0, 167.9, 138.7, 137.9, 134.8, 134.7, 132.2, 131.6, 130.2, 130.0, 129.9, 128.4, 127.9, 127.3, 126.8, 126.7, 125.1, 125.0, 99.0, 79.8, 70.8, 66.5, 63.4, 58.9, 52.5, 51.8, 41.6, 29.1.

HRMS (ESI) calculated for C$_{15}$H$_{15}$ClO$_4$[M+Na]$^+$: 317.0557, Found: 317.0549.

Chiral SFC (Chiralpak 1G-3, 10% MeOH in CO$_2$, flow rate=2.5 mL/min, λ=250 nm): 4.0 min (major), 3.3 min (minor).

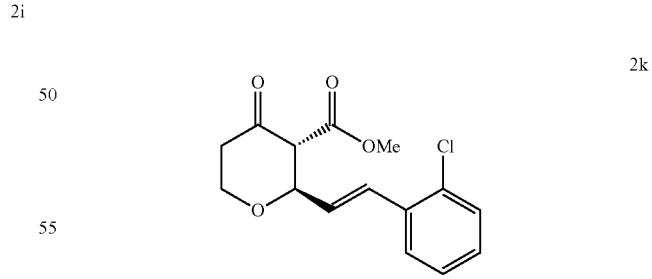

2k

Yellow oil. (34.0 mg, 58% yield, 97:3 e.r.)

$^1$H NMR (500 MHz, CDCl$_3$): δ ppm 7.50-7.47 (m, 1H), 7.35 (d, J=7.0 Hz, 1H), 7.25-7.16 (m, 2H), 7.09 (d, J=15.9 Hz, 1H), 6.15 (dd, J=15.9, 6.4 Hz, 1H), 4.62 (dd, J=10.3, 6.4 Hz, 1H), 4.39 (dd, J=11.4, 7.1 Hz, 1H), 3.91-3.85 (m, 1H), 3.77 (s, 3H), 3.48 (d, J=10.4 Hz, 1H), 2.77-2.67 (m, 1H), 2.54-2.48 (m, 1H) for keto form; 12.22 (s, 1H), 7.54-7.50 (m, 1H), 7.35 (d, J=7.0 Hz, 1H), 7.25-7.16 (m, 2H), 6.91 (dd, J=16.0, 1.5 Hz, 1H), 6.22 (dd, J=15.9, 5.6 Hz, 1H), 5.14 (d, J=5.5 Hz, 1H), 4.03-3.96 (m, 1H), 3.85-3.81 (m, 1H), 3.76 (a, 3H), 2.63-2.54 (m, 1H), 2.30 (dt, J=17.9, 3.7 Hz, 1H) for enol form.

$^{13}$C NMR (125 MHz, CDCl$_3$): δ ppm (keto+enol) 201.1, 171.0, 170.9, 167.9, 135.2, 134.4, 133.6, 133.3, 131.4, 129.9, 129.8, 129.5, 129.4, 128.9, 128.8, 127.2, 127.1, 127.0, 99.0, 79.9, 71.1, 66.6, 63.6, 59.0, 52.5, 51.7, 41.6, 29.1.

HRMS (ESI) calculated for C$_{15}$H$_{15}$ClO$_4$[M+Na]$^+$: 317.0557, Found: 317.0554.

Chiral SFC (Chiralpak IG-3, 10% MeOH in CO$_2$, flow rate=2.5 mL/min, λ=250 nm): 2.7 min (major), 2.4 min (minor).

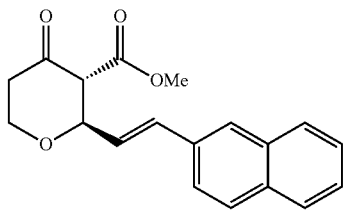

2l

Yellow solid. (48.1 mg, 77% yield, 94:6 e.r.)

$^1$H NMR (500 MHz, CDCl$_3$): δ ppm 7.87-7.72 (m, 4H), 7.58 (dd, J=8.6, 1.7 Hz, 1H), 7.51-7.41 (m, 2H), 6.88 (d, J=15.9 Hz, 1H), 6.30 (dd, J=15.9, 6.6 Hz, 1H), 4.65 (ddd, J=10.2, 6.6, 1.1 Hz, 1H), 4.40 (ddd, J=11.6, 7.3, 1.7 Hz, 1H), 3.92-3.86 (m, 1H), 3.75 (s, 3H), 3.53 (d, J=10.2 Hz, 1H), 2.77-2.68 (m, 1H), 2.56-2.48 (m, 1H) for keto form; 12.25 (s, 1H), 7.87-7.72 (m, 4H), 7.62 (dd, J=8.6, 1.8 Hz, 1H), 7.51-7.41 (m, 2H), 6.68 (d, J=16.0 Hz, 1H), 6.42 (dd, J=15.9, 5.4 Hz, 1H), 5.18 (d, J=5.3 Hz, 1H), 4.01 (ddd, J=11.7, 9.6, 4.3 Hz, 1H), 3.86-3.81 (m, 1H), 3.76 (s, 3H), 2.66-2.56 (m, 1H), 2.30 (dt, J=18.0, 3.6 Hz, 1H) for enol form.

$^{13}$C NMR (125 MHz, CDCl$_3$): δ ppm (keto+enol) 201.3, 171.1, 170.9, 168.0, 134.2, 133.8, 133.7, 133.6, 133.5, 133.4, 133.2, 128.9, 128.4, 128.4, 128.2, 128.1, 127.8, 127.8, 127.4, 126.9, 126.6, 126.5, 126.4, 126.1, 126.1, 123.7, 123.6, 99.2, 80.3, 71.0, 66.5, 63.6, 58.8, 52.4, 51.8, 41.7, 29.1.

HRMS (ESI) calculated for C$_{19}$H$_{18}$O$_4$[M+Na]$^+$: 333.1103, Found: 333.1101.

Chiral SFC (Chiralpak IG-3, 10% MeOH in CO$_2$, flow rate:=2.5 mL/min, λ=250 nm): 10.6 min (major), 9.3 min (minor).

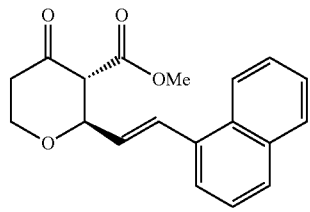

2m

Yellow solid. (49.4 mg, 80% yield, 95:5 e.r.)

$^1$H NMR (500 MHz, CDCl$_3$): δ ppm 8.05 (d, J=8.0 Hz, 1H), 7.88-7.84 (m, 1H), 7.80 (t, J=8.3 Hz, 1H), 7.56 (d, J=7.1 Hz, 1H), 7.55-7.42 (m, 4H), 6.20 (dd, J=15.6, 6.6 Hz, 1H), 4.72 (ddd, J=10.4, 6.6, 1.2 Hz, 1H), 4.43 (ddd, J=11.6, 7.3, 1.6 Hz, 1H), 3.94-3.89 (m, 1H), 3.76 (s, 3H), 3.56 (d, J=10.3 Hz, 1H), 2.79-2.70 (m, 1H), 2.54 (ddd, J=14.7, 2.8, 1.6 Hz, 1H) for keto form; 12.26 (s, 1H), 8.05 (d, J=8.0 Hz, 1H), 7.88-7.84 (m, 1H), 7.80 (t, J=8.3 Hz, 1H), 7.60 (d, J=7.1 Hz, 1H), 7.55-7.42 (m, 3H), 7.30 (d, J=15.7 Hz, 1H), 6.30 (dd, J=15.7, 5.5 Hz, 1H), 5.22 (d, J=5.4 Hz, 1H), 4.13-4.04 (m, 1H), 3.89-3.85 (m, 1H), 3.79 (s, 3H), 2.68-2.59 (m, 1H), 2.34 (dt, J=18.0, 3.6 Hz, 1H) for enol form.

$^{13}$C NMR (125 MHz, CDCl$_3$): δ ppm (keto+enol) 201.2, 171.2, 170.9, 168.1, 134.7, 134.0, 133.7, 133.7, 131.8, 131.3, 131.3, 131.2, 130.4, 129.1, 128.7, 128.2, 126.4, 126.2, 126.1, 125.9, 125.7, 125.7, 124.3, 124.1, 123.8, 99.3, 80.4, 71.3, 66.6, 63.7, 59.0, 52.4, 51.7, 41.6, 29.2.

HRMS (ESI) calculated for C$_{19}$H$_{18}$O$_4$[M+Na]$^+$: 333.1103, Found: 333.1101.

Chiral SFC (Chiralpak ID-3, 10% MeOH in CO$_2$, flow rate=2.5 mL/min, λ=250 nm): 2.6 min (major), 2.0 min (minor).

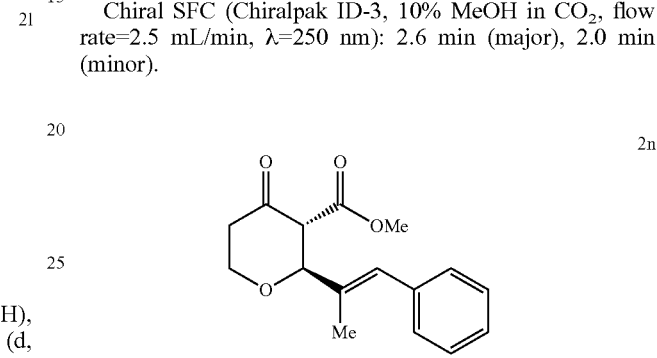

2n

White solid. (47.5 mg, 87% yield, 97:3 e.r.)

$^1$H NMR (500 MHz, CDCl$_3$): δ ppm 7.33 (t, J=7.6 Hz, 2H), 7.27-7.21 (m, 3H), 6.55 (s, 1H), 4.48 (d, J=10.3 Hz, 1H), 4.37 (ddd, J=11.5, 7.4, 1.6 Hz, 1H), 3.87 (td, J=11.8, 2.8 Hz, 1H), 3.72 (s, 3H), 3.67 (d, J=10.7 Hz, 1H), 2.74-2.62 (m, 1H), 2.50 (ddd, J=14.9, 2.8, 1.5 Hz, 1H), 1.95 (s, 3H).

$^{13}$NMR (125 MHz, CDCl$_3$): δ ppm 201.7, 167.9, 136.8, 134.3, 130.1, 129.1, 128.3, 127.2, 85.7, 66.4, 61.9, 52.4, 41.5, 13.0.

HRMS (ESI) calculated for C$_{16}$H$_{18}$NO$_4$[M+Na]$^+$: 297.1103, Found: 297.1104.

Chiral SFC (Chiralpak ID-3, 1% MeOH in CO$_2$, flow rate=2.5 mL/,min, λ=250 nm): 4.0 min (major), 3.3 min (minor).

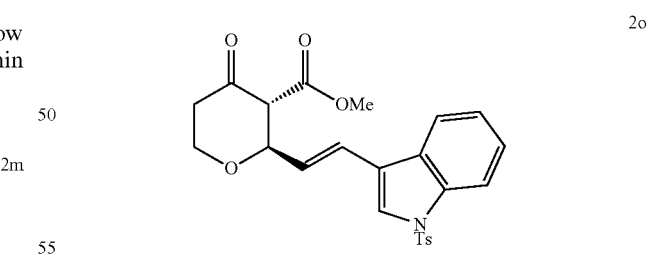

2o

White foam solid. (49.7 mg, 55% yield, 87:13 e.r.)

$^1$H NMR (500 MHz, CDCl$_3$): δ ppm 7.99 (dd, J=8.3, 3.6 Hz, 1H), 7.77 (dd, J=8.4, 6.2 Hz, 2H), 7.68 (d, J=7.9 Hz, 1H), 7.60 (d, J=6.0 Hz, 1H), 7.36-7.31 (m, 1H), 7.29-7.25 (m, 1H), 7.22 (d, J=8.2 Hz, 2H), 6.79 (d, J=16.1 Hz, 1H), 6.23 (dd, J=16.1, 6.6 Hz, 1H), 4.58 (ddd, J=10.2, 6.6 Hz, 1H), 4.39 (ddd, J=11.6, 7.3, 1.7 Hz, 1H), 3.87 (td, J=11.9, 2.8 Hz, 1H), 3.75 (s, 3H), 3.50 (d, J=10.2 Hz, 1H), 2.75-2.67 (m, 1H), 2.52 (dq, J=14.6, 1.7 Hz, 1H), 2.34 (s, 3H) for keto form; 12.21 (s, 1H), 7.99 (dd, J=8.3, 3.6 Hz, 1H), 7.77 (dd, J=8.4, 6.2 Hz, 2H), 7.71 (d, J=7.8 Hz, 1H), 7.60 (d, J=6.0 Hz, 1H), 7.36-7.31 (m, 1H), 7.29-7.25 (m, 1H), 7.22 (d, J=8.2 Hz, 2H), 6.58 (d, J=16.2 Hz, 1H), 6.36 (dd, J=16.2, 5.4 Hz, 1H), 5.13 (d, J=5.5 Hz, 1H), 4.02-3.94 (m, 1H), 3.84-3.79 (m, 1H), 3.75 (s, 3H), 2.63-2.55 (m, 1H), 2.34 (s, 3H), 2.30 (dt, J=18.0, 3.7 Hz, 1H) for enol form.

$^{13}$C NMR (125 MHz, CDCl$_3$): δ ppm (keto+enol) 201.1, 171.1, 170.9, 168.0, 145.3, 145.2, 135.6, 135.6, 135.3, 135.2, 130.1, 130.1, 129.8, 129.1, 128.9, 127.0, 126.9, 125.2, 125.1, 125.0, 124.5, 124.4, 123.8, 123.7, 123.6, 120.5, 120.4, 120.0, 119.3, 113.9, 113.9, 99.0, 80.4, 71.2, 66.5, 63.6, 58.9, 52.5, 51.8, 41.7, 29.1, 21.7.

HRMS (ESI) calculated for C$_{24}$H$_{23}$NO$_6$S [M+Na]$^+$: 476.1144, Found: 476.1138.

Chiral SFC (Chiralpak IC-3, 10% MeOH in CO$_2$, flow rate=2.5 mL/min, λ=250 n): 5.4 min (minor), 5.9 min (major) and 10.5 min (major), 12.1 min (minor) (keto/enol forms were not assigned).

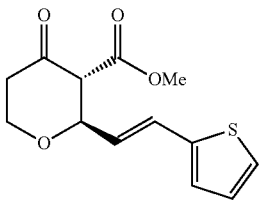

2p

Yellow oil. (36.5 mg, 69% yield, 88:12 e.r.)

$^1$H NMR (500 MHz, CDCl$_3$): δ ppm 7.19 (d, J=5.0 Hz, 1H), 7.02-6.93 (m, 2H), 6.83 (d, J=15.7 Hz, 1H), 6.00 (dd, J=15.7, 6.6 Hz, 1H), 4.54 (ddd, J=10.3, 6.6, 1.2 Hz, 1H), 4.36 (ddd, J=11.6, 7.2, 1.7 Hz, 1H), 3.84 (td, J=11.8, 2.8 Hz, 1H), 3.75 (s, 3H), 3.46 (d, J=10.2 Hz, 1H), 2.74-2.65 (m, 1H), 2.49 (ddd, J=14.7, 2.8, 1.7 Hz, 1H) for keto form; 12.20 (s, 1H), 7.18-7.15 (m, 1H), 7.02-6.93 (m, 2H), 6.62 (d, J=15.8 Hz, 1H), 6.13 (dd, J=15.8, 5.4 Hz, 1H), 5.09 (d, J=5.3 Hz, 1H), 3.99-3.91 (m, 1H), 3.81-3.78 (m, 1H), 3.75 (s, 3H), 2.63-2.54 (m, 1H), 2.25 (ddd, J=18.0, 4.3, 2.8 Hz, 1H) for enol form.

$^{13}$C NMR (125 MHz, CDCl$_3$): δ ppm (keto+enol) 201.2, 171.0, 170.9, 167.9, 141.9, 141.0, 128.2, 127.6, 127.5, 127.1, 126.8, 126.3, 126.3, 125.4, 125.1, 124.7, 99.0, 79.9, 70.6, 66.4, 63.5, 58.7, 52.4, 51.8, 41.6, 29.0.

HRMS (ESI) calculated for C$_{13}$H$_{14}$O$_4$ [M+Na]$^+$: 289.0510, Found: 289.0507.

Chiral SFC (Chiralpak IG-3, 30% MeOH in CO$_2$, flow rate=2.5 mL/min, λ=250 nm): 2.1 min (minor), 2.4 min (major).

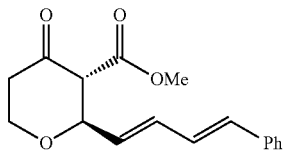

2q

Yellow solid. (28.8 mg, 50% yield, 91:9 e.r.)

$^1$H NMR (500 MHz, CDCl$_3$): δ ppm 7.39 (d, J=7.3 Hz, 2H), 7.32 (t, J=7.6 Hz, 2H), 7.26-7.21 (m, 1H), 6.73 (dd, J=15.6, 10.5 Hz, 1H), 6.60 (d, J=15.6 Hz, 1H), 6.50 (dd, J=15.2, 10.4 Hz, 1H), 5.77 (dd, J=15.2, 6.7 Hz, 1H), 4.51 (ddd, J=10.2, 6.6, 1.1 Hz, 1H), 4.35 (ddd, J=11.6, 7.3, 1.7

Hz, 1H), 3.84 (td, J=11.9, 2.9 Hz, 1H), 3.76 (s, 3H), 3.43 (d, J=10.2 Hz, 1H), 2.73-2.63 (m, 1H), 2.49 (ddd, J=14.6, 2.9, 1.7 Hz, 1H).

$^{13}$C NMR (125 MHz, CDCl$_3$): δ ppm 201.3, 168.0, 136.9, 134.8, 134.0, 129.3, 128.8, 128.1, 127.6, 126.7, 79.9, 66.5, 63.6, 52.4, 41.6.

HRMS (ESI) calculated for C$_{17}$H$_{18}$O$_4$ [M+Na]$^+$: 309.1103, Found: 309.1100.

Chiral SFC (Chiralpak IG-3, 30% MeOH in C02, flow rate=2.5 mL/min, λ=250 nm): 4.0 min (minor), 5.3 min (major).

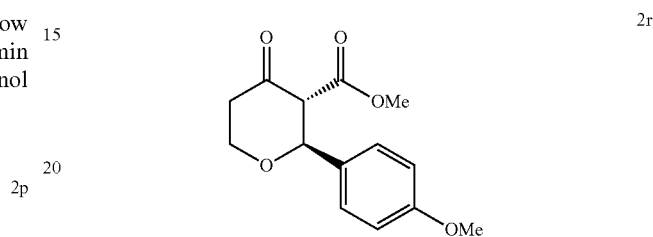

2r

White solid. (26.4 mg, 50% yield, 91:9 e.r., reaction for 20 h at −30° C.)

$^1$H NMR (500 MHz, CDCl$_3$): δ ppm 7.32 (d, J=8.7 Hz, 2H), 6.88 (d, J=8.7 Hz, 2H), 4.85 (d, J=10.4 Hz, 1H), 4.40 (ddd, J=11.6, 7.5, 1.5 Hz, 1H), 3.91 (td, J=12.2, 2.7 Hz, 1H), 3.80 (s, 3H), 3.67 (d, J=11.1 Hz, 1H), 3.61 (s, 3H), 2.84-2.72 (m, 1H), 2.58-2.50 (m, 1H).

$^{13}$C NMR (125 MHz, CDCl$_3$): δ ppm 201.6, 167.9, 160.0, 130.8, 128.3, 114.2, 81.7, 66.8, 65.0, 55.4, 52.2, 41.7.

HRMS (ESI) calculated for C$_{14}$H$_{16}$O$_5$ [M+Na]$^+$: 287.0895, Found: 287.0897.

Chiral SFC (Chiralpak IG-3, 20% MeOH in CO$_2$, flow rate=2.5 ml/min, λ=250 nm): 2.1 min (major), 1.7 min (minor).

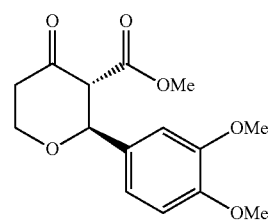

2s

White solid. (29.4 mg, 50% yield, 89:11 e.r., reaction for 4 h at −30° C.)

$^1$H NMR (500 MHz, CDCl$_3$): δ ppm 6.95-6.88 (m, 2H), 6.86-6.78 (m, 1H), 4.86 (d, J=10.4 Hz, 1H), 4.41 (ddd, J=11.6, 7.4, 1.5 Hz, 1H), 3.95-3.90 (m, 1H), 3.90 (s, 3H), 3.87 (s, 3H), 3.67 (d, J=10.4 Hz, 1H), 3.62 (s, 3H), 2.84-2.72 (m, 1H), 2.54 (ddd, J=14.6, 2.8, 1.5 Hz, 1H) for keto form; 12.25 (s, 1H), 6.95-6.88 (m, 2H), 6.86-6.78 (m, 1H), 5.45 (s, 1H), 3.89 (s, 3H), 3.87 (s, 3H), 3.74-3.70 (m, 2H), 3.59 (s, 3H), 2.64-2.58 (m, 1H), 2.34 (dt, J=18.0, 4.0 Hz, 1H) for enol form.

$^{13}$C NMR (125 MHz, CDCl$_3$): δ ppm (keto+enol) 201.4, 171.0, 170.9, 167.8, 149.3, 149.1, 148.9, 148.8, 133.5, 131.1, 120.6, 119.3, 111.5, 111.0, 110.3, 109.7, 99.3, 81.7, 73.1, 66.7, 64.9, 58.5, 55.9, 55.9, 52.1, 51.5, 41.5, 29.0.

HRMS (ESI) calculated for C$_{15}$H$_{18}$O$_6$ [M+Na]$^+$: 317.1001, Found: 317.1002.

Chiral SFC (Chiralpak IG-3, 10% MeOH in C02, flow rate=2.5 mL/min, λ=250 nm): 2.9 min (major), 2.6 min (minor).

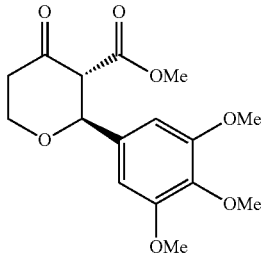

Colorless oil. (36.3 mg, 83% yield, 91:9 e.r., reaction for 45 h at −30° C.)

$^1$H NMR (500 MHz, CDCl$_3$): δ ppm 6.61 (s, 2H), 4.98-4.79 (m, 1H), 4.43 (ddd, J=11.6, 7.4, 1.5 Hz, 1H), 3.94-3.89 (m, 1H), 3.86 (s, 6H), 3.83 (s, 3H), 3.69-3.64 (m, 4H), 2.84-2.73 (m, 1H), 2.58-2.53 (m, 1H) for keto form; 12.26 (s, 1H), 6.52 (s, 2H), 5.42 (s, 1H), 3.85 (s, 6H), 3.84 (s, 3H), 3.79-3.70 (m, 2H), 3.61 (s, 3H), 2.62-2.58 (m, 1H), 2.44-2.37 (m, 1H) for enol form.

$^{13}$C NMR (125 MHz, CDCl$_3$): δ ppm (keto+enol) 201.3, 171.2, 171.1, 167.9, 153.5, 153.2, 138.4, 137.9, 136.8, 134.3, 105.6, 103.8, 102.5, 99.3, 81.9, 73.8, 66.8, 65.0, 61.0, 59.3, 56.3, 56.3, 52.3, 51.7, 41.6, 29.2.

HRMS (ESI) calculated for C$_{16}$H$_{20}$O$_7$ [M+Na]$^+$: 347.1107, Found: 347.1110.

Chiral SFC (Chiralpak IC-3, 10% MeOH in CO$_2$, flow rate=2.5 mL/min, λ=250 nm): 2.8 min (major), 3.7 min (minor) and 3.1 min (major), 4.2 min (minor) (keto/enol forms were not assigned).

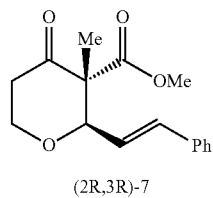 [SMILES: COC(=O)[C@@]1(C)C(=O)CCO[C@@H]1/C=C/c1ccccc1]

(2R,3R)-7

White solid (35.5 mg, 65% yield, >20:1 dr, 96:4 er).

$^1$H NMR (500 MHz, CDCl$_3$): δ ppm 7.36 (d, J=7.2 Hz, 2H), 7.32 (t, J=7.5 Hz, 2H), 7.29-7.23 (m, 1H), 6.71 (d, J=15.9 Hz, 1H), 6.01 (dd, J=15.9, 6.1 Hz, 1H), 4.82 (dd, J=6.1, 1.2 Hz, 1H), 4.35 (ddd, J=11.6, 7.4, 2.5 Hz, 1H), 3.90 (td, J=11.4, 3.7 Hz, 1H), 3.79 (s, 3H), 2.81 (ddd, J=15.2, 11.4, 7.4 Hz, 1H), 2.44 (ddd, J=15.2, 3.7, 2.4 Hz, 1H), 1.41 (s, 3H).

$^{13}$C NMR (125 MHz, CDCl$_3$): δ ppm 205.6, 171.2, 136.3, 134.0, 128.7, 128.3, 126.8, 123.2, 81.7, 66.1, 63.3, 52.6, 38.2, 15.1.

HRMS (ESI) calculated for Ci(H$_{16}$H$_{18}$O$_4$[M+Na]$^+$: 297.1103, Found: 297.1108.

Chiral SFC (Chiralpak IG-3, 10% MeOH in CO$_2$, flow rate:=2.5 mL/min, λ=250 nm): 2.9 min (major), 5.6 min (minor).

The stereochemistry of the product was determined by NOESY experiments (data not shown).

CDC Reaction of Unsuccessful Substrates

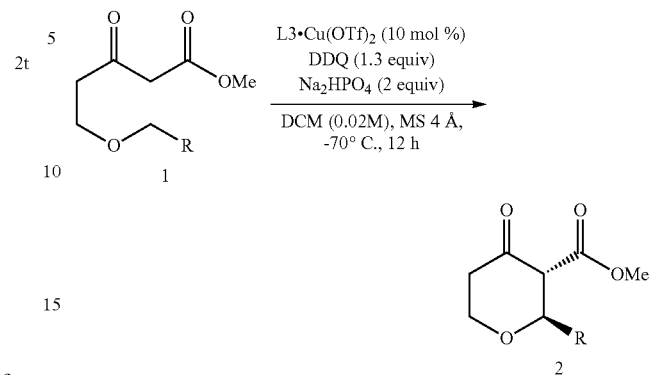

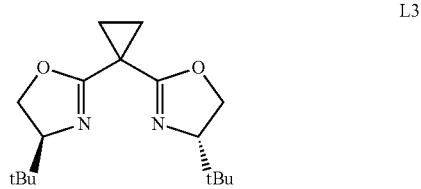

1u

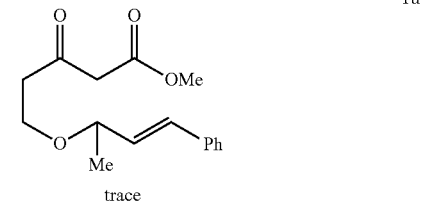

trace

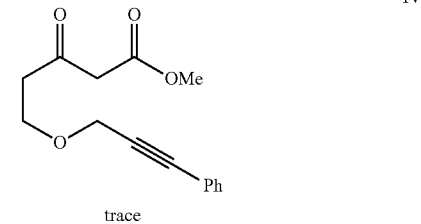

1v trace

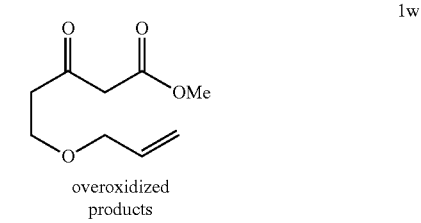

1w overoxidized products

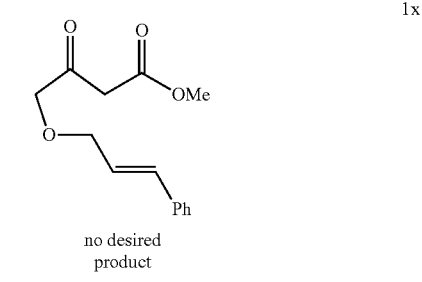

1x no desired product

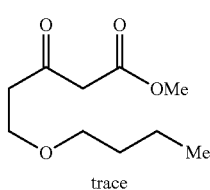

trace

Under optimized conditions, we examined a few more substrates 1u-1y (as shown above). We observed that reaction of 1u, 1v and 1y gave trace amount of desired products after 24 hours even upon warming to room temperature, and starting materials were isolated in >85% yield. The reaction of allyl ether 1w provided overoxidized side products, but the desired product was not obtained. Furthermore, we attempted to enantioselectivity access tetrahydrofurans using our optimized reaction conditions; however, 1x did not provide the desired product upon extensive reaction testing. In the reaction of 1x, cyclic acetal compounds S2x were obtained (see below).

S2x

Pale yellow solid. (38.4 mg, 74% yield, spectra data for the major compound was attached.)

$^1$H NMR (500 MHz, CDCl$_3$): δ ppm 7.46-7.40 (m, 2H), 7.38-7.29 (m, 3H), 6.89 (d, J=16.0 Hz, 1H), 6.23 (dd, J=16.0, 6.3 Hz, 1H), 6.03 (d, J=6.2 Hz, 1H), 4.94 (t, J=1.4 Hz, 1H), 4.73 (dd, J=13.6, 1.2 Hz, 1H), 4.59 (dd, J=13.5, 1.5 Hz, 1H), 4.18 (qd, J=7.1, 1.1 Hz, 2H), 1.27 (t, J=7.1 Hz, 3H).

$^{13}$C NMR (125 MHz, CDCl$_3$): δ ppm 165.3, 163.1, 137.5, 135.1, 129.2, 128.8, 127.4, 122.2, 109.8, 87.2, 69.5, 59.9, 14.5.

LRMS (ESI) calculated for C$_{15}$H$_{16}$O$_4$ [M+H]$^+$: 261.1, Found: 261.1.

Synthesis of Enol Acetate 3

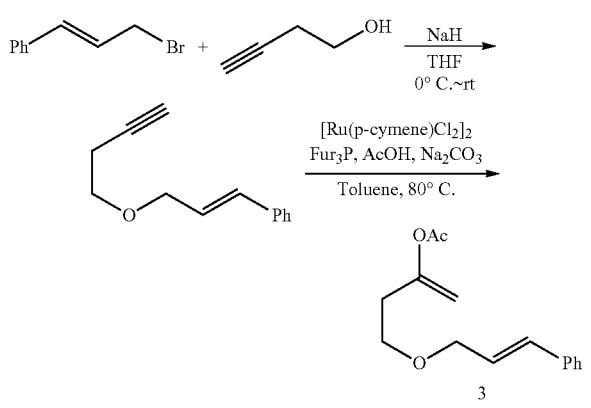

To a solution of cinnamyl bromide (0.74 mL, 5.0 mmol) and 3-butyn-1-ol (0.45 mL, 6.0 mmol) in THF was added sodium hydride (60% dispersion in mineral oil, 300 mg, 7.5 mmol) at 0° C. The solution was stirred for 3 h at ambient temperature and then saturated NH$_4$Cl solution was added to quench the reaction, followed by addition of ethyl acetate. The aqueous layer was extracted with ethyl acetate, dried and concentrated in vacuo. The crude was purified by silica gel column chromatography with ethyl acetate/hexane (1:10) to give the homopropargylic cinnamyl ether as colorless oil (649.6 mg, 70% yield). (See Gudla, V.; Balamurugan, R. *J. Org. Chem.* 2011, 76, 9919).

To a mixture of [Ru(p-cymene)Cl$_2$]$_2$ (12.2 mg, 0.02 mmol), tri(2-furyl)phosphine (9.3 mg, 0.04 mmol), Na$_2$CO$_3$ (106.0 mg, 1.0 mmol), and the homopropargylic cinnamyl ether (37.3 mg, 0.2 mmol) in toluene (4.0 mL) was added acetic acid (0.57 mL, 10 mmol). The solution was stirred at 80° C. for 15 min and then a solution of the homopropargylic cinnamyl ether (335.3 mg, 1.8 mmol) in 1.0 mL toluene was added. The resulting solution was stirred at 80° C. for 20 h. The crude mixture was cooled to room temperature and concentrated in vacuo. The crude was purified by silica gel column chromatography with ethyl acetate/hexane (1:10) to give the enol acetate 3 as colorless oil (286.8 mg, 77% yield). (See Jung, H. H.; Floreancig, P. E. *Tetrahedron* 2009, 65, 1083).

$^1$H NMR (500 MHz, CDCl$_3$): δ ppm 7.39 (d, J=7.5 Hz, 2H), 7.32 (t, J: 7.6 Hz, 2H), 7.27-7.20 (m, 1H), 6.61 (d, J=16.0 Hz, 1H), 6.28 (dt, J=16.0, 6.0 Hz, 1H), 4.86-4.75 (m, 2H), 4.16 (dd, J=6.0, 1.5 Hz, 2H), 3.62 (t, J=6.6 Hz, 2H), 2.55 (t, J=6.6 Hz, 2H), 2.13 (s, 3H).

$^{13}$C NMR (125 MHz, CDCl$_3$): δ ppm 169.3, 153.6, 136.8, 132.6, 128.7, 127.8, 126.6, 126.1, 103.1, 71.6, 67.1, 34.1, 21.2.

HRMS (ESI) calculated for C$_{15}$H$_{18}$O$_3$[M+Na]$^+$: 269.1154, Found: 269.1152.

CDC Reaction of Enol Acetate 3

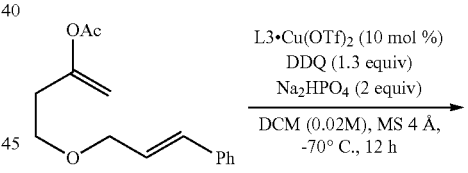

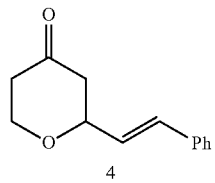

To an oven dried 20 mL reaction vial equipped with a magnetic stir bar under N$_2$ was added Na$_2$HPO$_4$ (56.8 mg, 0.4 mmol), 250 mg of 4 Å molecular sieve (powder), 1.0 mL of L3.Cu(OTf)$_2$ (0.02 M in CH$_2$Cl$_2$), and 4.0 mL of CH$_2$Cl$_2$. The solution then was stirred for 1 h. The enol acetate 3 was dissolved in 1.0 mL of CH$_2$Cl$_2$ and was added, and the solution stirred at ambient temperature for 30 minutes. The reaction was then cooled to −70° C., and DDQ (59.0 mg, 0.26 mmol) dissolved in 4.0 mL of DCM was added over 1 h by syringe pump. The reaction was stirred for 12 h at −70° C., and then 1.0 mL of Et$_3$N was added to quench the reaction. The solution was filtered over a pad of silica (4 cm)

with ethyl acetate and concentrated under reduced pressure. The crude was purified by silica gel column chromatography with ethyl acetate/hexane (1:4) to give the tetrahydropyran-4-ones 4 (27.5 mg, 68% yield, 50:50 e.r.).

CDC Reaction of Cinnamylmethyl Ether with Methyl 2-Acetoacetate

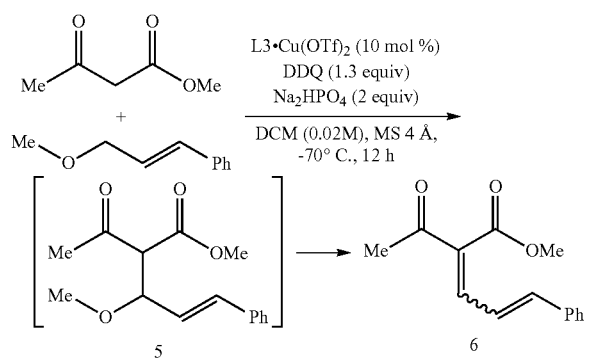

To an oven dried 20 mL reaction vial equipped with a magnetic stir bar under $N_2$ was added $Na_2HPO_4$ (56.8 mg, 0.4 mmol), 250 mg of 4 Å molecular sieve (powder), 1.0 mL of L3·Cu(OTf)$_2$ (0.02 M in $CH_2Cl_2$), and 4.0 mL of $CH_2Cl_2$. The solution then was stirred for 1 h. The cinnamylmethyl ether and methyl 2-acetoacetate were dissolved in 1.0 mL of $CH_2Cl_2$ and was added, and the solution stirred at ambient temperature for 30 minutes. The reaction was then cooled to −70° C., and DDQ (59.0 mg, 0.26 mmol) dissolved in 4.0 mL of DCM was added over 1 h by syringe pump. The reaction was stirred for 12 h at −70° C., and then 1.0 mL of Et$_3$N was added to quench the reaction. The solution was filtered over a pad of silica (4 cm) with ethyl acetate and concentrated under reduced pressure (During concentration of solvents, the desired coupling product was converted to the conjugated enones). The crude was purified by silica gel column chromatography with ethyl acetate/hexane (1:5) to give the conjugated enones (35.9 mg, 78% yield, E/Z=2.7:1). (See Paquette, L. A.; Kem, B. E.; Mendez-Andino, J. *Tetrahedron. Lett.* 1999, 40, 4129).

5. Transformation of Tetrahydropyran-4-one 2a

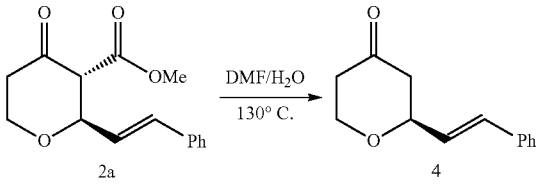

To a 5 mL reaction vial equipped with a magnetic stir bar was added the 2a (26.0 mg, 0.1 mmol, 95:5 e.r), 0.5 mL of DMF, and 20 μL of $H_2O$. The solution then was stirred for 5 h at 130° C. The crude was purified by silica gel column chromatography with ethyl acetate/hexane (1:4) to give the tetrahydropyran-4-one 4 as white solid (15.5 mg, 77% yield, 95:5 e.r.). (See Reddy, B. V. S.; Anjum, S. R.; Sridhar, B. *RSC Adv.* 2016, 6, 75133).

$^1$H NMR (500 MHz, CDCl$_3$): δ ppm 7.29-7.24 (m, 2H), 7.23-7.17 (m, 2H), 7.16-7.10 (m, 1H), 6.52 (d, J=16.0 Hz, 1H), 6.10 (dd, 1=16.0, 5.9 Hz, 1H), 4.35-4.13 (m, 2H), 3.66 (td, J=11.8, 3.0 Hz, 1H), 2.57-2.48 (m, 1H), 2.47-2.36 (m, 2H), 2.31-2.20 (m, 1H).

$^{13}$C NMR (125 MHz, CDCl$_3$): δ ppm 206.3, 136.3, 131.8, 128.7, 128.2, 128.1, 126.7, 78.3, 66.4, 48.3, 42.3.

Chiral SFC (Chiralpak IB-3, 3% MeOH in $CO_2$, flow rate=2.5 mL/min, λ=250 nm): 3.1 min (major), 2.8 min (minor).

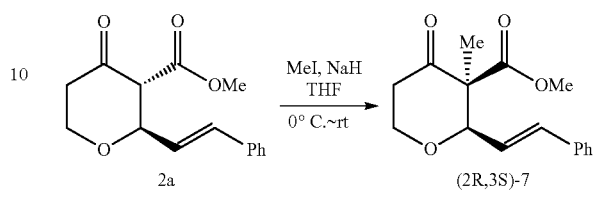

To an oven dried 5 mL reaction vial equipped with a magnetic stir bar was added the 2a (26.0 mg, 0.1 mmol, 95:5 e.r.), 4.8 mg of NaH (60% in oil, 0.12 mmol), and 1.0 mL of THF at 0° C. Methyl iodide (24.9 μL, 0.4 mmol) was added to the solution. The solution was stirred for 1 h at 0° C. and then stirred for 16 h at ambient temperature additionally. The saturated NH$_4$Cl solution was added to quench the reaction, followed by addition of ethyl acetate. The aqueous layer was extracted with ethyl acetate, dried and concentrated in vacuo. The crude was purified by silica gel column chromatography with ethyl acetate/hexane (1:4) to give the methylated tetrahydropyran-4-one 7 as colorless oil (26.5 mg, 97% yield, 95:5 e.r., 13:1 d.r.). The stereochemistry of the product was determined by NOESY experiments (data not shown).

$^1$H NMR (500 MHz, CDCl$_3$): δ ppm 7.43-7.39 (m, 2H), 7.35-7.31 (m, 2H), 7.29-7.25 (m, 1H), 6.63 (d, J=15.9 Hz, 1H), 6.49 (dd, J=15.9, 7.1 Hz, 1H), 4.39 (ddd, ==11.4, 8.1, 1.1 Hz, 1H), 3.89 (dd, J=7.2, 1.0 Hz, 1H), 3.85-3.78 (m, 1H), 3.73 (s, 3H), 3.22 (ddd, J=14.8, 12.7, 8.1 Hz, 1H), 2.48 (ddd, J=14.8, 3.1, 1.1 Hz, 1H), 1.32 (s, 3H).

$^{13}$C NMR (125 MHz, CDCl$_3$): δ ppm 203.6, 170.5, 136.4, 134.0, 128.7, 128.2, 126.9, 124.5, 86.8, 67.4, 62.2, 52.6, 41.1, 16.2.

HRMS (ESI) calculated for $C_{16}H_{18}O_4[M+Na]^+$: 297.1103, Found: 297.1110.

Chiral SFC (Chiralpak IG-3, 10% MeOH in $CO_2$, flow rate=2.5 mL/min, λ=250 nm): 3.4 min (major), 2.2 min (minor) for (2R,3S)-7 and 3.0 min (major), 5.7 min (minor) for (2R,3R)-7.

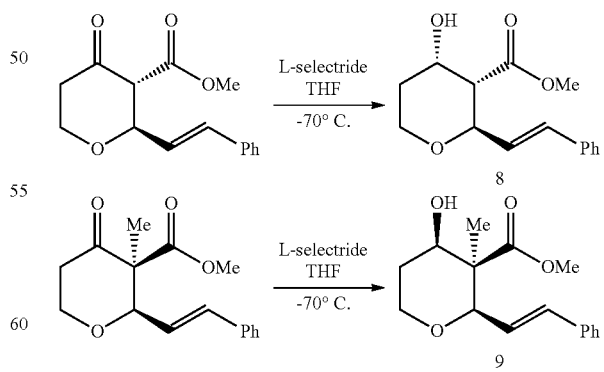

To an oven dried 5 mL reaction vial equipped with a magnetic stir bar was added the corresponding tetrahydropyran-4-one (0.1 mmol, 95:5 e.r) and 2.0 mL of THF at −70° C. The L-selectride (0.3 mL, 1.0 M in THF) was slowly added to the solution. The solution was stirred for 3 h at −70° C. and then quenched with saturated NH₄Cl solution. The aqueous layer was extracted with ethyl acetate, dried and concentrated in vacuo. The crude was purified by silica gel column chromatography with ethyl acetate/hexane (1:2) to give the corresponding tetrahydropyran-4-ol.

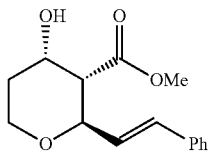

8

White solid (16.8 mg, 64% yield, 95:5 e.r.)

¹H NMR (500 MHz, CDCl₃): δ ppm 7.24-7.20 (m, 2H), 7.09-7.04 (m, 2H), 7.03-6.98 (m, 1H), 6.69 (d, J=°: 15.9 Hz, 1H), 6.32 (dd, J=16.0, 6.8 Hz, 1H), 4.73 (dd, J=10.1, 6.8 Hz, 1H), 4.14-3.97 (m, 2H), 3.67 (ddd, J=11.3, 4.8, 2.0 Hz, 1H), 3.47 (s, 1H), 3.15 (s, 3H), 2.54 (dd, J=10.3, 2.2 Hz, 1H), 1.52-1.40 (m, 2H).

¹³C NMR (125 MHz, C₆D₆): δ ppm 174.0, 137.3, 132.1, 128.8, 128.7, 128.4, 126.9, 74.2, 64.7, 62.2, 52.6, 51.3, 31.9.

HRMS (ESI) calculated for C₁₅H₁₈O₄ [M+Na]⁺: 285.1103, Found: 285.1108.

Chiral SFC (Chiralpak IC-3, 5% MeOH in CO₂, flow rate=2.5 mL/min, λ=250 nm): 3.7 min (major), 3.4 min (minor).

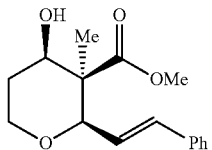

9

Colorless oil (19.6 mg, 71% yield, 95:5 e.r.)

¹H NMR (500 MHz, CDCl₃): δ ppm 7.36-7.30 (m, 2H), 7.26 (dd, J=8.4, 6.8 Hz, 2H), 7.21-7.17 (m, 1H), 6.52 (d, J=15.9 Hz, 1H), 6.37 (dd, J=15.9, 7.1 Hz, 1H), 4.08 (ddd, J=11.7, 5.3, 2.1 Hz, 1H), 3.68 (s, 3H), 3.62 (d, J=7.6 Hz, 1H), 3.55 (td, J=11.8, 2.9 Hz, 1H), 3.49 (td, J=10.7, 4.8 Hz, 1H), 3.02 (d, J=10.0 Hz, 1H), 2.20-2.08 (m, 1H), 1.93-1.81 (m, 1H), 1.30 (s, 3H).

¹³C NMR (125 MHz, CDCl₃): δ ppm 174.9, 136.9, 132.9, 128.7, 127.9, 126.8, 125.9, 85.1, 75.4, 66.6, 52.5, 52.0, 32.6, 19.8.

HRMS (ESI) calculated for C₁₆H₂₀O₄[M+Na]⁺: 299.1259, Found: 299.1266.

Chiral SFC (Chiralpak IG-3, 10% MeOH in CO₂, flow rate=2.5 mL/min, λ=250 nm): 9.0 min (major), 7.7 min (minor).

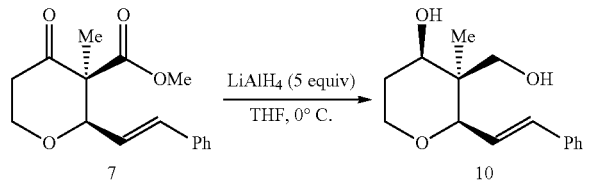 [SMILES: COC(=O)[C@]1(C)C(=O)CCO[C@@H]1/C=C/c1ccccc1 ; C[C@@]1(CO)[C@H](O)CCO[C@@H]1/C=C/c1ccccc1]

To an oven dried 5 mL reaction vial equipped with a magnetic stir bar was added LiAlH₄ (19.0 mg, 0.5 mmol), and 3.0 mL of THF at 0° C. The 7 (27.4 mg, 0.1 mmol, 95:5 e.r.) dissolved in 2.0 mL of THF was added slowly and then the solution was stirred for 5 h at 0° C. The saturated Rochelle salt solution was added to quench the reaction, followed by addition of ethyl acetate. The aqueous layer was extracted with ethyl acetate, dried and concentrated in vacuo. The crude was purified by silica gel column chromatography with ethyl acetate/hexane (1:1) to give the dialcohol 10 as colorless oil (15.4 mg, 62% yield, 95:5 e.r.).

¹H NMR (500 MHz, CDCl₃): δ ppm 7.39-7.35 (m, 2H), 7.31 (dd, J=8.5, 6.7 Hz, 2H), 7.27-7.22 (m, 1H), 6.61 (d, J=16.0 Hz, 1H), 6.17 (dd, J=15.9, 6.3 Hz, 1H), 4.28 (d, J=11.1 Hz, 1H), 4.14 (ddd, J=11.7, 5.3, 1.5 Hz, 1H), 3.73-3.63 (m, 3H), 3.59 (td, J=12.6, 2.6 Hz, 1H), 3.22 (s, 1H), 2.58 (s, 1H), 2.14 (qd, J=12.8, 5.3 Hz, 1H), 1.91-1.85 (m, 1H), 1.18 (s, 3H).

¹³C NMR (125 MHz, CDCl₃): δ ppm 136.7, 132.6, 128.7, 127.9, 126.6, 124.9, 85.0, 77.3, 67.0, 65.0, 43.0, 32.5, 18.8.

HRMS (ESI) calculated for C₁₅H₂₀O₃[M+Na]⁺: 271.1310, Found: 271.1315.

Chiral SFC (Chiralpak IC-3, 10% MeOH in CO₂, flow rate=2.5 mL/min, λ=250 nm): 3.6 min (major), 4.4 min (minor).

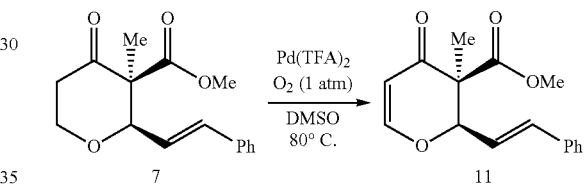

To a 50 mL round bottom flask equipped with a magnetic stir bar was added 33.2 mg of Pd(TFA)₂ (0.1 mmol), and the 7 (274.3 mg, 1.0 mmol, 93:7 e.r.). The flask was purged and filled with O₂ three times and then an oxygen balloon was attached via a needle. 10 mL of DMSO bubbled with O₂ and the solution was stirred for 2 days at 80° C. Once O₂ was vented, water was added to the solution, followed by addition of diethyl ether. The aqueous layer was extracted with diethyl ether, dried and concentrated in vacuo. The crude was purified by silica gel column chromatography with ethyl acetate/hexane (1:4) to give the cyclic enone 11 as pale yellow solid (182.4 mg, 67% yield, 93:7 e.r.). (Starting material 7 was hardly separated from product 11 by column chromatography. Therefore, the reaction should be terminated after the 7 is completely consumed. If the reaction does not give full conversion, the reaction can be performed again with crude mixture after workup process.)

¹H NMR (500 MHz, CDCl₃): δ ppm 7.48-7.42 (m, 3H.), 7.38-7.34 (m, 2H), 7.33-7.29 (m, 1H), 6.76 (d, J=15.9 Hz, 1H), 6.49 (dd, J=15.9, 8.1 Hz, 1H), 5.58 (d, J=6.0 Hz, 1H), 4.70 (d, J=8.1 Hz, 1H), 3.72 (s, 31-), 1.39 (s, 3H).

¹³C NMR (125 MHz, CDCl₃): δ ppm 190.1, 169.8, 163.1, 137.0, 135.7, 128.9, 128.8, 127.1, 121.9, 106.8, 86.7, 55.7, 52.8, 16.7.

HRMS (ESI) calculated for C₁₆H₁₆O₄ [M+Na]⁺: 295.0946, Found: 295.0951.

Chiral SFC (Chiralpak IG-3, 10% MeOH in C02, flow rate=2.5 mL/min, λ=250 nm): 5.5 min (major), 2.5 min (minor).

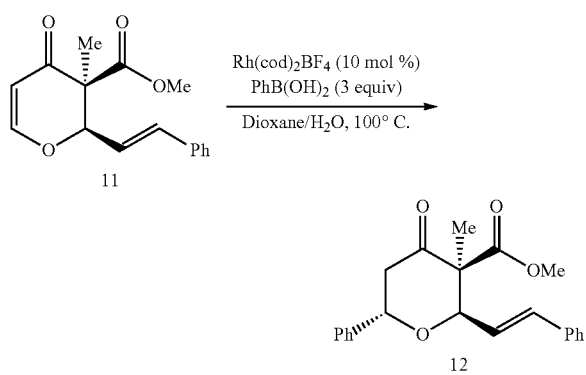

A 10 mL flask was flushed with nitrogen and charged with Rh(cod)₂BF₄ (4.1 mg, 0.01 mmol), 0.1 mL of degassed H₂O, and 2.0 mL of degassed dioxane. Phenylboronic acid (36.6 mg, 0.3 mmol) and the 11 (27.2 mg, 0.1 mmol, 93:7 e.r.) were added to the solution. After being stirred at 100° C. for 12 h, the reaction mixture was passed through a pad of silica gel with ethyl acetate and the solvent was removed under vacuum. The crude was purified by silica gel column chromatography with ethyl acetate/hexane (1:4) to give the tetrahydropyran-4-one 12 as colorless oil (26.3 mg, 75% yield, 93:7 e.r.). The stereochemistry was assigned trans configuration between C2-H and C6-H based on ¹H NMR data reported in the literature. (See (a) Kumaraswamy, G.; Ramakrishna, G.; Naresh, P.: Jagadeesh, B.; Sridhar, B. *J. Org. Chem.* 2009, 74, 8468. (b) Ramnauth, J.; Poulin, O.; Bratovanov, S. S.; Rakhit, S.; Maddaford, S. P. *Org. Let.* 2001, 3, 2571).

¹H NMR (500 MHz, CDCl₃): δ ppm 7.28-7.23 (m, 5H), 7.21-7.16 (m, 3H), 7.15-7.10 (m, 2H), 6.38 (d, J=15.9 Hz, 1H), 6.28 (dd, J:=15.9, 6.8 Hz, 1H), 5.43 (dd, J=7.4, 3.1 Hz, 1H), 3.93 (d, J=6.8 Hz, 1H), 3.63 (s, 3H), 3.35 (dd, J=15.4, 7.5 Hz, 1H), 2.99 (dd, J=15.4, 3.1 Hz, 1H), 1.13 (s, 3H).

¹³C NMR (125 MHz, CDCl₃): δ ppm 204.3, 170.6, 139.4, 136.4, 133.7, 128.9, 128.7, 128.4, 128.2, 127.3, 126.9, 124.4, 78.8, 74.8, 61.5, 52.7, 42.5, 16.6.

HRMS (ESI) calculated for C₂₂H₂₂O₄[M+Na]⁺: 373.1416, Found: 373.1430.

Chiral SFC (Chiralpak IC-3, 10% MeOH in CO₂, flow rate=2.5 mL/min, λ=250 nm): 1.7 min (major), 2.0 min (minor).

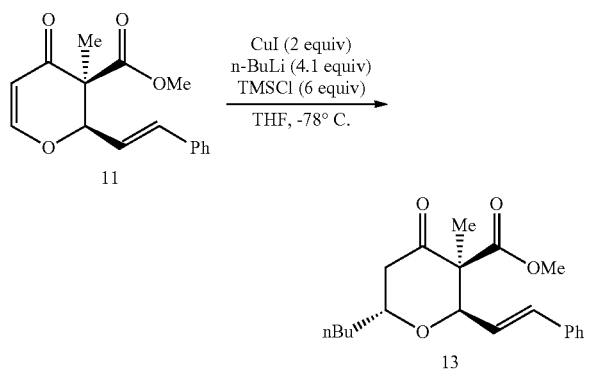

To an oven dried 10 mL vial equipped with a magnetic stir bar was added 38.1 mg of CuI (0.2 mmol), THF (1.5 mL) and n-BuLi (0.16 mL, 2.5 M in Hexanes) at 0° C. After being stirred for 20 min, the solution was cooled to −78° C. and then TMSCl (76 μl, 0.6 mmol) was added to the solution. The 11 (27.2 mg, 0.1 mmol, 93:7 e.r.) dissolved in 1.5 mL of THF was added slowly. The solution was stirred for 2.5 h at −78° C. and then quenched with saturated NH₄Cl solution. The aqueous layer was extracted with ethyl acetate, dried and concentrated in vacuo. The crude was purified by silica gel column chromatography with ethyl acetate/hexane (1:4) to give the tetrahydropyran-4-one 13 as colorless oil (25.0 mg, 76% yield, 93:7 e.r.). The trans stereochemistry of the product was determined by NOESY experiments (data not shown).

¹H NMR (500 MHz, CDCl₃): δ ppm 7.41 (d, J=7.3 Hz, 2H), 7.33 (t, J=7.5 Hz, 2H), 7.28-7.23 (m, 1H), 6.62 (d, J=15.9 Hz, 1H), 6.46 (dd, J=15.9, 7.2 Hz, 1H), 4.46-4.33 (m, 1H), 4.21 (d, J=7.1 Hz, 1H), 3.72 (s, 3H), 3.18 (dd, J=14.7, 7.0 Hz, 1H), 2.44 (dd, J=14.7, 3.5 Hz, 1H), 1.78-1.65 (m, 1H), 1.51-1.41 (m, 1H), 1.42-1.30 (m, 7H), 0.90 (td, J=5.6, 4.3, 1.7 Hz, 3H).

¹³C NMR (125 MHz, CDCl₃): δ ppm 204.6, 170.6, 136.5, 133.7, 128.7, 128.2, 126.9, 124.9, 78.7, 73.8, 61.5, 52.6, 44.3, 32.9, 27.7, 22.5, 16.9, 14.1.

HRMS (ESI) calculated for C₂₀H₂₆O₄[M+Na]⁺: 353.1729, Found: 353.1744.

Chiral SFC (Chiralpak IG-3, 10% MeOH in C02, flow rate:=2.5 mL/min, λ=250 nm): 3.8 min (major), 1.8 min (minor).

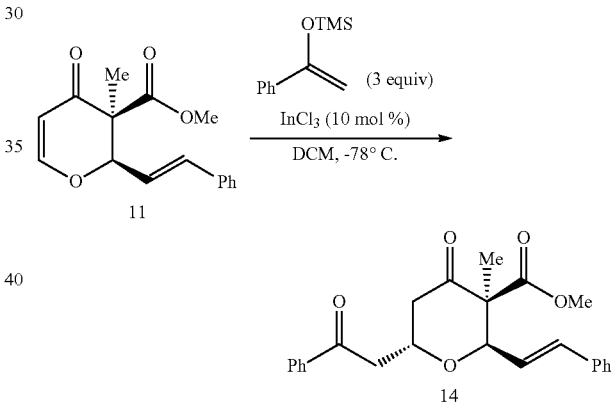

To an oven dried 10 mL vial equipped with a magnetic stir bar was added 2.2 mg of InCl₃ (0.01 mmol), the 11 (27.2 mg, 0.1 mmol, 93:7 e.r.), and CH₂Cl₂ (1 mL) at −78° C. Silyl enol ether (57.7 mg, 0.3 mmol) dissolved in 0.5 mL of CH₂Cl₂ was added slowly and then the solution was stirred for 4 h at −78° C. After warm up to 0° C., saturated KF solution was added and then stirred for 1 h at ambient temperature. The aqueous layer was extracted with ethyl acetate, dried and concentrated in vacuo. The crude was purified by silica gel column chromatography with ethyl acetate/hexane (1:4) to give the tetrahydropyran-4-one 14 as colorless oil (36.5 mg, 93% yield, 93:7 e.r., 10:1 d.r.). The trans stereochemistry of the product was determined by NOESY experiments (data not shown).

¹H NMR (500 MHz, CDCl₃): δ ppm 8.01-7.89 (m, 2H), 7.61-7.55 (m, 1H), 7.50-7.43 (m, 2H), 7.40-7.35 (m, 2H), 7.35-7.29 (m, 2H), 7.28-7.23 (m, 1H), 6.56 (d, J=15.9 Hz, 1H), 6.41 (dd, J=15.8, 7.3 Hz, 1H), 5.07 (p, J=6.1, 5.5 Hz, 1H), 4.36 (d, J=7.2 Hz, 1H), 3.73 (s, 3H), 3.38 (dd, J=16.3, 5.6 Hz, 1H), 3.26 (ddd, J=15.4, 12.8, 7.2 Hz, 2H), 2.66 (dd, J=15.3, 4.9 Hz, 1H), 1.37 (s, 3H).

$^{13}$C NMR (125 MHz, CDCl$_3$): δ ppm 204.2, 197.1, 170.5, 136.8, 136.3, 134.3, 133.7, 128.9, 128.7, 128.3, 126.9, 124.2, 80.2, 70.4, 61.4, 52.7, 43.6, 42.7, 17.2.

HRMS (ESI) calculated for C$_{24}$H$_{24}$O$_5$ [M+Na]$^+$: 415.1521, Found: 415.1529.

Chiral SFC (Chiralpak IC-3, 5% MeOH in CO$_2$, flow rate=2.5 mL/min, λ=250 nm): 8.8 min (major), 8.2 min (minor).

funnel containing 15 mL of ethyl acetate and 10 mL of H$_2$O. The layers were separated and the aqueous layer was extracted with ethyl acetate (3×15 mL). The combined organic layers were dried and concentrated in vacuo. The crude was purified by silica gel column chromatography to afford product 2a as the sole diastereomer (46.9 mg, 90% yield).

Crystal Structure of 2h.

X-ray quality crystals for 2h were obtained by slow diffusion in benzene/hexanes at r

| | |
|---|---|
| Empirical formula | C$_{15}$H$_{15}$N$_4$Br |
| Formula weight | 339.18 |
| Temperature | 99.95 K |
| Crystal system | monoclinic |
| Space group | P2$_1$ |
| Unit cell dimensions | a = 8.7786(8) Å, α = 90°. |
| | b = 8.2454(7) Å, β = 110.205(4)°. |
| | c = 10.7228(9) Å, γ = 90°. |
| Volume | 728.39(11) Å$^3$ |
| Z | 2 |
| Density (calculated) | 1.546 Mg/m$^3$ |
| Absorption coefficient | 2.831 mm$^{-1}$ |
| F(000) | 344 |
| Crystal size | 0.117 × 0.074 × 0.048 mm$^3$ |
| 2Θ range for data collection | 4.048 to 77.302°. |
| Index ranges | −15 <= h <= 15, −14 <= k <= 14, −18 <= l <= 18 |
| Reflections collected | 54501 |
| Independent reflections | 8255 [R(int) = 0.0360] |
| Data/restraints/parameters | 8255/1/182 |
| Goodness-of-fit on F$^2$ | 1.037 |
| Final R indices [I > 2sigma(I)] | R$_1$ = 0.0268, wR$_2$ = 0.0635 |
| R indices (all data) | R$_1$ = 0.0341, wR$_2$ = 0.0662 |
| Largest diff. peak and hole | 0.723 and −0.503 e · Å$^{-3}$ |

Stereochemical Models

Figure 3:
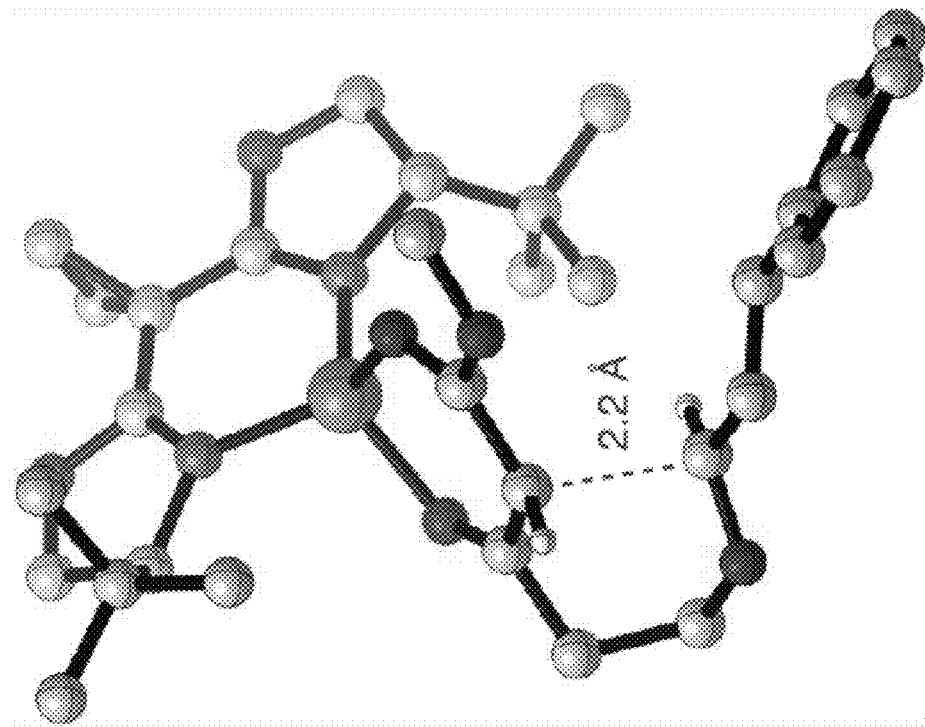
FIG. 3. PM3 optimized structure of L3.Cu(II) with 1a/(2,3-dichloro-5,6-dicyano-p-benzoquinone (DDQ) intermediate.
Figure 3:
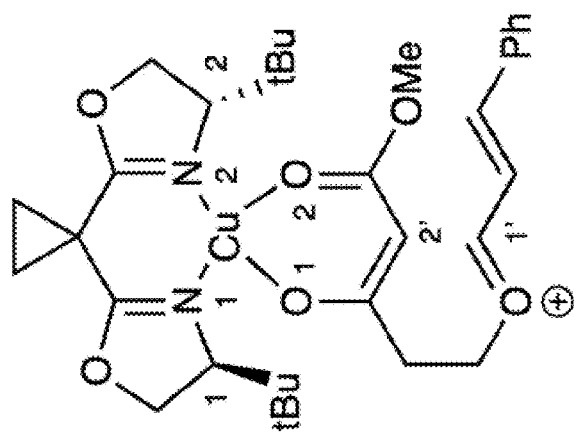
Figure 4:
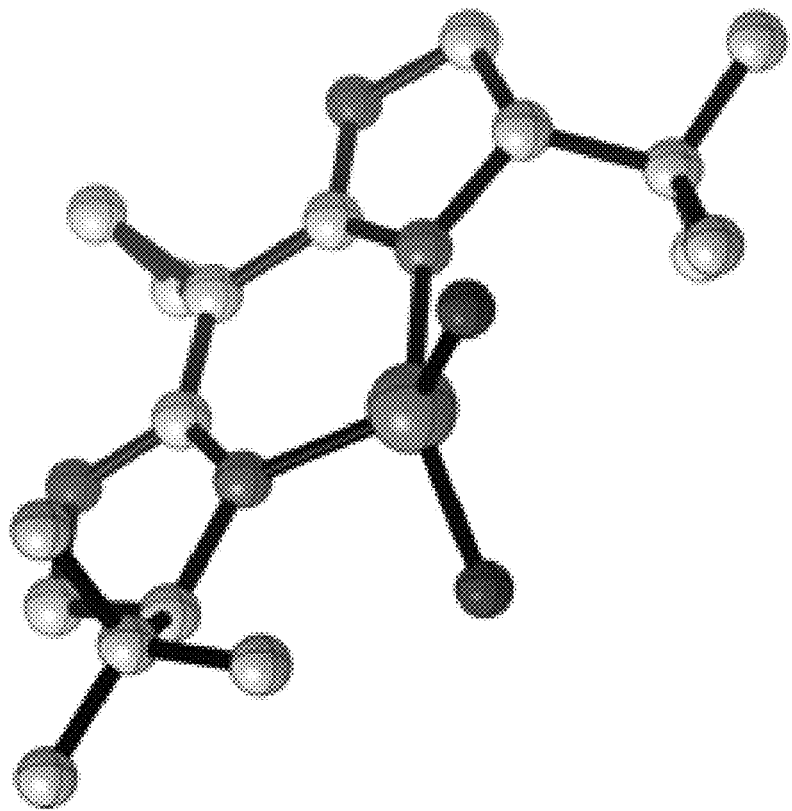
FIG. 4. PM3 optimized structure of $L3.Cu(II)(H_2O)_2$.
Figure 4:
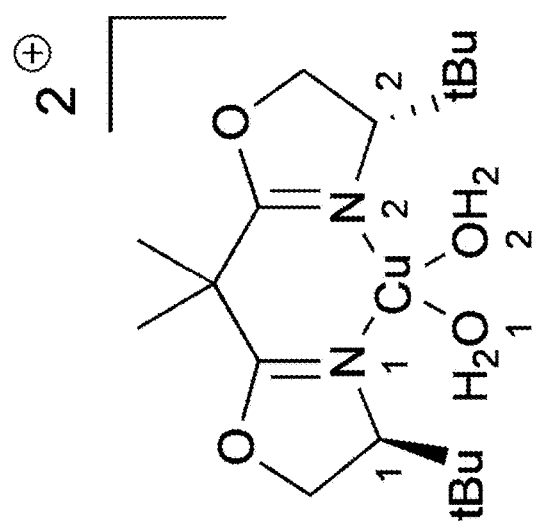

The initial geometry of L3.Cu(II)(H$_2$O)$_2$ was based on the X-ray crystal structure of [L1.Cu(H$_2$O)$_2$](SbF$_6$)$_2$ in the literature. (See Evans, D. A.; Johnson, J. S.; Olhava, E. J. *J. Am. Chem. Soc.* 2000, 122, 1635). Dihedral angles were fixed for optimization (as shown below). Geometry optimization of L3.Cu(II) with 1a/DDQ intermediate (FIG. 3) was performed using the PM3 optimized structure of L3.Cu(II) (H$_2$O)$_2$ (FIG. 4). C1'-C2' length was fixed to 2.2 Å.

Photoredox-Catalyzed CDC Reaction of 1a

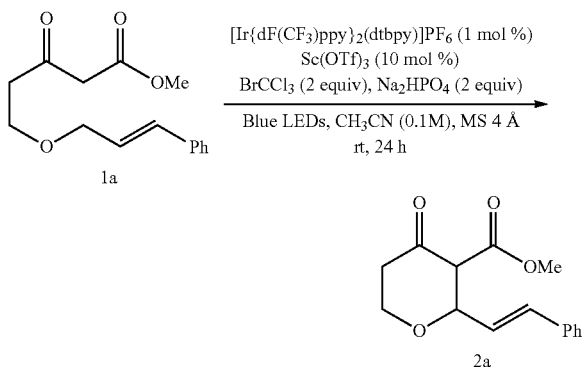

To an over dried 25 mL round bottom flask equipped with a magnetic stir bar was charged with 1a (52.5 mg, 0.2 mmol), BrCCl$_3$ (39 μl, 0.4 mmol), 150 mg 4 A MS, Sc(OTO) (9.8 mg, 0.02 mmol), and [Ir{dF(CF$_3$)ppy}$_2$(dtbbpy)]PF$_6$, (2.2 mg, 0.002 mmol). 2 mL of degassed CH$_2$Cl$_2$ was added to the flask, and the mixture was then irradiated by blue LED lamps under an atmosphere of Ar for 24 h. After the reaction was complete the mixture was poured into a separatory

REFERENCES (1) (a) Boivin, T. L. B. Tetrahedron 1987, 43, 3309-3362; (b) Marmsäter, F. P.; West, F. G. Chem. Eur. J. 2002, 8, 4346-4353.

(2) (a) Adams, D. R.; Bhatnagar, S. P. Synthesis 1977, 1977, 661-672; (b) Cloninger, M. J.; Overman, L. E. J. Am. Chem. Soc. 1999, 121, 1092-1093; (c) Jasti, R.; Vitale, J.; Rychnovsky, S. D. J. Am. Chem. Soc. 2004, 126, 9904-9905.

(3) (a) Dossetter, A. G., Jamison, T. F.; Jacobsen, E. N. Angew. Chem. Int. Ed. 1999, 38, 2398-2400; (b) Heravi, M. M.; Ahmadi, T.; Ghavidel, M.; Heidari, B.; Hamidi, H. RSC Advances 2015, 5, 101999-102075.

(4) (a) Clarke, P. A.; Santos, S. Eur. J. Org. Chem. 2006, 2006, 2045-2053; (b) Larrosa, I.; Romea, P.; Urpi, F. Tetrahedron 2008, 64, 2683-2723.

(5) (a) Nising, C. F.; Brase, S. Chem. Soc. Rev. 2008, 37, 1218-1228; (b) Nising, C. F.; Brase, S. Chem. Soc. Rev. 2012, 41, 988-999.

(6) Vetica, F.; Chauhan, P.; Dochain, S.; Enders, D. Chem. Soc. Rev. 2017, 46, 1661-1674.

(7) (a) Betori, R. C.; Miller, E. R.; Scheidt, K. A. Adv. Synth. Catal. 2017, 359, 1131-1137; (b) Morris, W. J.; Custar, D. W.; Scheidt, K. A. Org. Lett. 2005, 7, 1113-1116; (c) Wang, J.; Crane, E. A.; Scheidt, K. A. Org. Lett. 2011, 13, 3086-3089.

(8) Crane, E. A.; Zabawa, T. P.; Farmer, R. L.; Scheidt, K. A. Angew. Chem. Int. Ed. 2011, 50, 9112-9115.

(9) (a) Custar, D. W.; Zabawa, T. P.; Hines, J.; Crews, C. M.; Scheidt, K. A. J. Am. Chem. Soc. 2009, 131, 12406-12414; (b) Custar, D. W.; Zabawa, T. P.: Scheidt, K. A. J. Am. Chem. Soc. 2008, 130, 804-805.

(10) Tenenbaum, J. M.; Morris, W. J.; Custar, D. W.; Scheidt, K. A. Angew. Chem. Int. Ed. 2011, 50, 5892-5895.

(11) (a) Lee, K.; Kim, H.; Hong, J. Org. Lett. 2011, 13, 2722-2725; (b) Lee, K.; Kim, H.; Hong, J. Angew. Chem. Int. Ed. 2012, 51, 5735-5738; (c) Han, X.; Peh, G.; Floreancig, P. E. Eur. J. Org. Chem. 2013, 2013, 1193-1208; (d) Nasir, N. M.; Ermanis, K.; Clarke, P. A. Org. Biomol. Chem. 2014, 12, 3323-3335.

(12) (a) Li, C.-J. Acc. Chem. Res. 2009, 42, 335-344; (b) Yeung, C. S.; Dong, V. M. Chem. Rev. 2011, 111, 1215-1292; (c) Girard, S. A.; Knauber, T.; Li, C.-J. Angew. Chem. Int. Ed. 2014, 53, 74-100.

(13) (a) Yi, H.; Zhang, G.; Wang, H.; Huang, Z.; Wang, J.; Singh, A. K.; Lei, A. Chem. Rev. 2017, 117, 9016-9085; (b) Davies, H. M. L.; Morton, D. J. Org. Chem. 2016, 81, 343-350; (c) Gensch, T.; Hopkinson, M. N.; Glorius, F.; Wencel-Delord, J. Chem. Soc. Rev. 2016, 45, 2900-2936; (d) Arockiam, P. B.; Bruneau, C.; Dixneuf, P. H. Chem. Rev. 2012, 112, 5879-5918; (e) Colby, D. A.; Tsai, A. S.; Bergman, R. G.; Ellman, J. A. Acc. Chem. Res. 2012, 45, 814-825; (f) Gutekunst, W. R.; Baran, P. S. Chem. Soc. Rev. 2011, 40, 1976-1991; (g) Lyons, T. W.; Sanford, M. S. Chem. Rev. 2010, 110, 1147-1169.

(14) (a) Ying, B.-P.; Trogden, B. G.; Kohiman, D. T.; Liang, S. X.; Xu, Y.-C. Org. Lett. 2004, 6, 1523-1526; (b) Zhang, Y.; Li, C.-J. Angew. Chem. Int. Ed. 2006, 45, 1949-1952.

(15) (a) Brizgys, G. J.; Jung, H. H.; Floreancig, P. E. Chem. Sci. 2012, 3, 438-442; (b) Cui, Y.: Floreancig, P. E. Org. Lett. 2012, 14, 1720-1723: (c) Liu, L.; Floreancig, P. E. Org. Let. 2009, 11, 3152-3155; (d) Liu, L.; Floreancig, P. E. Angew. Chem. Int. Ed. 2010, 49, 5894-5897; (e) Tu, W.; Liu, L.; Floreancig, P. E. Angew. Chem. Int. Ed. 2008, 47, 4184-4187.

(16) (a) Guo, C.; Song, J.; Luo, S.-W.; Gong, L.-Z. Angew. Chem. Int. Ed. 2010, 49, 5558-5562; (b) Zhang, G.; Zhang, Y.; Wang, R. Angew. Chem. Int. Ed. 2011, 50, 10429-10432; (c) Zhang, J.; Tiwari, B.; Xing, C.; Chen, X.; Chi, Y. R. Angew. Chem. Int. Ed. 2012, 51, 3649-3652; (d) Tan, Y.; Yuan, W.; Gong, L.; Meggers, E. Angew. Chem. Int. Ed. 2015, 54, 13045-13048; (e) Yang, Q.; Zhang, L.; Ye, C.; Luo, S.; Wu, L.-Z.; Tung, C.-H. Angew. Chem. Int. Ed. 2017, 56, 3694-3698.

(17) (a) Cui, Y.; Villafane, L. A.; Clausen, D. J.; Floreancig, P. E. Tetrahedron 2013, 69, 7618-7626; (b) Meng, Z.; Sun, S.; Yuan, H.; Lou, H.; Liu, L. Angew. Chem. Int. Ed. 2014, 53, 543-547.

(18) CCDC 1817530 (2h) contains the supplementary crystallographic data. See Supp. Info. for details.

(19) Evans, D. A.; Scheidt, K. A.; Johnston, J. N.; Willis, M. C. J. Am. Chem. Soc. 2001, 123, 4480-4491.

(20) Clarke, P. A.; Sellars, P. B.; Nasir, N. M. Org. Biomol. Chem. 2015, 13, 4743-4750.

(21) Diao, T.; Stahl, S. S. J. Am. Chem. Soc. 2011, 133, 14566-14569.

(22) The relative stereochemistry of 12 was assigned trans con-figuration between C2-H and C6-H based on data reported in the literature. See: (a) Kumaraswamy, G.; Ramakrishna, G.; Naresh, P.; Jagadeesh, B.; Sridhar, B. J. Org. Chem. 2009, 74, 8468-8471; (b) Ramnauth, J.; Poulin, O.; Bratovanov, S. S.; Rakhit, S.; Maddaford, S. P. Org. Lett. 2001, 3, 2571-2573.

(23) The trans stereochemistry of the products was determined by NOESY experiments. See Figure SI and S2 in Supp. Info. for details.

(24) Chua, S.-S.; Alni, A.; Jocelyn Chan, L.-T.; Yamane, M.; Loh, T.-P. Tetrahedron 2011, 67, 5079-5082.

(25) (a) Carpenter, J.; Northrup, A. B.; Chung, d.; Wiener, J. J. M.; Kim, S.-G.; MacMillan, D. W. C. Angew. Chem. Int. Ed. 2008, 47, 3568-3572; (b) Smith, A. B.; Tomioka, T.; Risatti, C. A.; Sperry, J. B.; Sfouggatakis, C. Org. Lett. 2008, 10, 4359-4362; (c) Olier, C.; Kaafarani, M.; Gastaldi, S.; Bertrand, M. P. Tetrahedron 2010,66, 413-445.

(26) (a) Ferrid, L.; Reymond, S.; Capdevielle, P.; Cossy, J. Org. Lett. 2007, 9, 2461-2464; (b) Brazeau, J.-F.; Guilbault, A.-A.; Kochuparampil, J.; Mochirian, P.; Guindon, Y. Org. Lett. 2010, 12, 36-39.

(27) Tucker, J. W.; Narayanam, J. M. R.; Shah, P. S.; Stephenson, C. R. J. Chem. Commun. 2011,47, 5040-5042.

(28) Skubi, K. L.; Blum, T. R.; Yoon, T. P. Chem. Rev. 2016, 116, 10035.

(29) Pangborn, A. B.; Giardelo, M. A.; Grubbs, R. H.; Rosen, R. K.; Timmers, F. J. Organometallies 1996, 15, 1518.

(30) Evans, D. A.; Peterson, G. S.; Johnson, J. S.; Barnes, D. M.; Campos, K. R.; Woerpel, K. A. J. Org. Chem. 1998, 63, 4541.

(40) Stewart, J. J. P. J. Comput. Chem. 1989, 10, 209.

(41) Krishna, T. R.; Jayaraman, N, J. Org. Chem. 2003, 68, 9694.

(42) Gudla, V.; Balamurugan, R. J. Org. Chem. 2011, 76, 9919.

(43) Jung, H. H.; Floreancig, P. E. Tetrahcdron 2009, 65, 1083.

(44) Paquette, L. A.; Kern, B. E.; Mendez-Andino, J. Tetrahedron. Lett. 1999, 40, 4129.

(45) Reddy, B. V. S.; Anjum, S. R.; Sridhar, B. RSC Adv. 2016, 6, 75133.

(46) (a) Kumaraswamy, G.; Ramakrishna, G.; Naresh, P.; Jagadeesh, B.; Sridhar, B. J. Org. Chem. 2009, 74, 8468. (b) Ramnauth, J.; Poulin, O.; Bratovanov, S. S.; Rakhit, S.; Maddaford, S. P. Org. Lett. 2001, 3, 2571.

(47) Evans, D. A.; Johnson, J. S.; Olhava, E. J. Am. Chem. Sue. 2000, 122, 1635.

(48) Wan et al., "Organocatalytic Redox Deracemization of Cyclic Benzylic Ethers Enabled by An Acetal Pool Strategy," Angew. Chem. Int. Ed. Engl. 2017, 56(18):5116-5120.

(49) Lu et al., "Redox deracemization of 1,3,4,9-tetrahydropyrano[3,4-b]indoles," Chem. Commun. 2018, 54, 4445-4448.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having Formula I:

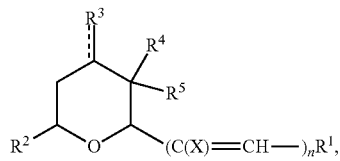

wherein:

X is hydrogen or alkyl;

n is 0-6;

R$^1$ is aryl or heteroaryl, optionally wherein R$^1$ is a single 5-membered or 6-membered ring or two or more fused 5-membered or 6-membered rings, wherein the single ring or two or more fused rings are carbocyclic or heterocyclic rings containing one or more heteroatoms selected from N, O, and S, optionally wherein the single ring or more fused rings are substituted at one or more positions with a substituent selected from alkyl, alkoxy, halo, amino, and cyano;

R$^2$ is hydrogen, alkyl, aryl,

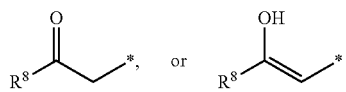

wherein R$^8$ is hydrogen, alkyl, or aryl;

R$^3$ hydroxyl or oxo;

R$^4$ is hydrogen or alkyl;

R$^5$ is

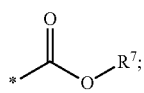

and

R$^7$ is hydrogen or alkyl.

2. The compound of claim 1 having a Formula I(a):

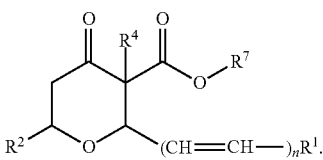

3. The compound of claim 1 having a Formula I(b):

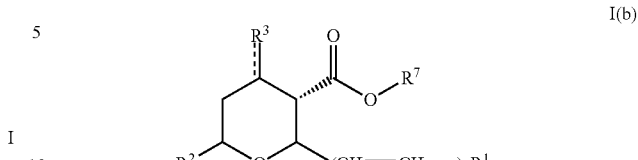

4. The compound of claim 1 having a Formula Ic:

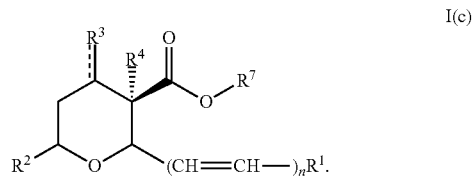

5. The compound of claim 1 having a Formula Id:

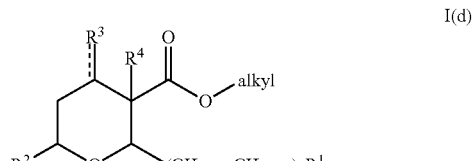

6. The compound of claim 1 having a Formula I(e):

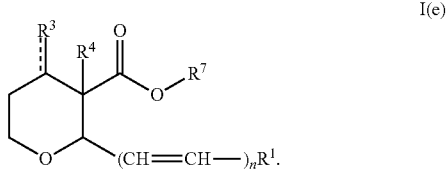

7. The compound of claim 1, wherein n is 0-2, and R$^1$ is selected from phenyl optionally substituted at one or more positions with alkyl, alkoxy, halo, or haloalkyl; naphthyl; indolyl; and thiazolyl.

8. The compound of claim 1 having a Formula I(f):

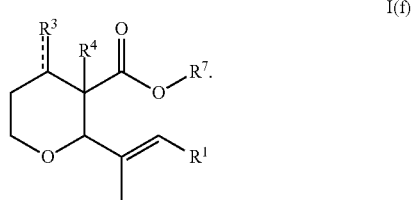

9. The compound of claim 1 having a Formula I(h):
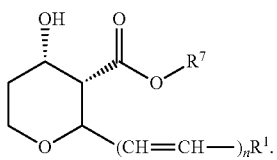
10. The compound of claim 1 having a Formula I(i):
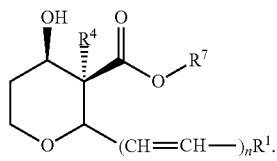
11. The compound of claim 1 having a Formula I(l):
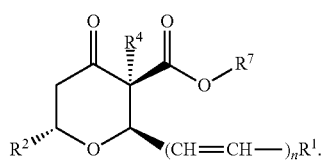
12. The compound of claim 1 having a formula selected from:
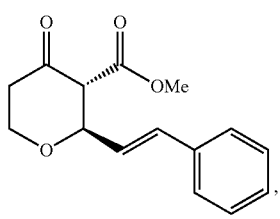
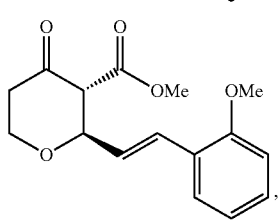
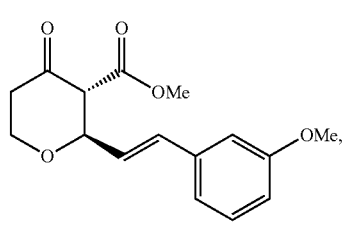
-continued
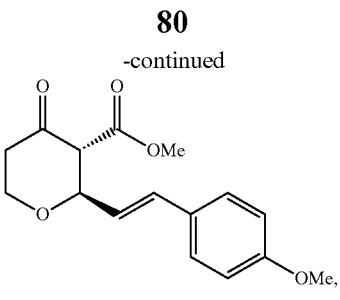
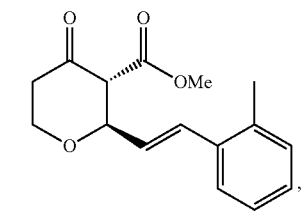
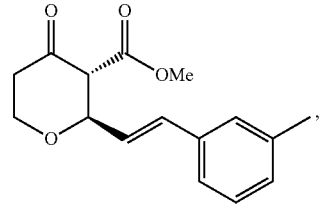
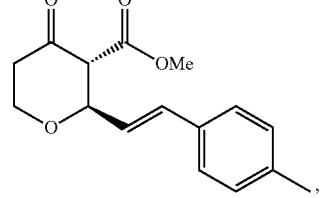
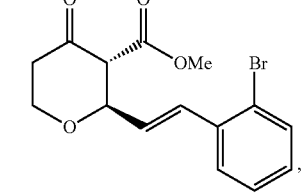
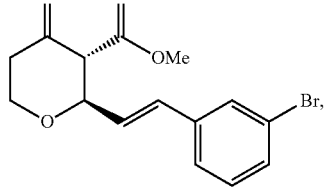
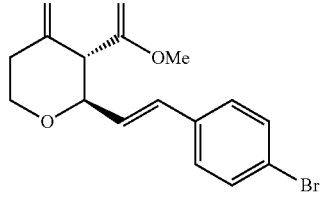
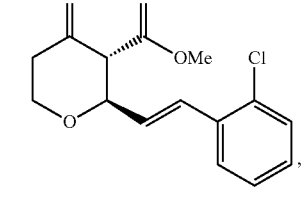

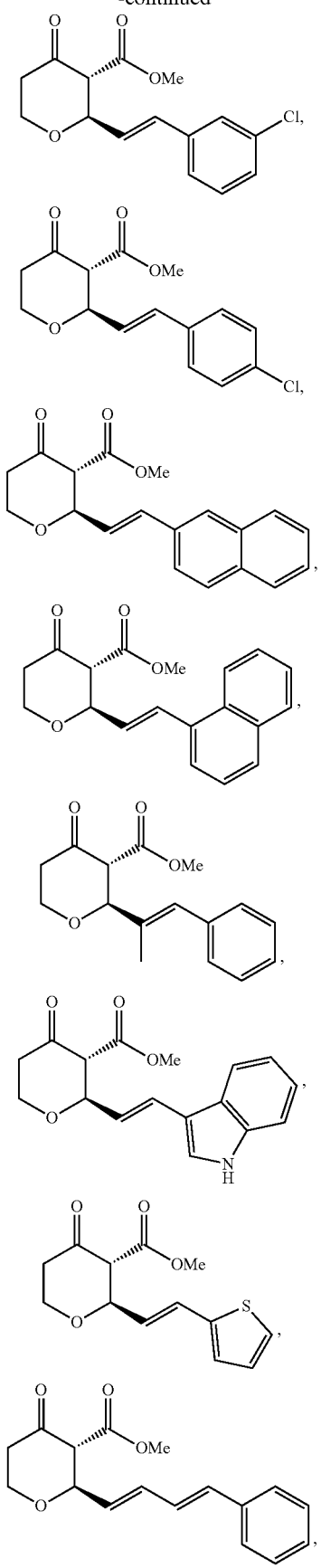
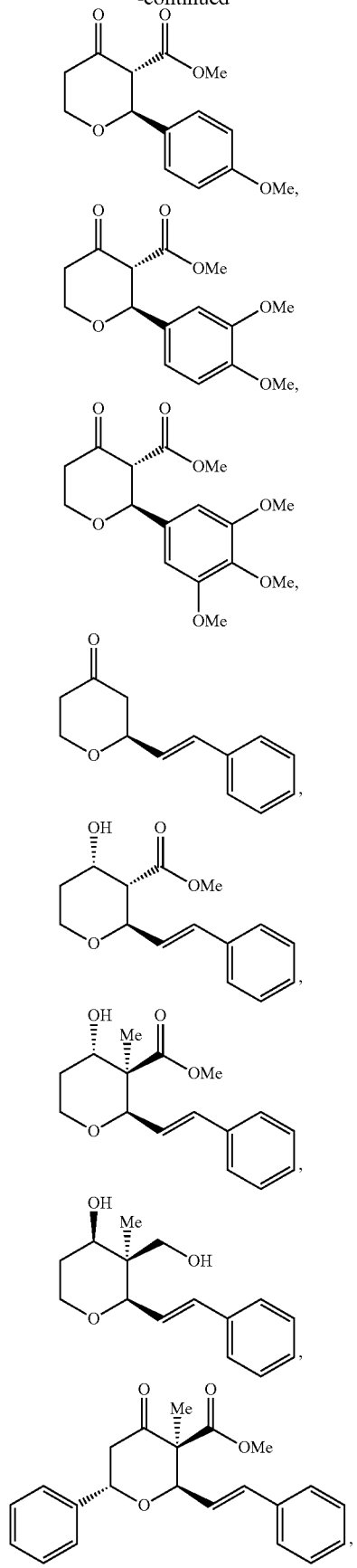

-continued
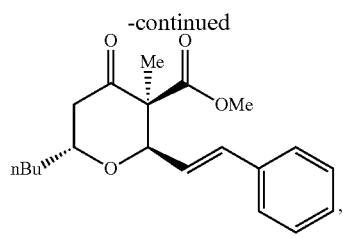
,
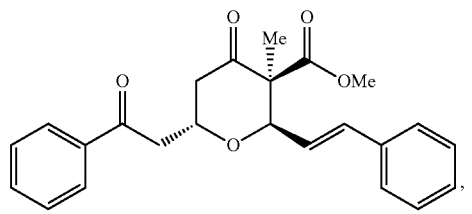
, and
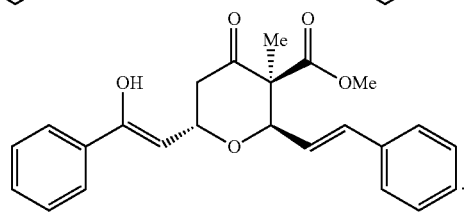
.
* * * * *